(12) United States Patent
Karmarkar et al.

(10) Patent No.: US 9,248,270 B2
(45) Date of Patent: Feb. 2, 2016

(54) METHODS AND APPARATUS FOR FABRICATING LEADS WITH CONDUCTORS AND RELATED FLEXIBLE

(75) Inventors: Parag V. Karmarkar, Columbia, MD (US); Paul A. Bottomley, Columbia, MD (US); Justin M. Allen, Baltimore, MD (US); William A. Edelstein, Baltimore, MD (US); Peter Piferi, Orange, CA (US); Brian Gore, Fort Lauderdale, FL (US)

(73) Assignees: Boston Scientific Neuromodulation Corporation, Valencia, CA (US); MRI Interventions, Inc., Memphis, TN (US)

( * ) Notice: Subject to any disclaimer, the term of this patent is extended or adjusted under 35 U.S.C. 154(b) by 1063 days.

(21) Appl. No.: 12/047,832

(22) Filed: Mar. 13, 2008

(65) Prior Publication Data
US 2008/0262584 A1  Oct. 23, 2008

Related U.S. Application Data

(60) Provisional application No. 60/895,619, filed on Mar. 19, 2007, provisional application No. 60/912,835, filed on Apr. 19, 2007, provisional application No. 60/955,730, filed on Aug. 14, 2007.

(51) Int. Cl.
*A61N 1/05* (2006.01)
*A61N 1/04* (2006.01)
(Continued)

(52) U.S. Cl.
CPC ............ *A61N 1/05* (2013.01); *A61N 1/0488* (2013.01); *B29C 33/126* (2013.01); *G01N 3/32* (2013.01); *A61N 2001/086* (2013.01); *B29L 2031/753* (2013.01); *Y10T 29/49071* (2015.01)

(58) Field of Classification Search
CPC ..... A61N 1/05; A61N 1/0488; A61N 1/0551; A61N 2001/086
USPC .............................. 607/116, 121, 122; 174/32
See application file for complete search history.

(56) References Cited

U.S. PATENT DOCUMENTS

| 1,436,323 A | 11/1922 | Schnable et al. |
| 3,969,930 A | 7/1976 | Prevorsek et al. |

(Continued)

FOREIGN PATENT DOCUMENTS

| EP | 1209460 | 5/2002 |
| EP | 1336116 A1 | 8/2003 |

(Continued)

OTHER PUBLICATIONS

International Search Report and Written Opinion issued by the International Search Authority for International Application PCT/US2008/003420; mail date Jul. 15, 2008.

(Continued)

*Primary Examiner* — Tammie K Heller
(74) *Attorney, Agent, or Firm* — Lowe Graham Jones PLLC; Bruce E. Black

(57) ABSTRACT

MRI/RF compatible leads include at least one conductor, a respective conductor having at least one segment with a multi-layer stacked coil configuration. The lead can be configured so that the lead heats local tissue less than about 10 degrees Celsius (typically about 5 degrees Celsius or less) or does not heat local tissue when a patient is exposed to target RF frequencies at a peak input SAR of at least about 4 W/kg and/or a whole body average SAR of at least about 2 W/kg. Related leads and methods of fabricating leads are also described.

39 Claims, 67 Drawing Sheets

(51) Int. Cl.
*B29C 33/12* (2006.01)
*G01N 3/32* (2006.01)
*A61N 1/08* (2006.01)
*B29L 31/00* (2006.01)

(56) References Cited

U.S. PATENT DOCUMENTS

| | | | |
|---|---|---|---|
| 4,006,748 A | 2/1977 | Schulman | |
| 4,149,104 A * | 4/1979 | Yoshimori | 313/340 |
| 4,165,634 A | 8/1979 | Prevorsek et al. | |
| 5,222,506 A | 6/1993 | Patrick et al. | |
| 5,294,886 A | 3/1994 | Duerr | |
| 5,350,419 A | 9/1994 | Bendel et al. | |
| 5,405,374 A | 4/1995 | Stein | |
| 5,582,609 A * | 12/1996 | Swanson et al. | 606/39 |
| 6,018,683 A | 1/2000 | Verness et al. | |
| 6,061,598 A | 5/2000 | Verness et al. | |
| 6,119,042 A | 9/2000 | Verness et al. | |
| 6,181,969 B1 | 1/2001 | Gord | |
| 6,284,971 B1 | 9/2001 | Atalar et al. | |
| 6,285,910 B1 | 9/2001 | Verness et al. | |
| 6,496,006 B1 | 12/2002 | Vrijheid | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,765,779 B2 | 7/2004 | Stevenson et al. | |
| 6,765,780 B2 | 7/2004 | Brendel | |
| 6,785,576 B2 | 8/2004 | Verness | |
| 6,829,509 B1 | 12/2004 | MacDonald et al. | |
| 6,888,715 B2 | 5/2005 | Stevenson et al. | |
| 6,949,929 B2 | 9/2005 | Gray et al. | |
| 6,987,660 B2 | 1/2006 | Stevenson et al. | |
| 6,993,373 B2 | 1/2006 | Vrijheid et al. | |
| 7,012,192 B2 | 3/2006 | Stevenson et al. | |
| 7,013,180 B2 | 3/2006 | Villaseca et al. | |
| 7,035,076 B1 | 4/2006 | Stevenson | |
| 7,035,077 B2 | 4/2006 | Brendel | |
| 7,038,900 B2 | 5/2006 | Stevenson et al. | |
| 7,123,013 B2 | 10/2006 | Gray | |
| 7,136,273 B2 | 11/2006 | Stevenson et al. | |
| 7,199,995 B2 | 4/2007 | Stevenson | |
| 7,244,150 B1 | 7/2007 | Brase et al. | |
| 7,310,216 B2 | 12/2007 | Stevenson et al. | |
| 7,437,193 B2 | 10/2008 | Parramon et al. | |
| 7,450,997 B1 | 11/2008 | Pianca et al. | |
| 7,489,495 B2 | 2/2009 | Stevenson | |
| 7,535,693 B2 | 5/2009 | Stevenson et al. | |
| 7,623,335 B2 | 11/2009 | Stevenson et al. | |
| 7,623,336 B2 | 11/2009 | Stevenson et al. | |
| 7,672,734 B2 | 3/2010 | Anderson et al. | |
| 7,689,288 B2 | 3/2010 | Stevenson et al. | |
| 7,702,387 B2 | 4/2010 | Stevenson et al. | |
| 7,751,903 B2 | 7/2010 | Stevenson et al. | |
| 7,761,165 B1 | 7/2010 | He et al. | |
| 7,765,005 B2 | 7/2010 | Stevenson | |
| 7,783,359 B2 | 8/2010 | Meadows | |
| 7,787,958 B2 | 8/2010 | Stevenson | |
| 7,792,590 B1 | 9/2010 | Pianca et al. | |
| 7,809,446 B2 | 10/2010 | Meadows | |
| 7,822,460 B2 | 10/2010 | Halperin et al. | |
| 7,844,319 B2 | 11/2010 | Susil et al. | |
| 7,853,324 B2 | 12/2010 | Stevenson et al. | |
| 7,853,325 B2 | 12/2010 | Dabney et al. | |
| 7,881,808 B2 * | 2/2011 | Borgaonkar et al. | 607/122 |
| 7,899,551 B2 | 3/2011 | Westlund et al. | |
| 7,916,013 B2 | 3/2011 | Stevenson | |
| 7,917,219 B2 | 3/2011 | Stevenson et al. | |
| 7,920,916 B2 | 4/2011 | Johnson et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,271,094 B1 | 9/2012 | Moffitt et al. | |
| 8,295,944 B2 | 10/2012 | Howard et al. | |
| 8,364,278 B2 | 1/2013 | Pianca et al. | |
| 8,391,985 B2 | 3/2013 | McDonald | |
| 2003/0079900 A1 | 5/2003 | Hahn et al. | |
| 2003/0083726 A1 | 5/2003 | Zeijlemaker et al. | |
| 2003/0144721 A1 | 7/2003 | Villaseca et al. | |
| 2003/0179536 A1 | 9/2003 | Stevenson et al. | |
| 2003/0213604 A1 | 11/2003 | Stevenson et al. | |
| 2003/0213605 A1 | 11/2003 | Brendel et al. | |
| 2003/0236562 A1 | 12/2003 | Kuzma | |
| 2004/0016301 A1 | 1/2004 | Moreno et al. | |
| 2004/0064176 A1 | 4/2004 | Min et al. | |
| 2004/0113306 A1 | 6/2004 | Rapacki et al. | |
| 2004/0162600 A1 | 8/2004 | Williams | |
| 2004/0201947 A1 | 10/2004 | Stevenson et al. | |
| 2004/0257747 A1 | 12/2004 | Stevenson et al. | |
| 2005/0007718 A1 | 1/2005 | Stevenson et al. | |
| 2005/0090886 A1 | 4/2005 | MacDonald et al. | |
| 2005/0190527 A1 | 9/2005 | Stevenson et al. | |
| 2005/0201039 A1 | 9/2005 | Stevenson et al. | |
| 2005/0218897 A1 | 10/2005 | Schulz et al. | |
| 2005/0219787 A1 | 10/2005 | Stevenson et al. | |
| 2005/0247475 A1 | 11/2005 | Stevenson et al. | |
| 2005/0248907 A1 | 11/2005 | Stevenson et al. | |
| 2006/0028784 A1 | 2/2006 | Brendel | |
| 2006/0030774 A1 | 2/2006 | Gray et al. | |
| 2006/0085043 A1 | 4/2006 | Stevenson | |
| 2006/0212096 A1 | 9/2006 | Stevenson | |
| 2006/0221543 A1 | 10/2006 | Stevenson et al. | |
| 2006/0229693 A1 | 10/2006 | Bauer et al. | |
| 2007/0019362 A1 | 1/2007 | Stevenson et al. | |
| 2007/0035910 A1 | 2/2007 | Stevenson | |
| 2007/0088416 A1 | 4/2007 | Atalar et al. | |
| 2007/0106332 A1 | 5/2007 | Denker et al. | |
| 2007/0112398 A1 | 5/2007 | Stevenson et al. | |
| 2007/0123949 A1 | 5/2007 | Dabney et al. | |
| 2007/0150036 A1 | 6/2007 | Anderson | |
| 2007/0279834 A1 | 12/2007 | Stevenson et al. | |
| 2007/0288058 A1 | 12/2007 | Halperin et al. | |
| 2008/0033497 A1 | 2/2008 | Bulkes et al. | |
| 2008/0049376 A1 | 2/2008 | Stevenson et al. | |
| 2008/0065181 A1 | 3/2008 | Stevenson | |
| 2008/0071313 A1 | 3/2008 | Stevenson et al. | |
| 2008/0116997 A1 | 5/2008 | Dabney et al. | |
| 2008/0119917 A1 | 5/2008 | Geistert | |
| 2008/0119919 A1 | 5/2008 | Atalar et al. | |
| 2008/0132987 A1 | 6/2008 | Westlund et al. | |
| 2008/0161886 A1 | 7/2008 | Stevenson et al. | |
| 2008/0195180 A1 | 8/2008 | Stevenson et al. | |
| 2008/0243218 A1 | 10/2008 | Bottomley et al. | |
| 2008/0269591 A1 | 10/2008 | Halperine et al. | |
| 2009/0116167 A1 | 5/2009 | Stevenson et al. | |
| 2009/0163980 A1 | 6/2009 | Stevenson | |
| 2009/0163981 A1 | 6/2009 | Stevenson et al. | |
| 2009/0187222 A1 | 7/2009 | Barker | |
| 2009/0192577 A1 | 7/2009 | Desai | |
| 2009/0259265 A1 | 10/2009 | Stevenson et al. | |
| 2009/0276021 A1 | 11/2009 | Meadows | |
| 2010/0016936 A1 | 1/2010 | Stevenson et al. | |
| 2010/0023000 A1 | 1/2010 | Stevenson et al. | |
| 2010/0023095 A1 | 1/2010 | Stevenson et al. | |
| 2010/0060431 A1 | 3/2010 | Stevenson et al. | |
| 2010/0076508 A1 | 3/2010 | McDonald et al. | |
| 2010/0076535 A1 | 3/2010 | Pianca et al. | |
| 2010/0094364 A1 | 4/2010 | McDonald | |
| 2010/0100164 A1 | 4/2010 | Johnson et al. | |
| 2010/0160997 A1 | 6/2010 | Johnson et al. | |
| 2010/0168821 A1 | 7/2010 | Johnson et al. | |
| 2010/0174349 A1 | 7/2010 | Stevenson et al. | |
| 2010/0191236 A1 | 7/2010 | Johnson et al. | |
| 2010/0191306 A1 | 7/2010 | Stevenson et al. | |
| 2010/0194541 A1 | 8/2010 | Stevenson et al. | |
| 2010/0198312 A1 | 8/2010 | Stevenson et al. | |
| 2010/0217262 A1 | 8/2010 | Stevenson et al. | |
| 2010/0222856 A1 | 9/2010 | Halperin et al. | |
| 2010/0222857 A1 | 9/2010 | Halperin et al. | |
| 2010/0231327 A1 | 9/2010 | Johnson et al. | |
| 2010/0256693 A1 | 10/2010 | McDonald et al. | |
| 2010/0268298 A1 | 10/2010 | Moffitt et al. | |
| 2010/0280584 A1 | 11/2010 | Johnson et al. | |

(56) References Cited

U.S. PATENT DOCUMENTS

| | | |
|---|---|---|
| 2010/0318160 A1 | 12/2010 | Stevenson |
| 2010/0321163 A1 | 12/2010 | Stevenson |
| 2010/0324639 A1 | 12/2010 | Stevenson et al. |
| 2010/0324640 A1 | 12/2010 | Bauer et al. |
| 2010/0326701 A1 | 12/2010 | McDonald |
| 2011/0001610 A1 | 1/2011 | Stevenson et al. |
| 2011/0004267 A1 | 1/2011 | Meadows |
| 2011/0005069 A1 | 1/2011 | Pianca |
| 2011/0009932 A1 | 1/2011 | McDonald et al. |
| 2011/0022140 A1 | 1/2011 | Stevenson et al. |
| 2011/0029043 A1 | 2/2011 | Frysz et al. |
| 2011/0040343 A1 | 2/2011 | Johnson et al. |
| 2011/0046700 A1 | 2/2011 | McDonald et al. |
| 2011/0054582 A1 | 3/2011 | Dabney et al. |
| 2011/0066212 A1 | 3/2011 | Stevenson et al. |
| 2011/0078900 A1 | 4/2011 | Pianca et al. |
| 2011/0130817 A1 | 6/2011 | Chen |
| 2011/0130818 A1 | 6/2011 | Chen |
| 2011/0230893 A1 | 9/2011 | Barker |
| 2011/0238129 A1 | 9/2011 | Moffitt et al. |
| 2011/0288403 A1 | 11/2011 | Kondabatini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0316615 A1 | 12/2012 | DiGiore et al. |
| 2013/0274844 A1 | 10/2013 | Leven et al. |
| 2014/0058488 A1 | 2/2014 | Leven |
| 2015/0018917 A1 | 1/2015 | Wechter et al. |

FOREIGN PATENT DOCUMENTS

| | | |
|---|---|---|
| EP | 1105966 A1 | 11/2005 |
| EP | 1923094 | 10/2007 |
| EP | 1923094 | 5/2008 |
| JP | 2004016739 | 1/1992 |
| JP | 2002355849 | 12/2002 |
| WO | WO 96/02921 | 2/1996 |
| WO | WO 9606655 | 3/1996 |
| WO | WO 96/06655 | 5/1996 |
| WO | 00/77926 A1 | 12/2000 |
| WO | 02/42790 A1 | 5/2002 |
| WO | 2004073791 A1 | 9/2004 |
| WO | WO 2004095281 A2 | 11/2004 |
| WO | 2005103748 | 11/2005 |
| WO | WO 2005114685 A1 | 12/2005 |
| WO | WO2006119492 A2 | 11/2006 |
| WO | WO 2007102893 A2 | 9/2007 |
| WO | WO 2007117302 A2 | 10/2007 |
| WO | WO2007118194 A2 | 10/2007 |
| WO | WO 2007145671 A2 | 12/2007 |
| WO | 2008/115426 | 9/2008 |

OTHER PUBLICATIONS

Partial International Search Report issued by the International Search Authority for International Application PCT/US2008/003266; mail date Jul. 28, 2008.

Baker KB, Tkach J, Hall JD, Nyenhuis JA, Shellock FG and Rezai AR (2001). Reduction of Magnetic Resonance Imaging-related Heating in Deep Brain Stimulation Leads Using a Lead Management Device. *Operative Neurosurgery* 57: 392-397.

Gray RW, Bibens WT and Shellock FG (2005). Simple Design Changes to Wires to Substantially Reduce MRI-induced heating at 1.5 T: Implications for Implanted Leads. *Magnetic Resonance Imaging* 23: 887-891.

Helfer JL, Gray RW, MacDonald SG and Bibens WT (2006). Can Pacemakers, Neurostimulators, leads, or Guide Wires be MRI Safe? Technological Concerns and Possible Resolutions. *Minimally Invasive Therapy* 15: 114-120.

Helfer, JL. MRI Safety Update: RF Induced Heating, presented at the Society for Medical Innovation and Technology Conference, (May 11-14, 2006) (25 pages).

International Search Report and Written Opinion issued by the International Search Authority for International Application PCT/US2008/003266; mail date Nov. 14, 2008.

Official Communication for U.S. Appl. No. 12/047,602 mailed Mar. 19, 2012.

U.S. Appl. No. 12/047,602, Official Communication rnaiied Feb. 27, 2013.

U.S. Appl. No. 12/047,602, Official Communication mailed Jun. 19, 2013.

Official Communication for U.S. Appl. No. 12/047,602 mailed Jan. 23, 2014.

Extended European Search Report for EP Application No. 13153989.2 mailed Feb. 12, 2014.

Extended European Search Report for EP Application No. 13151461.4 mailed Feb. 12, 2014.

* cited by examiner

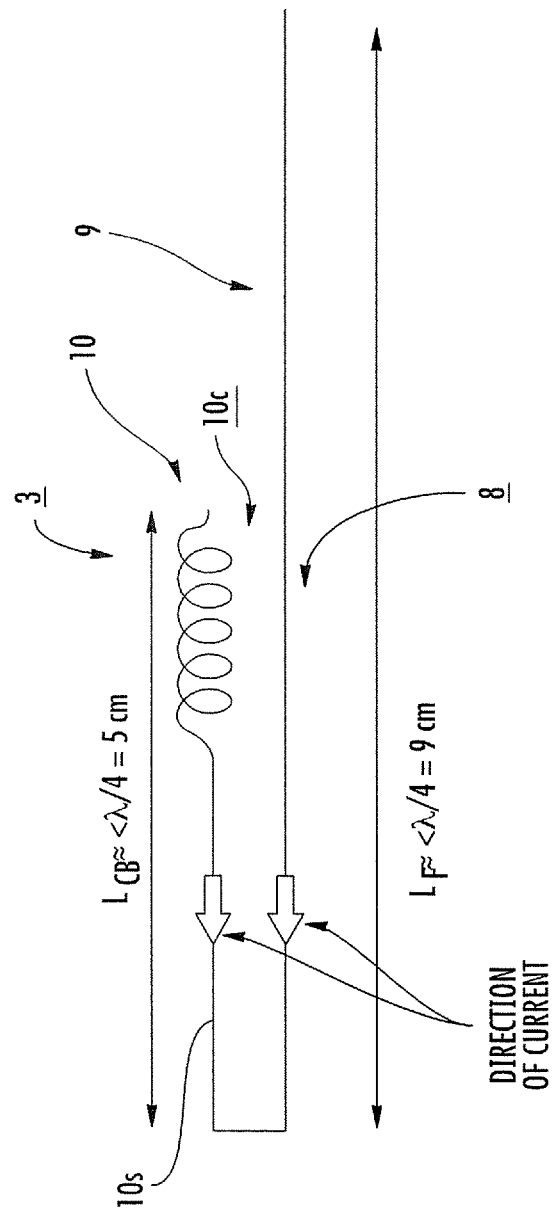

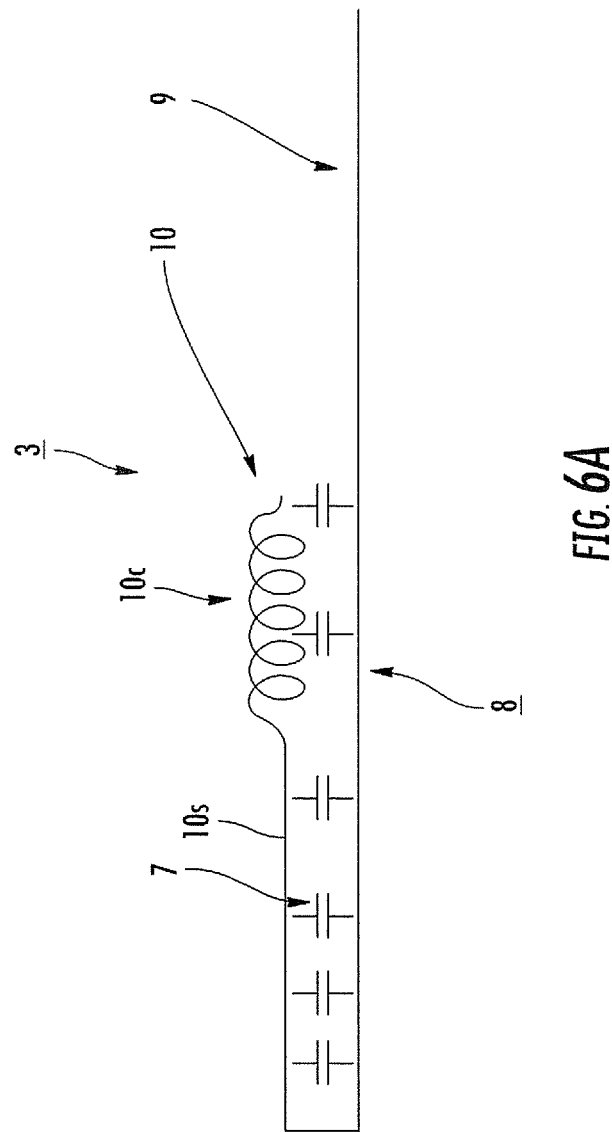

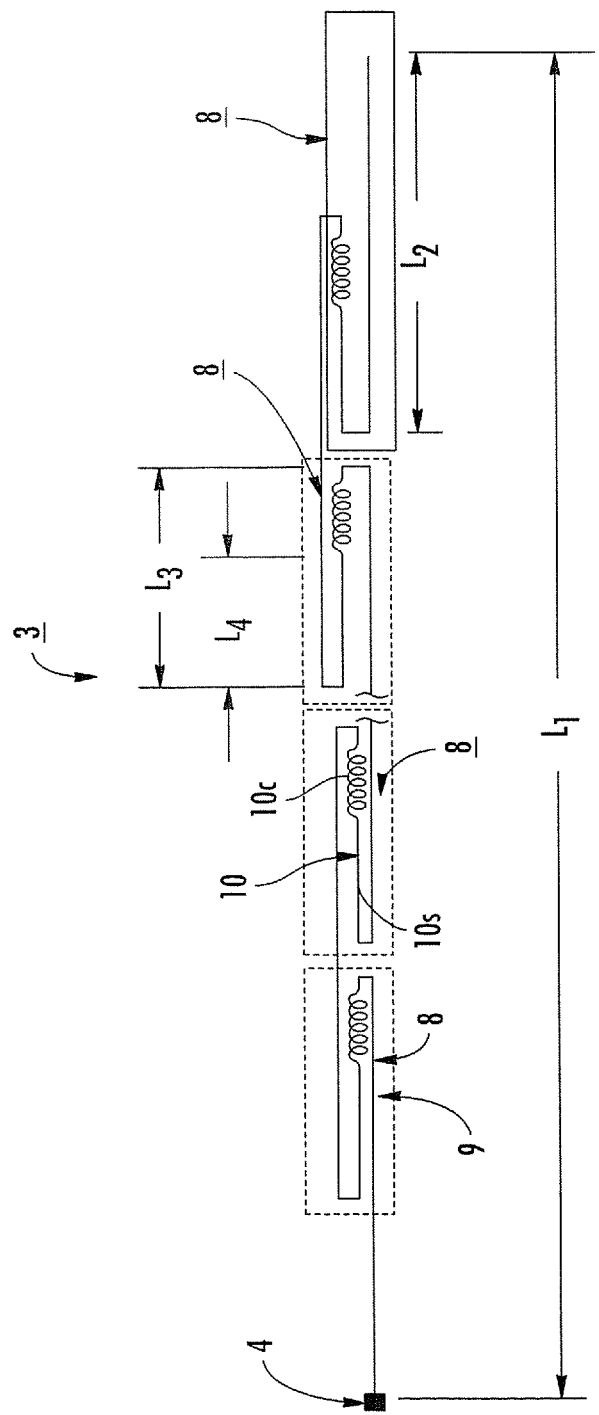

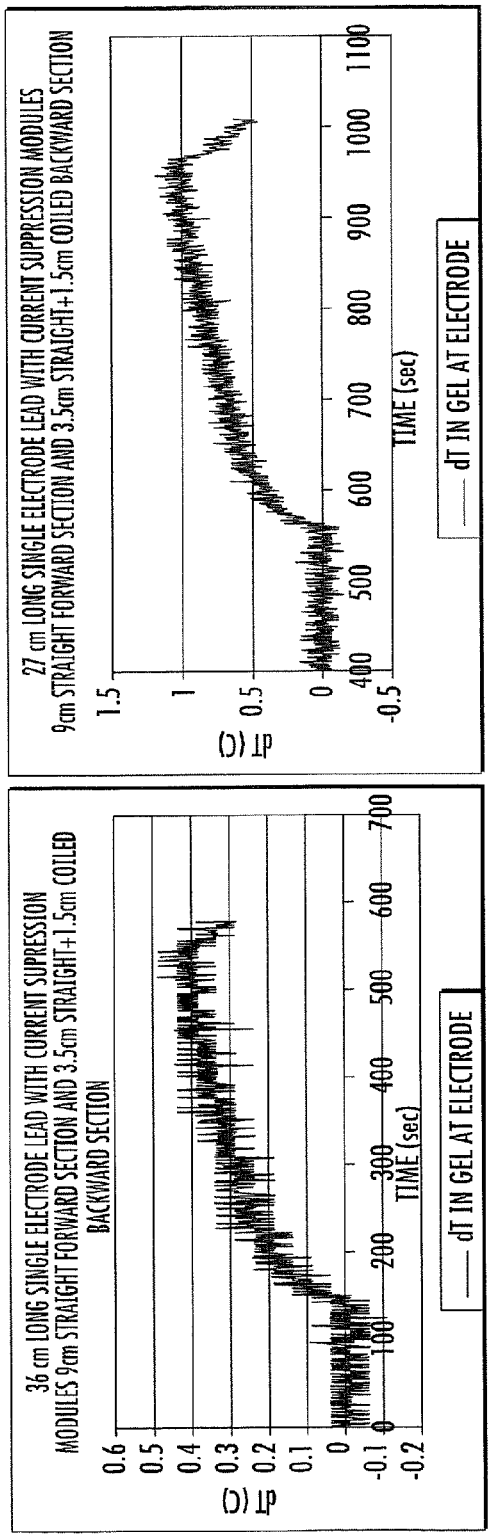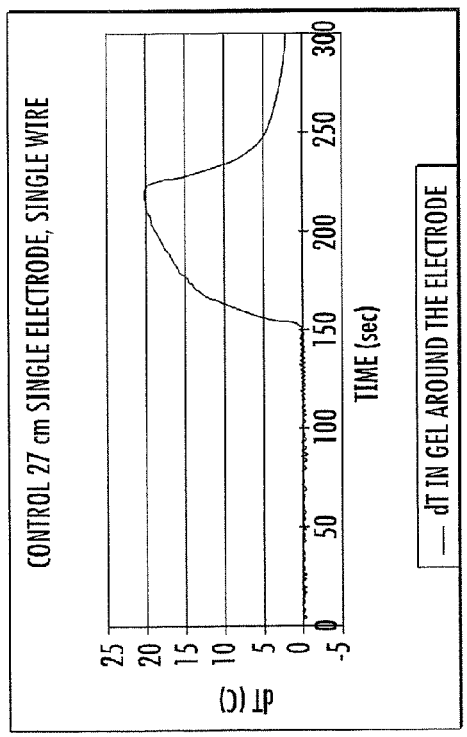
FIG. 8A
FIG. 8B
FIG. 8C

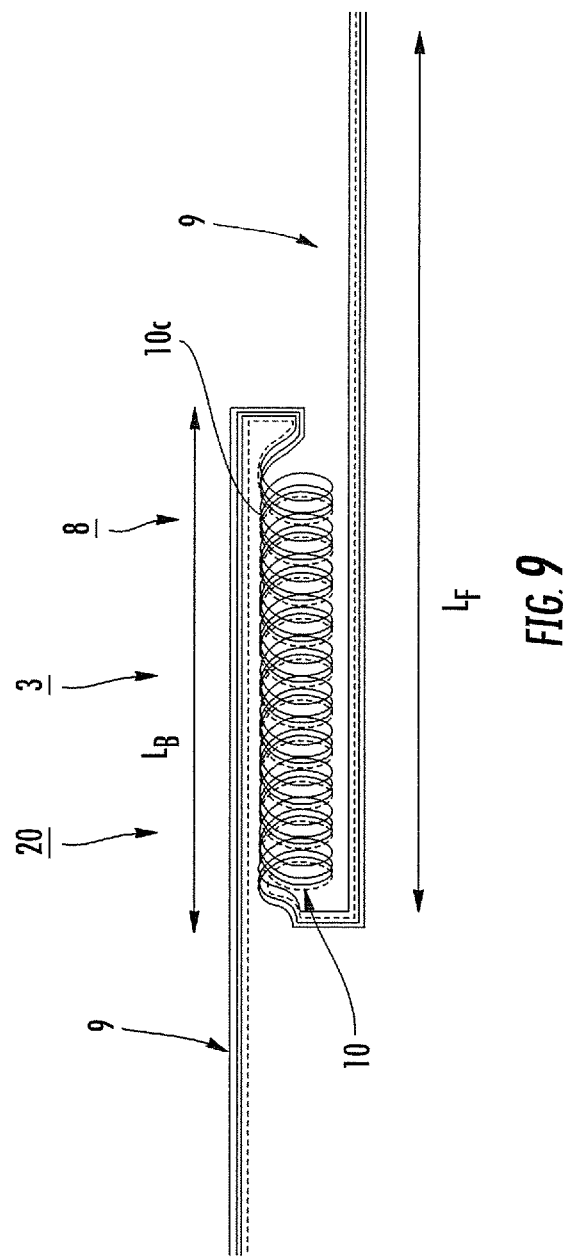

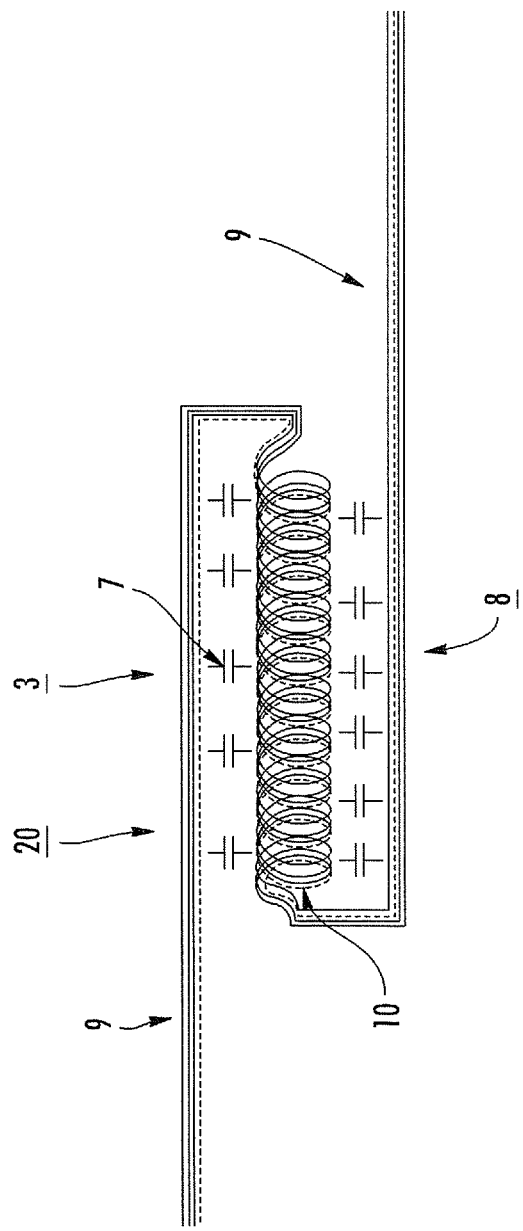

THIS IMPEDANCE IS MEASURED BY CONNECTING THE MEASURE PROBE AS SHOWN IN FIGURE BELOW.

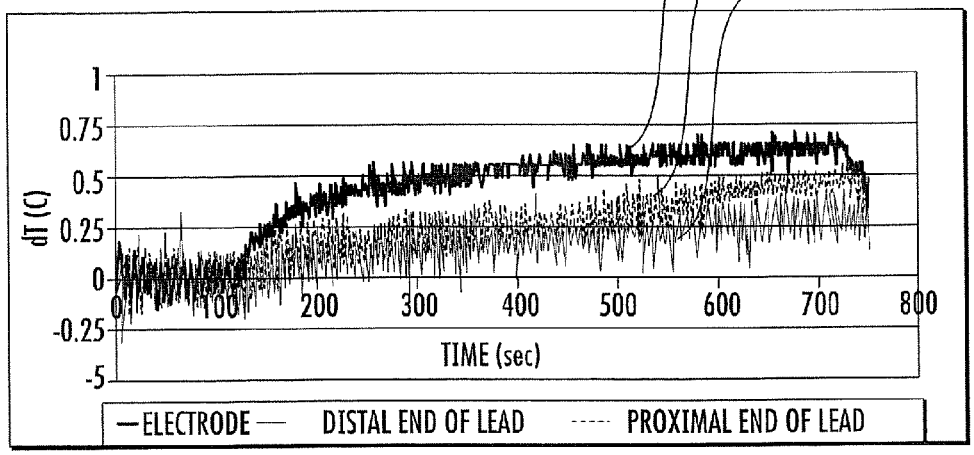
FSPGR SEQUENCE, TE=4.2, TR=17.3, BW=125, FA=170, 256=128 IMAGE MATRIX; TG=155- PEAK SAR~4.2 W/Kg
FIGURE 17: LOCAL TEMPERATURE CHANGE MEASURED AT DIFFERENT LOCATIONS ALONG THE LENTH OF A 11 CSM LEAD/PROBE IN A 1.5T MRI SCANNER.
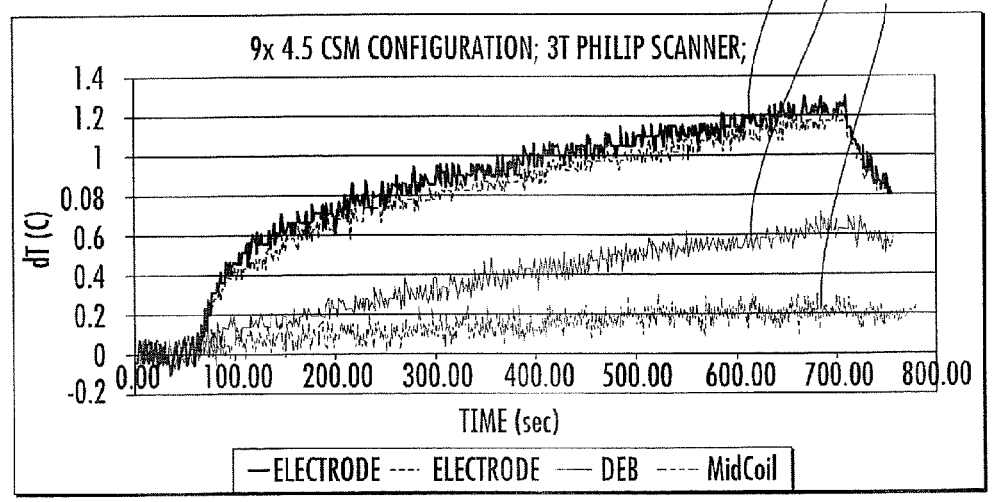
MEASURED PEAK INPUT SAR=4.2 W/Kg
FIGURE 18: LOCAL TEMPERATURE CHANGE MEASURED AT DIFFERENT LOCATIONS ALONG THE LENGTH OF A 11 CSM LEAD IN A 3T MRI SCANNER.

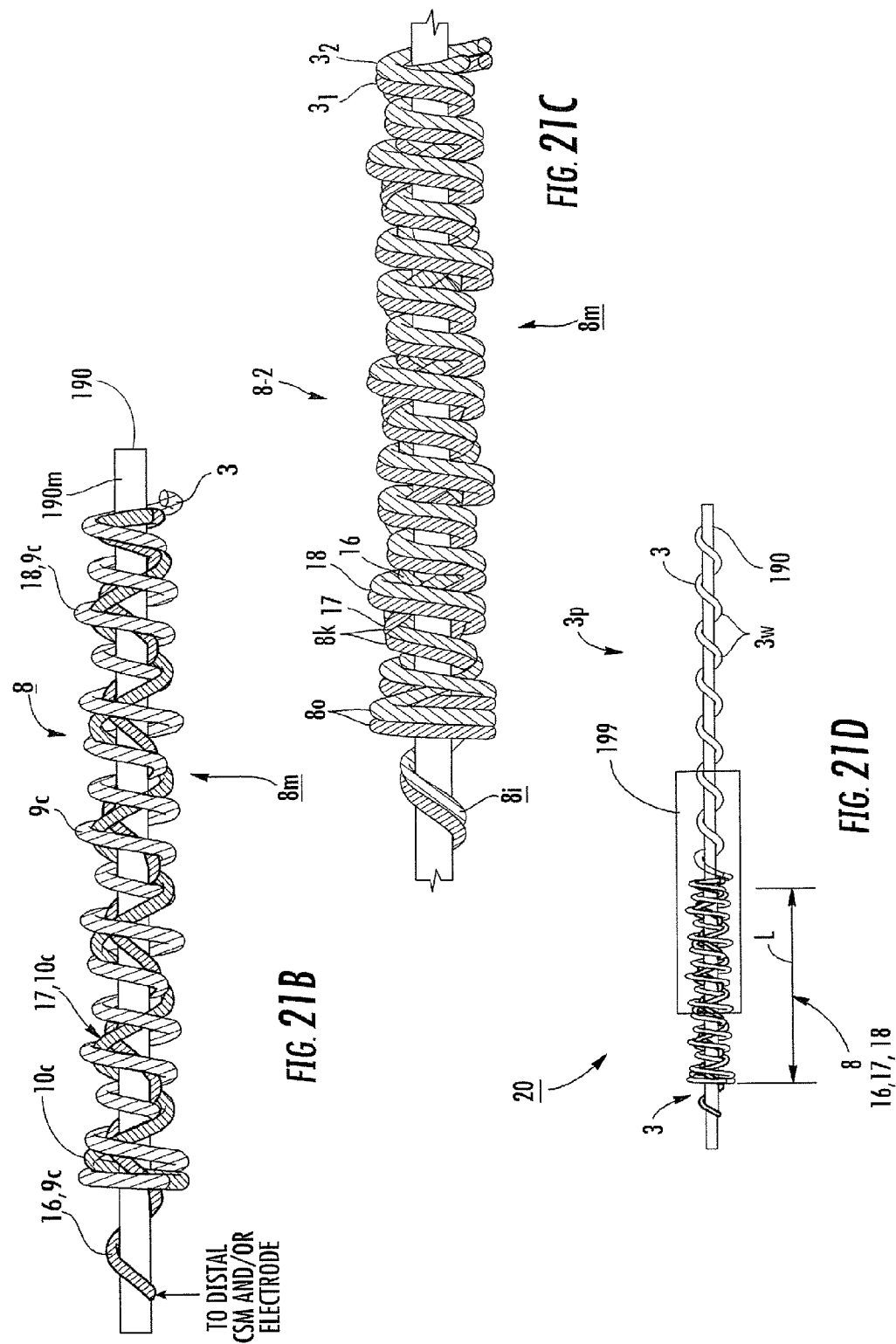

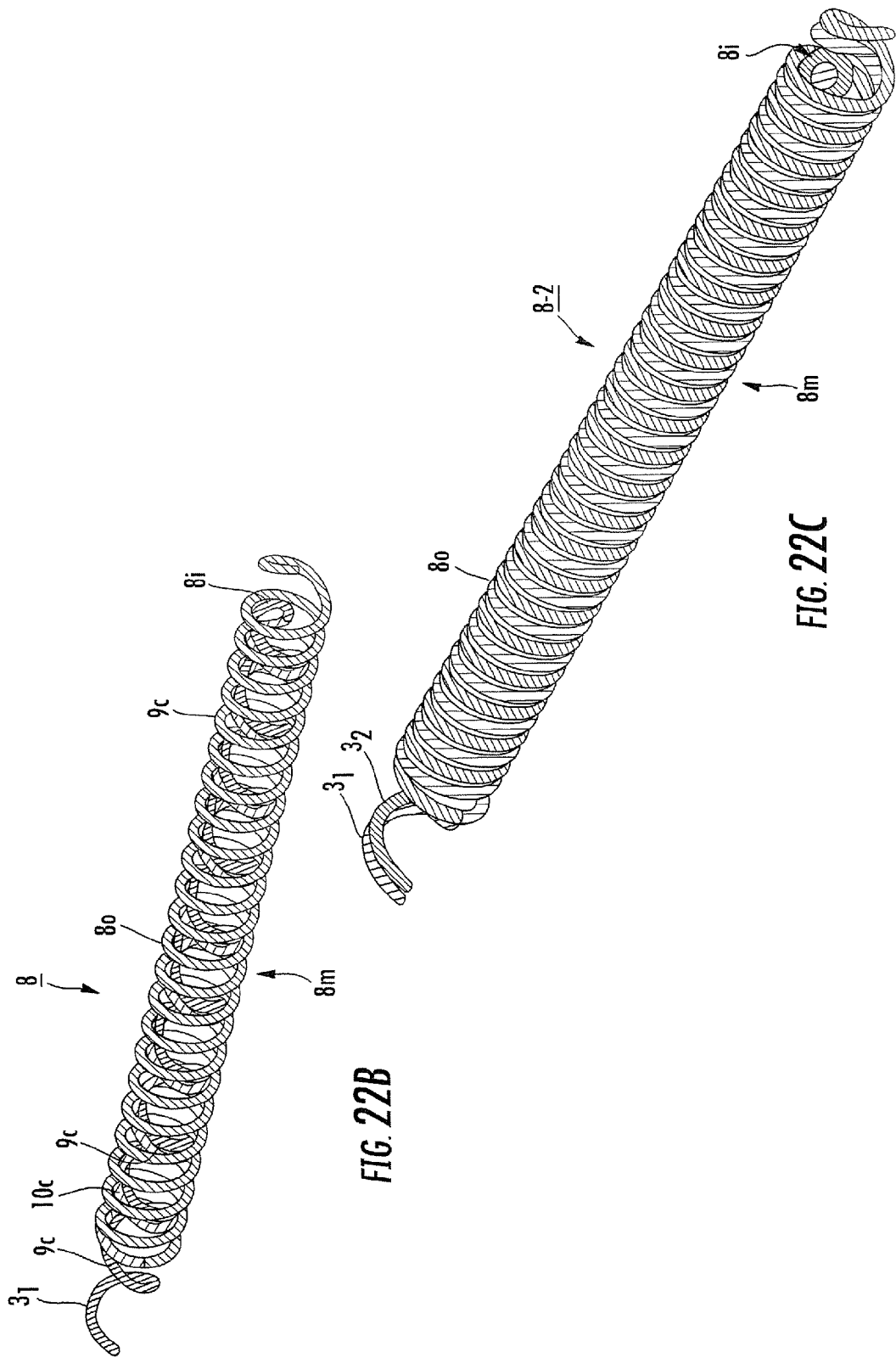

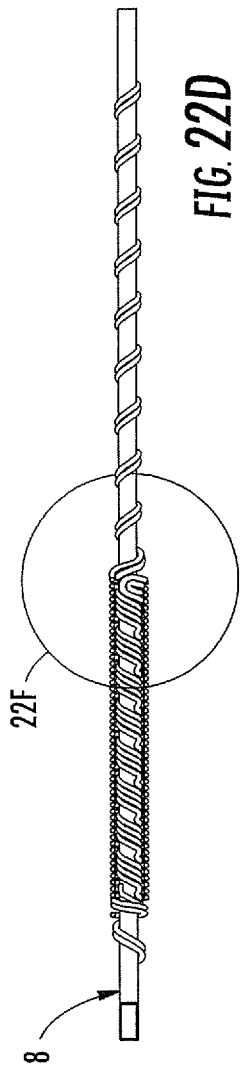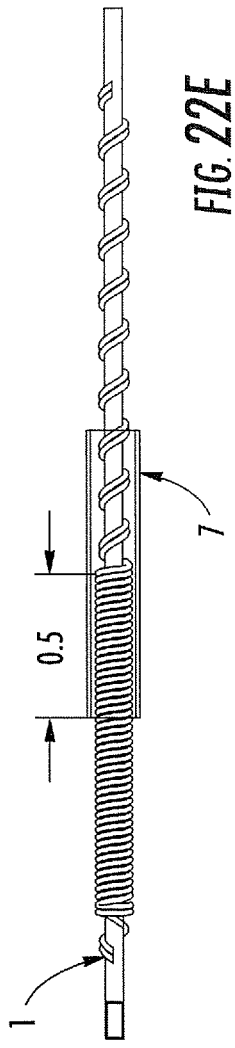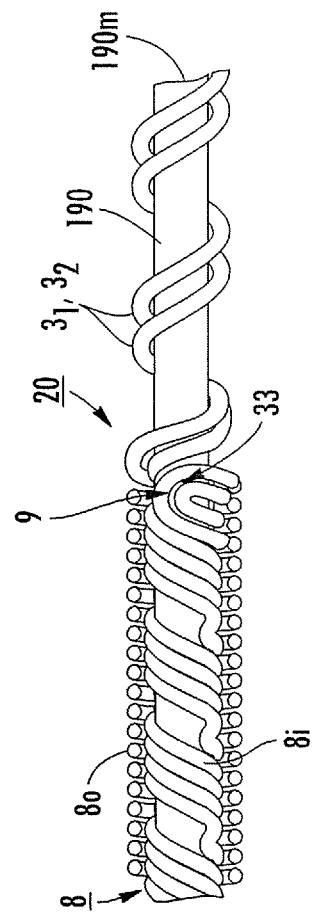
FIG. 22D
FIG. 22E
FIG. 22F

FIGURE 24A: IMPEDANCE CHARACTERISTIC OF A THREE LAYER CSM DESIGN.

IN VITRO TISSUE HEATING DATA - 2 LAYER LEAD. PEAK INPUT SAR OF THE SEQUENCE IS 4.3 W/kg

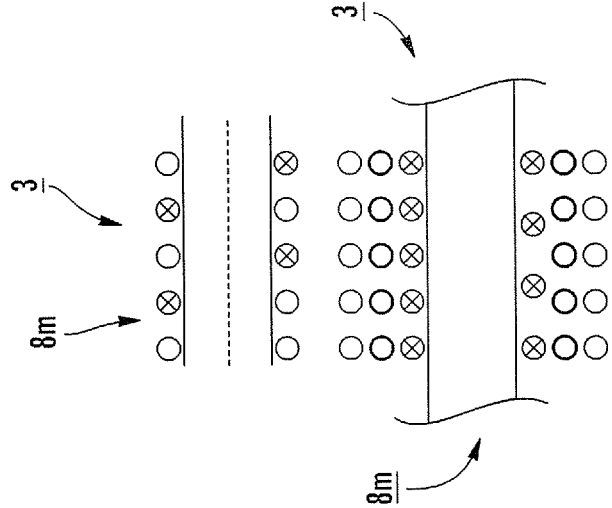

PACEMAKER AND ICD THERAPIES FOR TREATMENT OF CARDIAC ARRHYTHMIAS AND CARDIAC ARREST.

RF/MRI SAFE BRADYARRHYTHMIA
AND TACHYARRHYTHMIA LEAD SYSTEMS

□ SAFETY LINE SET SHORTER THAN CONTROLLER CABLING
▨ CONTROLLER CABLING

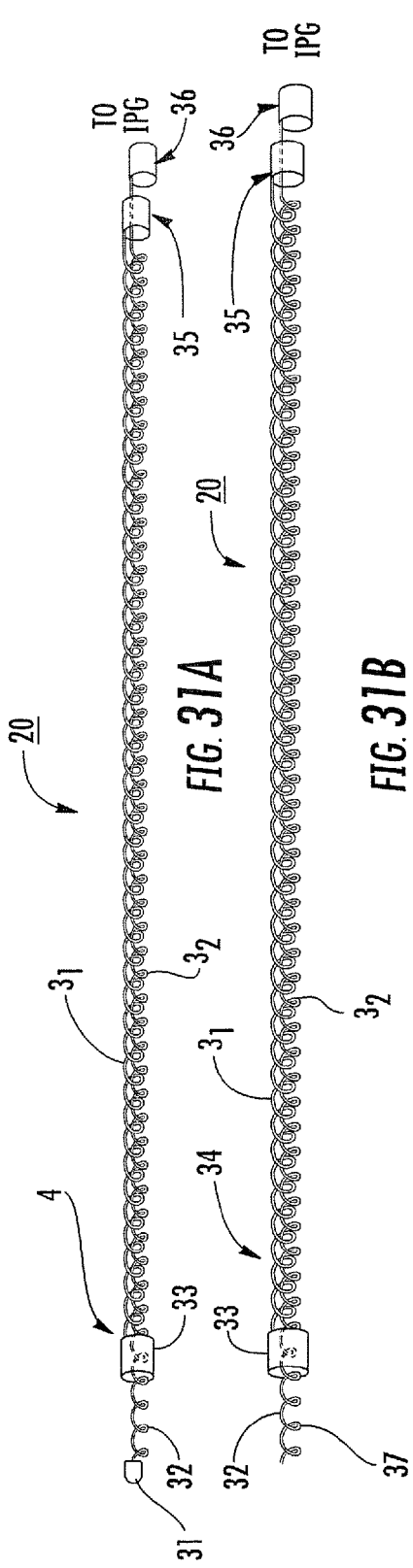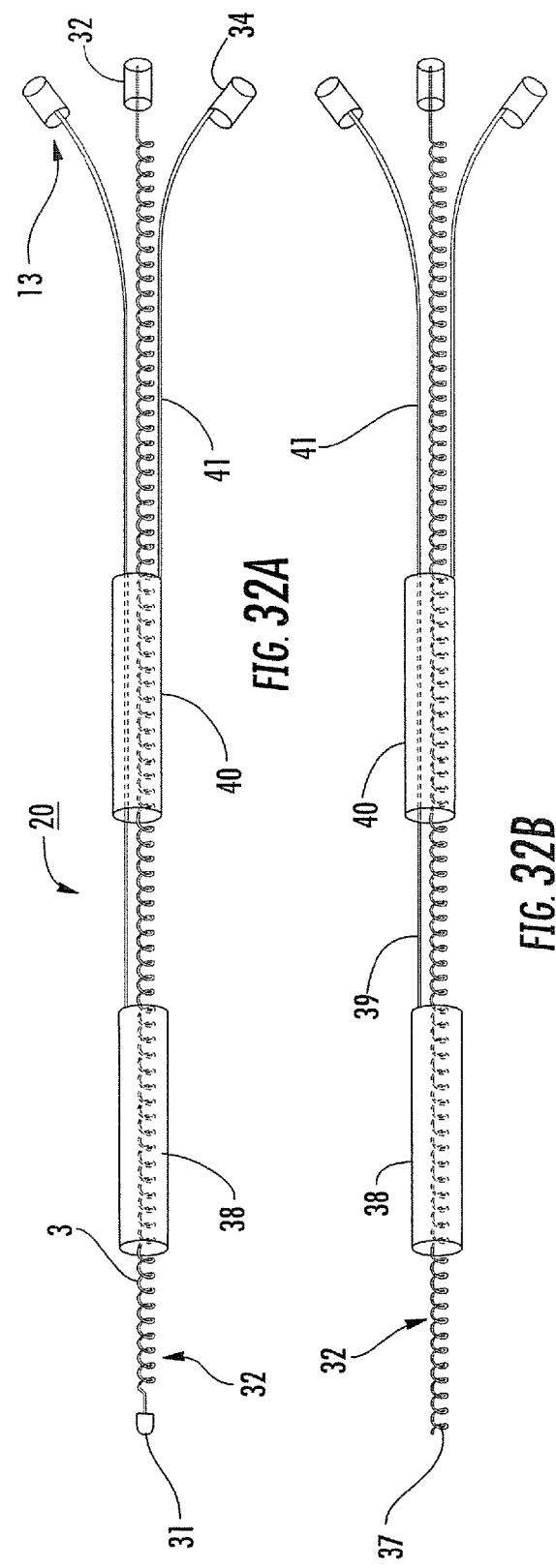
FIG. 31A
FIG. 31B
FIG. 32A
FIG. 32B

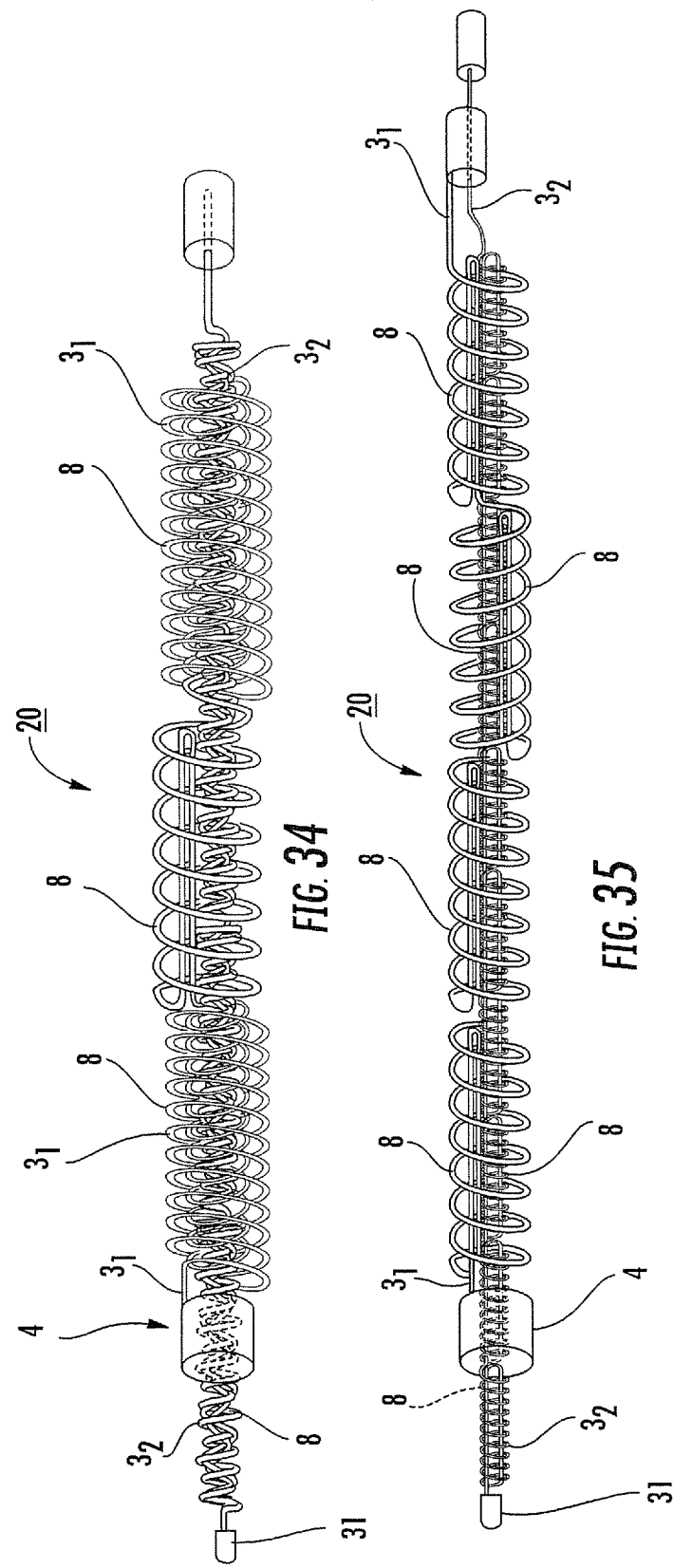

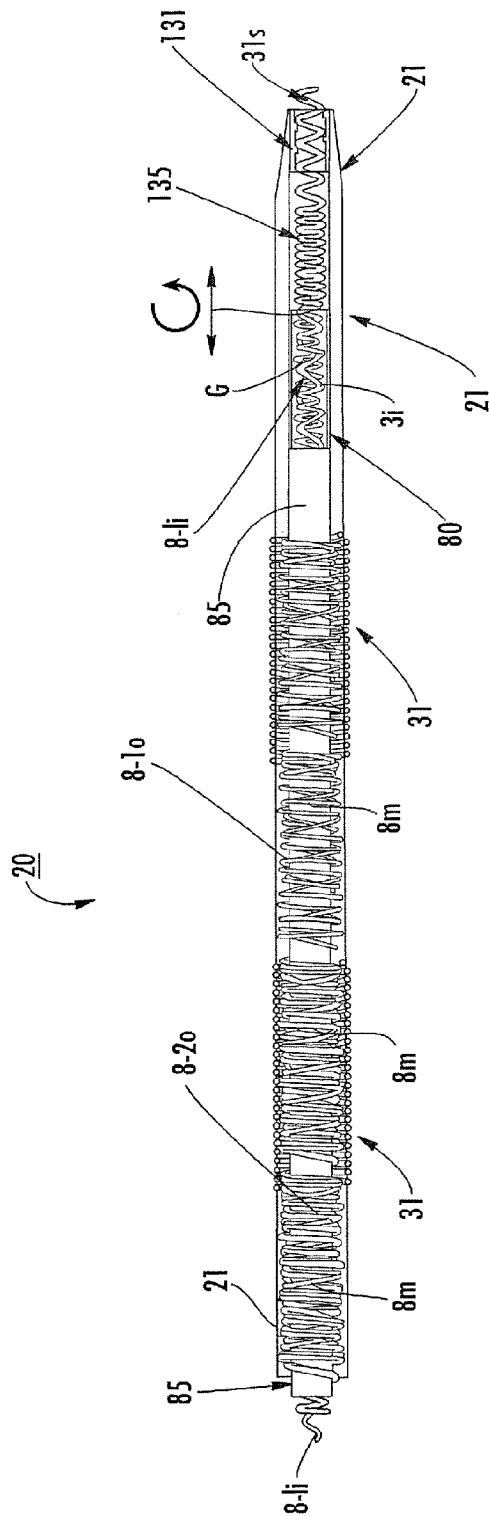
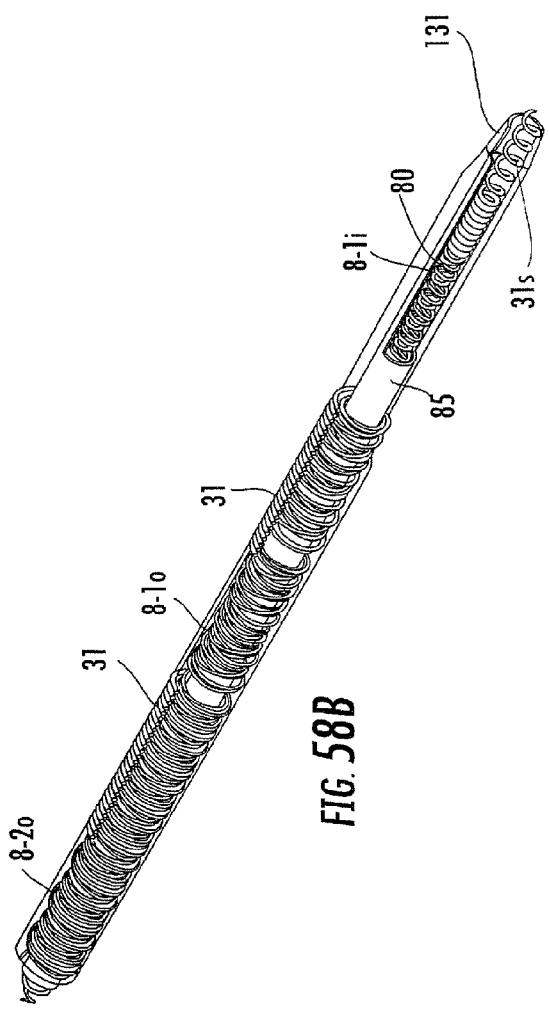
FIG. 58A
FIG. 58B

METHODS AND APPARATUS FOR FABRICATING LEADS WITH CONDUCTORS AND RELATED FLEXIBLE

RELATED APPLICATIONS

This application claims the benefit of priority of U.S. Provisional Application Ser. No. 60/895,619 filed Mar. 19, 2007, U.S. Provisional Application Ser. No. 60/912,835, filed Apr. 19, 2007, and U.S. Provisional Application Ser. No. 60/955,730, filed Aug. 14, 2007, the contents of which are hereby incorporated by reference as if recited in full herein.

FIELD OF THE INVENTION

The present invention relates to conductors and leads and may be particularly suitable for implantable medical leads.

BACKGROUND OF THE INVENTION

Linear leads comprising conductors can couple with radio frequency (RF) fields, such as those used in magnetic resonance imaging (MRI) and magnetic resonance spectroscopy (MRS). Examples of such leads include guidewires and/or interventional leads such as, for example, implantable pacemaker leads, spinal cord stimulator leads, deep brain stimulator leads, electrophysiology or other cardiac leads, leads used for implanted monitors, and leads used to administer a therapy during a surgical procedure. The coupling can sometimes result in local heating of tissue adjacent the lead(s) due to RF power deposition during the MRI/MRS procedure, potentially leading to undesired tissue damage.

MRI is a non-invasive imaging modality with excellent soft tissue contrast and functional imaging capabilities. However, MRI can be a contraindication for patients with implanted electrically conducting devices and wires, including cardiac pacemakers and/or defibrillators with leads connecting implantable pulse generators (IPGs), deep brain stimulation (DBS) electrodes, spinal cord stimulators, physiological monitors, etc. . . . , for several reasons. For example, the electronics of the IPG/ICD may fail when in presence of the high magnetic fields, or the RF used in MRI may damage the circuitry of the IPG/ICD. In addition, the implanted lead may couple to local electric fields induced in the body during transmission of RF excitation pulses whereby the lead can unduly heat tissue adjacent the lead, or may propagate the RF to electrodes at the distal end of the lead or to the device or IPG to which it is connected, potentially causing local temperature rise to unsafe levels and/or damage to the implanted device. The heating problem has been reported in the scientific literature by researchers.

For example, Luechinger et al. reported a local temperature rise of 20° C. in tissue adjacent to pacemaker leads implanted in pigs during an MRI scan. *See*, Luechinger et al. *In vivo heating of pacemaker leads during magnetic resonance imaging*, Eur Heart J 2005; 26 (4):376-383. In addition, Rezai et al. reported in vitro tissue heating in excess of 20° C. adjacent to DBS (deep brain stimulation) leads during an MRI scan. Rezai et al., *Is magnetic resonance imaging safe for patients with neurostimulation systems used for deep brain stimulation?* Neurosurgery 2005; 57 (5):1056-1062. Even external leads such as those used for measuring and monitoring physiological signals (electrocardiograms, EKG, electroencephalograms, blood pressure, sonography) during MRI may be subject to heating.

One approach to allow patients with implanted devices, such as IPGs and leads to be scanned by MRI, is the use of strictly controlled conditions that limits the input power of the MRI RF pulse sequences. This approach is reported by Gimbel et al., *strategies for the safe magnetic resonance imaging of pacemaker-dependent patients*, Pacing Clin Electrophysiol 2005; 28 (10):1041-1046, and Roguin et al., *Modern pacemaker and implantable cardioverter/defibrillator systems can be magnetic resonance imaging safe: in vitro and in vivo assessment of safety and function at 1.5 T*. Circulation 2004; 110 (5):475-482.

In other (non-MRI) uses of RF, such as where external RF electromagnetic (EM) energy is present and/or used for therapeutic purposes, external or implanted leads may also couple to the applied RF EM field and cause unsafe tissue heating or damage or destroy electronic devices that can be connected thereto. For example, RF diathermy or ablation or cauterization of tissue can sometimes employ implanted or intra-body leads that may also couple to the applied RF EM field and cause unsafe tissue heating, such as that reported for a patient undergoing RF diathermy. See, Nutt et al., *DBS and diathermy induces severe CNS damage*, Neurology 2001; 56:1384-1386; and Ruggera et al., *In Vitro assessment of tissue heating near metallic medical implants by exposure to pulsed radio frequency diathermy*, Physics in Medicine and Biology, 48 (2003) 2919-2928. Another non-MRI example of where such EM-field coupling may occur is where individuals with implanted leads are in close proximity to EM field transmitters such as RADAR, TV, wireless telephone, radio facilities, fixed or mobile. Similarly, EM-coupling may also occur with external-conducting leads connecting electronic equipment that are sensitive to intense EM fields close to intense EM field sources.

SUMMARY OF EMBODIMENTS OF THE INVENTION

Embodiments of the present invention are directed to RF/MRI compatible leads and/or conductors. The leads and/or conductors can be configured to inhibit, limit and/or prevent undesired heating of local tissue and/or the propagation of RF to an attached electronic device by the leads when exposed to certain levels of RF. Particular embodiments of the present invention are directed to flexible implantable leads with one or multiple conductors that can be safely used in an external RF field, such as those used for MRI or MRS. The configuration of the conductors can reduce unwanted coupling to RF-induced electric fields generated in the body and may reduce, minimize and/or inhibit common mode current/voltage.

In some embodiments, the leads can be configured so that RF power deposition from the leads to adjacent tissue is reduced, permitting patients implanted with such leads, to benefit from MRI/MRS under safer conditions and/or permitting the use of elongate leads, cables and the like to be used in magnet bores associated with MR Scanners during MRI guided procedures.

Some embodiments are directed to RF/MRI compatible leads that include at least one conductor having a length with opposing distal and proximal end portions. The at least one conductor has at least one segment with a multi-layer stacked coil configuration comprising a first forward coiled section that extends in a forward lengthwise direction for a first forward physical length, then turns to merge into a proximately positioned reverse coiled section that extends in a substantially opposing reverse lengthwise direction for a reverse physical length, then turns to merge into a proximately positioned second forward coiled section that extends in the forward lengthwise direction for a second forward physical length.

In some embodiments, at least two of the first forward section, the second forward section, and the reverse coiled section can have substantially constant diameter coil configurations. In some embodiments, the first forward coiled section, the second forward coiled section and the reverse coiled section can be substantially concentric.

In some embodiments, at least some revolutions of the forward and reverse coiled sections reside proximate each other in a side-to-side lengthwise orientation. In some embodiments, alternatively or additionally, at least some revolutions of the reverse coiled section reside proximate and over the first forward coiled section.

In some embodiments, at least some revolutions of the reverse coiled section are interleaved with at least some revolutions of at least one of the forward coiled sections. The forward coiled section may extend in the lengthwise direction about a central axis and have a pitch such that serial revolutions of the forward coiled section are spaced apart in a lengthwise direction to define gaps, and the reverse coiled section can extend about the central axis and have a pitch such that revolutions thereof substantially reside in the gaps of the forward coiled section. The second forward coiled section can have more revolutions than that of the first forward and the reverse coiled section.

In some embodiments, the first forward coiled section resides on a first layer, the reverse coiled layer resides on a second layer over the first layer, and the second forward coiled section resides on a third layer over the second layer to define a three-layer stacked conductor coil configuration.

In some embodiments, the first coiled forward section and the reverse coiled section reside on a substantially common layer and the second coiled forward section resides over the first forward and reverse coiled sections to define a two-layer stacked conductor coil configuration.

In some embodiments, the first coiled forward section and the reverse coiled section have substantially the same pitch and the second forward coiled section has a smaller (closer) pitch than that of the first and reverse coiled sections.

In some embodiments, the at least one conductor is a plurality of conductors, each having at least one segment with a multi-layer stacked coil configuration of at least one set of the first and second forward coiled sections and the reverse coiled section.

Some embodiments are directed at methods of fabricating a lead which may be particularly suitable as a medical lead. The methods include: (a) winding at least one conductor about a mandrel in a forward lengthwise direction to form a forward coil; then (b) winding the at least one conductor over the mandrel in a reverse lengthwise direction to form a reverse coil.

The method can optionally include providing a sleeve over the mandrel before the winding steps. The method can include automatically repeating the winding steps to create back and forth coiled conductor segments to form between about 2-100 stacked coil configurations for a respective conductor.

The method may include, after the step of winding the at least one conductor to form the reverse coil, winding the at least one conductor over the mandrel in the forward lengthwise direction again to: (a) form an upper layer forward coil over the forward and reverse coils; and (b) form a lower layer of another forward coil upstream of the first forward and reverse coils. The winding steps can be repeated to form the conductor into multiple layers of stacked coils along its length.

Other embodiments are directed to an electrical lead subassembly that includes at least one conductor comprising at least one spiral line of flexible material over an outer surface thereof.

Still other embodiments are directed to MRI/RF compatible medical leads that include at least one continuous conductor, a respective conductor having at least one segment with a plurality of closely spaced substantially concentric coils that are arranged so that at least some revolutions of one coil reside over at least some revolutions of another coil. The lead can include at least two conductors, one conductor having the at least one segment of coils is in communication with a first electrode and another conductor having the at least one segment of coils is in communication with another electrode (or each conductor can be in communication with the same electrode).

Yet other embodiments are directed to flexible medical leads having at least one conductor with at least one multi-layer stacked coil configuration with the conductor turning back on itself in a lengthwise direction at least twice in the stacked coil configuration. The at least one conductor merges at a distal end portion thereof into a forward coil section that connects to an electrode.

The lead can be any type of medical lead, interventional or implantable or external, including for example, a cardiac lead, an implantable cardiac lead, a neuromodulation lead, an implantable deep brain stimulation lead, a spinal cord stimulation lead and an interventional cardiac electrophysiology lead (for ablation).

Still other embodiments are directed to medical leads having a plurality of conductors. At least some of the conductors have a multi-layer stacked cowound coil configuration that each include a first forward coiled section that extends in a forward lengthwise direction for a first forward physical length, that then turns in a lengthwise direction to merge into a proximately positioned reverse coiled section that extends in a substantially opposing reverse lengthwise direction for a reverse physical length, and that then turns in the lengthwise direction to merge into a proximately positioned second forward coiled section that extends in the forward lengthwise direction.

The lead can be configures so that at least two of the cowound conductors connect to a single electrode or so that a respective conductor connects to different electrodes or combinations thereof.

Yet other embodiments are directed to active fixation cardiac leads that include at least one conductor having at least one multi-layer stacked coil configuration whereby the conductor turns in a longitudinal direction on itself at least twice in communication with a screw electrode. The screw electrode can be advanced to engage local tissue.

The leads may be configured so that the lead heats local tissue less than about 10 degrees Celsius, typically about 5 degrees Celsius or less, or does not heat local tissue when a patient is exposed to target RF frequencies at an input SAR of at least about 4 W/kg (peak) and/or whole body average SAR of about 2 W/kg.

In some embodiments, the lead can heat local tissue less than about 2 degrees Celsius when exposed to target RF frequencies associated with MR Scanners at a peak input SAR of between about 4 W/kg and/or whole body average SAR of 2 W/kg.

In particular embodiments, the lead can be configured to heat local tissue less than about 5 degrees Celsius when exposed to target RF frequencies associated with MR Scanners at a peak input SAR of between about 4-10 W/kg and/or between about 2-5 W/kg whole body average SAR.

Other embodiments are directed to methods of molding an encasement layer onto a medical lead, including: attaching at least one spiral strip of material to an outer surface of at least one conductor; then molding an outer layer onto the conductor to form a flexible medical electrical lead.

Still other embodiments are directed to molds for an implantable medical lead. The molds include a lower member having an elongate channel and an upper member having an elongate channel sized and configured to matably attach to the lower member such that the upper and lower member channels are aligned to define a mold cavity. At least one conductor is sized and configured to reside in the mold cavity. At least one of the upper and lower members has a mold material introduction port in communication with the mold cavity and the mold is sized and configured to mold a flexible overmold layer on the at least one conductor.

Additional embodiments are directed to automated fatigue testing apparatus. The apparatus includes: (a) a wheel in communication with a linear slide defining a linear translation member; (b) a connection rod having first and second opposing end portions, the first end portion attached to the wheel; (c) an automated drive member in communication with the wheel to cause the wheel to rotate at a desired speed; (d) a slide block attached to the other end portion of the connection rod; (e) a rotating gear attached to the slide block and in communication with a rack gear; and (f) a test specimen holder in communication with the rotating gear whereby a test specimen is automatically repeatedly exposed to linear and rotational forces for a desired number of cycles or until fracture or failure of test parameters associated with fatigue of the test specimen.

The testing apparatus may be configured so that the rack gear is slidably adjustable relative to the slide block to cooperate with interchangeable different size diameter rotating gears to adjust rotational forces on the test specimen.

The testing apparatus can be configured so that the rotating wheel includes a plurality of circumferentially spaced apart mounting pin apertures located at different radial positions from a center of the rotating wheel. The connection rod can be attached to a mounting pin at the first end portion thereof that resides in a selected one of the apertures to allow for linear movement adjustment of the slide block.

Other systems, devices, and/or methods according to embodiments of the invention will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

These and other features of the present invention will be more readily understood from the following detailed description of exemplary embodiments thereof when read in conjunction with the accompanying drawings, in which:

FIG. 5 is a schematic illustration of a single conductor having a forward and reverse segment according to embodiments of the present invention.

FIG. 6A is a schematic illustration of a single conductor having forward and reverse segments that may be capacitively coupled according to embodiments of the present invention.

FIG. 7 is a schematic illustration of a lead with a conductor and electrode, with the conductor having a plurality of forward and reverse segments spaced apart in a lengthwise direction according to embodiments of the present invention.

FIGS. 8A-8C are graphs of temperature Celsius (C) change versus time (seconds) for different lead/conductor configurations (FIG. 8C is a control wire) according to embodiments of the present invention.

FIG. 9 is a schematic illustration of a lead with multiple closely spaced conductors, the conductors having reverse and forward segments according to embodiments of the invention.

FIG. 10 is a schematic illustration of the lead shown in FIG. 9 illustrating that the lead may also include capacitive coupling between the reverse segment and one or more of the forward segments according to embodiments of the present invention.

FIGS. 17 and 18 are graphs of temperature change (C) versus time (seconds) of exemplary leads in an MRI Scanner for a 1.5 T MRI scanner and a 3.0 T MRI scanner, respectively.

FIGS. 21B and 21C are side views of stacked tri-layer conductor configurations. FIG. 21B illustrates a single conductor configuration and FIG. 21C illustrates two co-wound conductors according to embodiments of the present invention.

FIG. 21D is a partial side view of a proximal (or distal) end portion of a lead according to embodiments of the present invention.

FIGS. 22B and 22C are side views of a two-layer stacked conductor configurations. FIG. 22B illustrates a single conductor two-layer stacked configuration and FIG. 22C illustrates two co-wound conductors with a two-layer stacked configuration according to embodiments of the present invention.

FIG. 22D is a side view of a two-layer stacked two-conductor CSM lead configuration according to embodiments of the present invention.

FIG. 22E is a side view of the device shown in FIG. 22D with the addition of a sleeve placed over the CSM according to embodiments of the present invention.

FIG. 22F is a partial exploded view of the device shown in FIG. 22E illustrating a winding-direction transition zone where the lead goes from CW to CCW (or the reverse) according to embodiments of the present invention.

FIG. 25A corresponds to the lead with the tri-layer CSM configuration and two electrodes in a gel phantom for the RF pulse sequence generating a peak input SAR of 4.3 W/kg in a 3 T MR Scanner. FIG. 25B corresponds to the lead in gel phantom in a 1.5 T MR Scanner at a peak SAR of 4.3 W/Kg.

FIGS. 28A and 28B are schematic side sectional views of a conductor with multi-layer coiled CSM configurations. FIG. 28A corresponds to the first layer of the single conductor of a two-layer (double stack) configuration such as that shown in FIG. 22A. FIG. 28B corresponds to the three separate conductor layers of a three-layer configuration such as shown in FIG. 21A.

FIG. 29B also illustrates an outer layer on the lead to provide a substantially constant outer diameter lead according to embodiments of the present invention.

FIG. 29D also illustrates an outer layer on the lead to provide a substantially constant outer diameter lead according to embodiments of the present invention.

FIG. 30B illustrates the system can include two leads, extending to the RA and RV, respectively, while FIG. 30C illustrates that the cardiac system can have three leads (one each in the RV, RA and LV).

FIGS. 31A, 31B, 32A and 32B are schematic illustrations of leads which may be particularly suitable for bradyarrythmia and tachyarrhythmia lead systems according to embodiments of the present invention.

FIGS. 34 and 35 are schematic illustrations of multi-conductor leads with each conductor having multiple current suppression modules according to some embodiments of the present invention.

FIG. 58A is a side view of a portion of a lead that may be suitable to be an active fixation ICD lead according to embodiments of the present invention.

FIG. 58B is a side perspective view of the lead shown in FIG. 58A.

DETAILED DESCRIPTION OF EMBODIMENTS OF THE INVENTION

Figure 1:
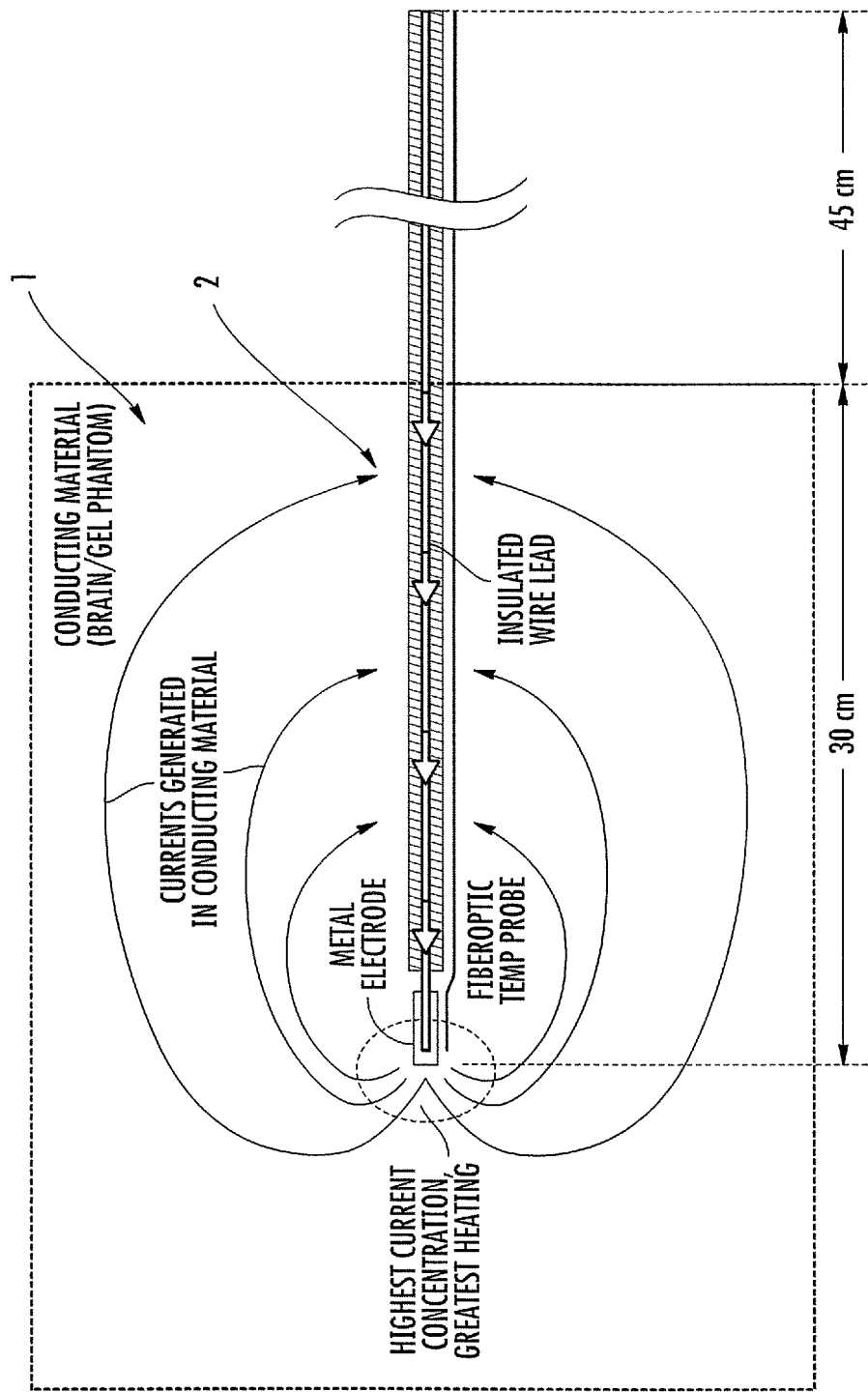
FIG. 1 is a schematic illustration of a phantom with a linear insulated wire lead and electrode.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one lead system embodiment can apply to others.

In the drawings, the thickness of lines, layers, features, components and/or regions may be exaggerated for clarity and broken lines illustrate optional features or operations, unless specified otherwise. In addition, the sequence of operations (or steps) is not limited to the order presented in the claims unless specifically indicated otherwise. It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and should not be interpreted in an idealized or overly formal sense unless expressly so defined herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/ or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

The term "lead" refers to an elongate assembly that includes one or more conductors. The lead typically connects two spaced apart components, such as, for example, a power source and/or input at one end portion and an electrode and/or sensor at another position, such as at a distal end portion or electrodes at both end portions. The lead is typically flexible. The lead can be substantially tubular with a cylindrical shape, although other shapes may be used. The lead can have a solid or hollow body and may optionally include one or more lumens. In particular embodiments, a lead can be a relatively long implantable lead having a physical length of greater than about 10 cm (up to, for example, 1 m or even longer). The term "physical length" refers to a length that and can be measured in units of length or distance, e.g., millimeters, inches and the like, and is typically constant and does not vary when exposed to different electromagnetic fields (unlike electrical wavelengths), recognizing that a physical length may shrink or expand when exposed to low or high temperatures. The lead can include at least one electrode, and in some embodiments, a plurality of electrodes (which may be both on proximal and distal end portions), and in some particular embodiments, at least one electrode can be a recording or sensing electrode or both a recording and stimulating and/or ablating electrode.

The term "conductor" and derivatives thereof refer to a conductive trace, filar, wire, cable, flex circuit or other electrically conductive member. A conductor may also be configured as a closely spaced bundle of filars or wires. The conductor can be a single continuous length. The conductor can be formed with one or more of discrete filars, wires, cables, flex circuits, bifilars, quadrafilars or other filar or trace configuration, or by plating, etching, deposition, or other fabrication methods for forming conductive electrical paths. The conductor can be insulated. The conductor can also comprise any suitable MRI-compatible (and biocompatible) material such as, for example, MP35N drawn filled tubing with a silver core and an ETFE insulation on the drawn tubing.

The term "current suppression module" ("CSM") refers to an elongate conductor that turns back on itself at least twice in a lengthwise direction to form a conductor configuration of a reverse or backward section in one lengthwise direction and proximately located forward sections that extend in the opposing lengthwise direction. The CSM can be configured with a length that is a sub-length of the overall length of the conductor, e.g., less than a minor portion of the length of the conductor and the conductor can have multiple CSMs along its length. The term "MCSM" refers to a conductor that has multiple CSMs, typically arranged at different locations along at least some, typically substantially all, of its length. The terms "backward", "rearward" and "reverse" and derivatives thereof are used interchangeably herein to refer to a lengthwise or longitudinal direction that is substantially opposite a forward lengthwise or longitudinal direction. The words "sections", "portions" and "segments" and derivatives thereof are also used interchangeably herein and refer to discrete sub-portions of a conductor or lead.

The term "MR compatible" means that the material is selected so as to be non-ferromagnetic and to not cause MR operational incompatibility, and may also be selected so as not to cause undue artifacts in MR images. The term "RF safe" means that the device, lead or probe is configured to operate within accepted heat-related safety limits when exposed to normal RF signals associated with target (RF) frequencies such as those frequencies associated with conventional MRI systems or scanners.

The term "high impedance" means an impedance that is sufficiently high to reduce, inhibit, block and/or eliminate flow of RF-induced current at a target frequency range(s). The impedance has an associated resistance and reactance as is well known to those of skill in the art. Some embodiments of the lead and/or conductors of the instant invention may provide an impedance of at least about 100 Ohms, typically between about 400 Ohms to about 600 Ohms, such as between about 450 Ohms to about 500 Ohms, while other embodiments provide an impedance of between about 500 Ohms to about 1000 Ohms or higher.

Embodiments of the invention configure leads that are safe (heat-resistant) at frequencies associated with a plurality of different conventional and future magnetic field strengths of MRI systems, such as at least two of 0.7 T, 1.0 T, 1.5 T, 2 T, 3 T, 7 T, 9 T, and the like, allow for safe use in those environments (future and reverse standard MRI Scanner system compatibility).

The term "tuned" with respect to a coil, means tuned to define a desired minimal impedance at a certain frequency band(s) such as those associated with one or more high-field MRI Scanner systems. When used with respect to a parallel resonant circuit with inductive and capacitive characteristics defined by certain components and configurations, the word "tuned" means that the circuit has a high impedance at one or more target frequencies or frequency bands, typically including one or more MRI operating frequencies.

The term "coiled segment" refers to a conductor (e.g., trace, wire or filar) that has a coiled configuration. The coil may have revolutions that have a substantially constant diameter or a varying diameter or combinations thereof. The term "co-wound segments" means that the affected conductors can be substantially concentrically coiled at the same or different radii, e.g., at the same layer or one above the other. The term "co-wound" is used to describe structure indicating that more than one conductor resides closely spaced in the lead and is not limiting to how the structure is formed (i.e., the coiled segments are not required to be wound concurrently or together, but may be so formed).

The term "revolutions" refers to the course of a conductor as it rotates about its longitudinal/lengthwise extending center axis. A conductor where coiled, can have revolutions that have a substantially constant or a varying distance from its center axis or combinations of constant and varying distances for revolutions thereof.

The term "serpentine" refers to a curvilinear shape of back and forth turns of a conductor as a subset of a length of the conductor, such as, for example, in an "s" or "z" like shape, including, but not limited to at least one flattened "s" or "z" like shape, including a connected series of "s" or "z" like shapes or with additional sub-portions of same or other curvilinear shapes to define forward and backward sections of a conductor. The upper and lower (and any intermediate) lengthwise extending segments of a serpentine shape may have substantially the same or different physical lengths.

The term "Specific Absorption Rate" (SAR) is a measure of the rate at which RF energy is absorbed by the body when exposed to radio-frequency electromagnetic fields. The SAR is a function of input power associated with a particular RF input source and the object exposed to it, and is typically measured in units of Watts per kilogram (W/kg) taken over volumes of 1 gram of tissue or averaged over ten grams of tissue or over the entire sample volume, or over the volume of the exposed portion of the sample. SAR can be expressed as a peak input and/or whole body average value. Different MRI Scanners may measure peak SAR in different ways resulting in some variation as is well known to those of skill in the art, while whole body average values are typically more consistent between different MR Scanner manufacturers.

Peak input SAR measurement is an estimate of the maximum input RF energy deposited in tissue during an MRI scan. To measure peak SAR, the following methodology using a suitable phantom can be employed. The peak SAR temperature(s) is typically measured near the surface. The phantom can be any shape, size and/or volume and is typically substantially filled with a medium simulating tissue, e.g., the medium has electrical conductivity corresponding to that of tissue—typically between about 0.1-1.0 siemens/meter. The medium can be a gel, slurry, or the like, as is well known, and has conduction and/or convective heat transfer mechanisms. Peak input SAR is estimated based on temperature rise measured by the sensors placed near the surface/sides of the phantom and is calculated by Equation 1 as stated below. See also, ASTM standard F2182-02A, which described a way to measure input SAR.

$$dT/dt = SAR/C_p \quad \text{Equation (1)}$$

where:
dT is the temperature rise
dt is the change in time
$C_p$ is the constant pressure specific heat of water (approx. 4180 J/kg-° C.).

The term "low DC resistance" refers to leads having less than about 1 Ohm/cm, typically less than about 0.7 Ohm/cm, so, for example, a 60-70 cm lead can have DC resistance that is less than 50 Ohms. In some embodiments, a lead that is 73 cm long can have a low DC resistance of about 49 Ohms. Low DC resistance can be particularly appropriate for leads that connect power sources to certain components, e.g., electrodes and IPGs for promoting low-power usage and/or longer battery life.

Figure 49:
FIG. 49 is a digital image of a flexible lead with an overmolded outer layer and the wound conductor(s) according to embodiments of the present invention.

The lead can have good flexibility and high fatigue resistance to allow for chronic implantation. For example, with respect to flexibility, the lead can easily bend over itself as shown in FIG. 49. In some embodiments, the lead, when held suspended in a medial location is sufficiently flexible so that the opposing long segments drape or droop down together (do not hold a specific configuration).

In some embodiments, the lead can be sufficiently fatigue resistant to withstand 1 million cycles of a degree of motion that includes axial rotation and lateral translation that is many times greater than that imparted to the lead in position due to human anatomy/organ movement. The stroke cycle can be carried out at rates of between about 8-9 Hz (which is relatively fast compared to an average, resting human heartbeat rate of about 1 Hz). To be considered sufficiently fatigue resistant, a lead does not exhibit breakage, breakdown of insulation (insulation resistance breakdown or cracking, splitting or rupture of insulation) or short or open circuits when exposed to the test cycles. The leads can be tested submerged in a liquid (Normal saline) using a test fixture that automatically cycles a lead through a translational stroke of about 2.9 inches. This stroke was selected to greatly exceed normal anatomical motions of the intended implant or use location of the lead (e.g., a cardiac cycle for cardiac leads) or respiratory cycle for leads that reside over the pulmonary region and the like. The lead can also be configured to withstand rotation of about 180 degrees/half-cycle.

Figure 54A:
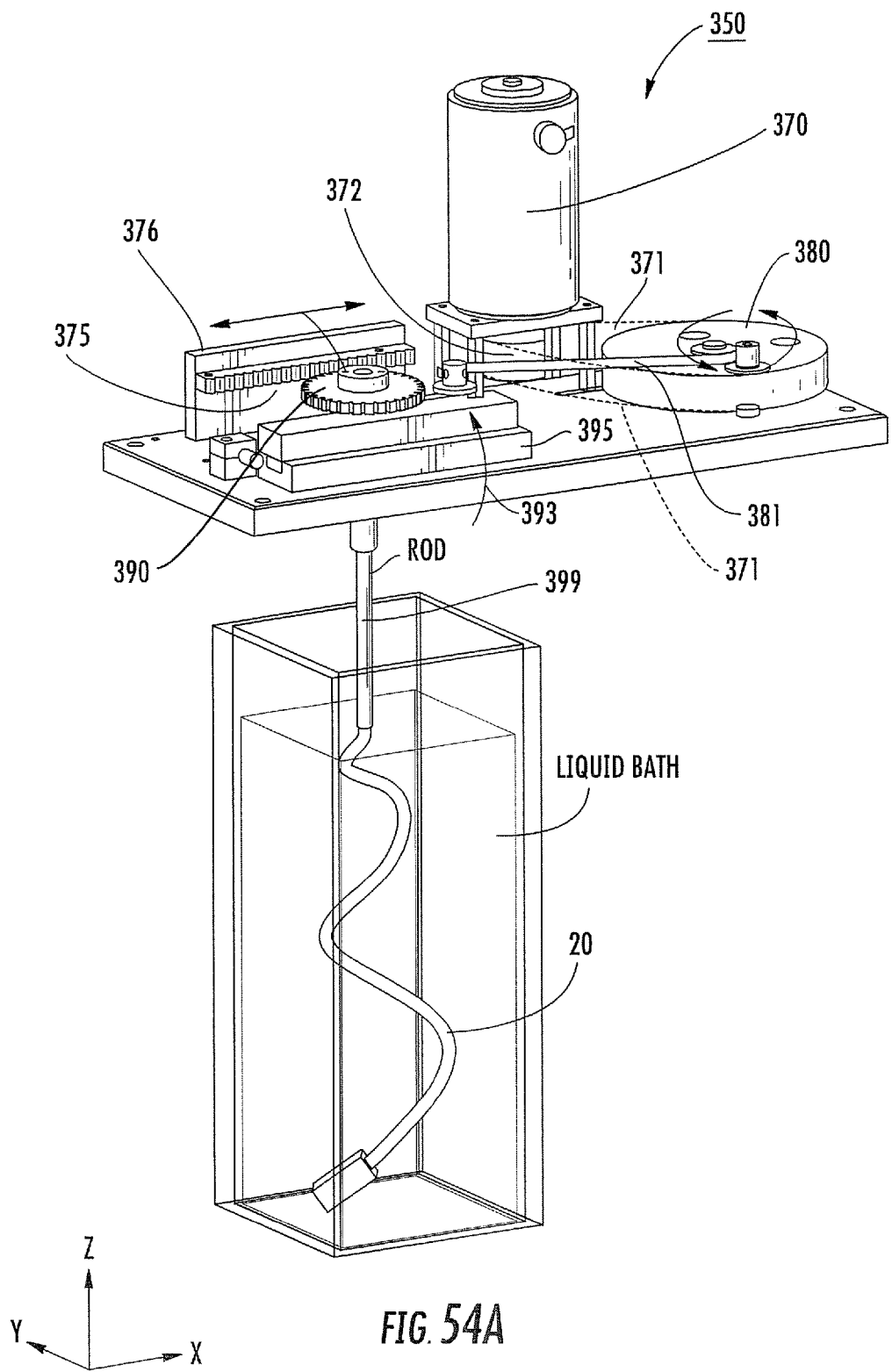
FIG. 54A is a perspective view of an example of a test fixture used to assess fatigue resistance of some lead embodiments of the present invention.

An exemplary automated test fixture 350 is shown in FIG. 54A. The test fixture 350 includes a drive system 370 that can include a motor 370 with a gear 372 that drives a belt or chain 371 that rotates wheel 380. A connecting rod 381 connects the wheel 380 to a linear slide block 393 that linearly slides over table 395. The slide block 393 is also connected to a rotational member 375 such as a gear assembly, e.g., a rotating gear 390 in communication with a stationary rack gear 376 (e.g., a rack and pinion gear assembly). In operation, the wheel 380 rotates continuously which pulls the connecting rod and the connected linear slide back and forth causing the gear 390 to rotate thus imparting linear and rotational forces on the underlying lead 20.

The lead 20 can be attached to the fixture 350 using a holder such as a lower extending rod 399 (e.g., a PEEK (poly etherether ketone) rod) that is held similar to an axle 391 in the center of the gear 390 and extends vertically down into a liquid bath (e.g., an end portion of the lead can be epoxied to or mechanically attached to the rod) so that the linear translation and rotation motion of the stroke cycle generated by the wheel 380 and rotation of gear 390 are directly imparted to the lead 20. The movement is automatically carried out using the automated drive system 370 that automatically cycles the test specimen 20 repeatedly and continuously through a stroke cycle at a desired rate/frequency.

Figure 54B:
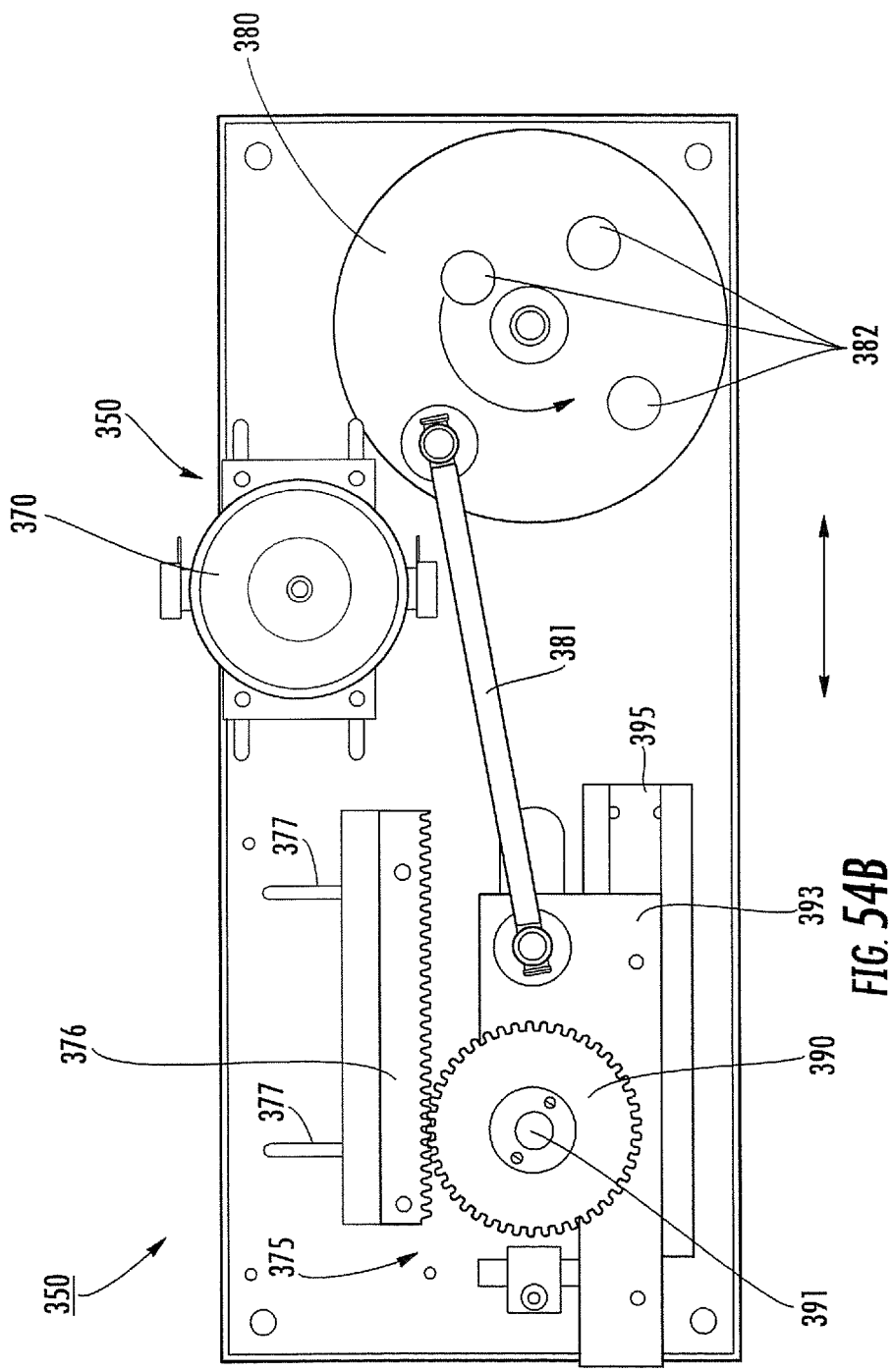
FIG. 54B is a top view of the test fixture shown in FIG. 54A.
Figure 54C:
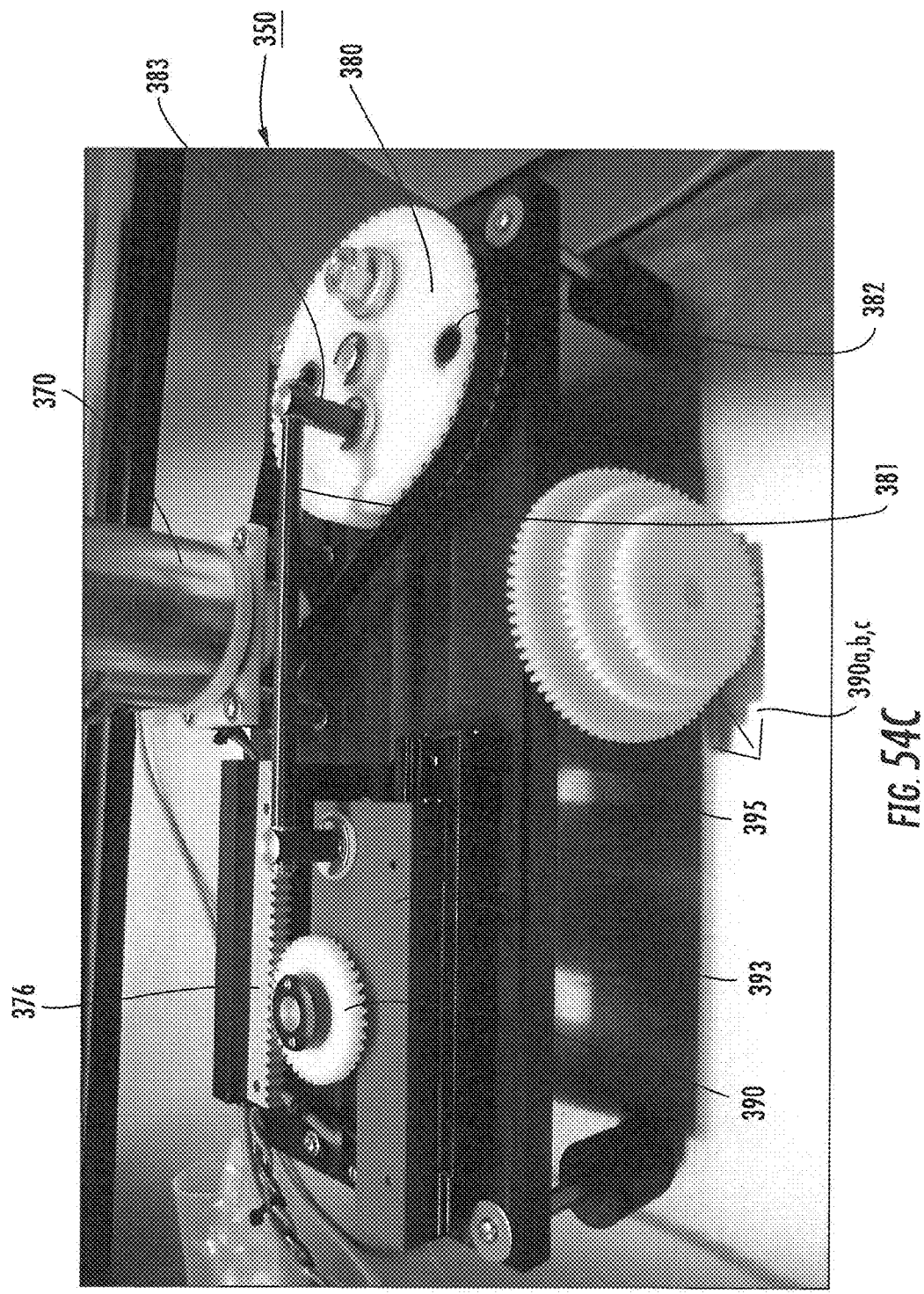
FIG. 54C is a digital photograph of a test fixture according to embodiments of the present invention.

As shown in FIG. 54A, the rod 390 is partially immersed in a temperature controlled, circulated water bath of Normal saline solution, while the lead 20 is completely immersed. The "free end" of the lead can optionally be secured with a weight to confine the motion to a region or portion of the lead. The fixture 350 can provide discrete stroke adjustments in desired increments. The wheel 380 includes several apertures 382 sized and configured to slidably receive mounting pin 383 (FIG. 54C). The apertures 382 are radially offset at different distances from the center of the wheel 380. By placing the connecting rod/crank pin 383 in a different aperture 382, the rod 381 and the slide block 393 move a different linear distance through the rotation of the wheel 380. Also, the rack 376 is held at an adjustable location in slots 377 (FIG. 54B). A different size diameter gear 390 (see, FIG. 54C, 390a, b, c) can be placed on the slide block 393 and engage the stationary gear 376 to rotate a lesser amount (a larger circumference) based on the linear movement of the slide table 393. Thus, both linear and rotational movement is easily adjusted using this fixture 350. Two embodiments of leads 20 with MCSMs formed of tri-layer stacked coils were tested with this fixture and withstood over 2 million cycles and over 15 million cycles, respectively.

As noted above, the leads may be particularly suitable for medical use, and can be used with interventional or other devices and may be acutely placed externally or in vivo or may be chronically implantable and can include one or more of a stimulating, ablating and/or recording electrode and/or sensor. The leads may be particularly suitable for implantable lead systems for IPGs, cardiac defibrillators, cardiac pacing (CP), neurostimulation or neuromodulation (peripheral, deep brain, or spinal), EP catheters, guidewires, SCS or any cable or conductors, particularly those that operate in an MR Scanner, and the like.

The leads may be implantable, MRI compatible multi-purpose lead systems with at least one stimulating/pacing electrode (in some embodiments with electrodes at both end portions) and may optionally be configured to provide an internal MRI receive antenna.

The leads may be particularly suitable as implantable or therapeutic devices for animal and/or human subjects. Thus, the leads can be sterilized and packaged for medical use. Some lead embodiments can be sized and configured for brain stimulation, typically deep brain stimulation. Some probe embodiments can be configured to stimulate a desired region of the sympathetic nerve chain. Other embodiments may be directed to other anatomical structures, organs or features including the heart. For example, the leads of the present invention may be configured for use in interventional procedures or as implantable leads for treating cardiac, gastrointestinal, urinary, spinal or other organs or body regions. In particular embodiments, the leads function as conventional pacemaker/ICD leads, i.e., leads that sense and transmit electrophysiological signals to the pacemakers/ICDs and deliver stimulation pulse from the IPG/ICD to the cardiac tissue.

While the description below is directed primarily to medical uses, the scope of the invention is not intended to be limited thereto as, in other embodiments, the leads can be configured to connect two devices and provide substantial immunity to (common mode signals induced by virtue of proximity to) an electromagnetic radiation source and/or electromagnetic fields having frequencies between about 1 MHz to at least about 1 THz, typically between 1 MHz and 1 GHz. The electromagnetic radiation source can be from RADAR, communications transmission, e.g., satellite or extra-territorial and territorial based cellular systems, television transmission, and/or radio transmission. The lead may be used as an external non-medical device. The lead may also be configured for both internal/external use or combinations thereof. For example, the lead can be configured as an implantable or interventional (acutely placed) medical lead that connects two internal devices, such as one or more electrodes to an IPG, a medical lead that connects one internal device to an external device (e.g., a therapeutic delivery device such to an external power source, control unit or supply), or an external medical lead that connects two external devices (such as a grounding pad to an RF generator for an EP (electrophysiology) ablation procedure).

Generally stated, embodiments of the invention are directed at single or multi conductor leads where the conductor(s) of the lead are arranged so as to reduce RF pickup by the lead during exposure to electromagnetic fields, such as, but not limited to, those associated with RF pulse sequences used with MRI Scanners. The conductors can be arranged in multiple CSMs along the length of the lead. In some embodiments, the CSMs can be configured to have low impedance of between, for example, 5-30 Ohms, while in other embodiments, the CSMs can have an impedance of greater than about 50 Ohms, e.g., an impedance of at least 100 Ohms, such as at least about 200 ohms, at MRI frequencies and the electrical length can be configured to be about or shorter than a quarter wavelength in a physiological medium in the electrical field. This configuration may significantly reduce coupling of the lead to the RF induced in the body during an MRI scan, and propagation of the current along the length of the lead and into the tissue adjacent to any associated electrodes that the lead may optionally have.

During an MRI scan, the patient is placed in a constant magnetic field; external RF magnetic field pulses are applied to change the orientation of the nuclear magnetism and thus obtain signal from the sample: for example, at 1.5 Tesla (T) this applied RF magnetic field has a frequency of about 64 MHz. This field is perpendicular to the MRI scanner's static magnetic fields, and is linearly or circularly polarized. The RF magnetic field can have associated with it an electric field, whose spatial distribution depends on the geometry of the MRI scanner's excitation coil and on the patient, but generally has the greatest amplitude closest to its conductors. The applied RF pulses can directly induce an electric field with an associated voltage and current in the metallic leads, implants (especially elongated ones) and conductors, consistent with Faraday's Law and Maxwell's equations, as is well known to those skilled in the field of Electricity and Magnetism. Further, the applied RF pulses generate local electric fields in the body that can be effectively focused by the presence of metallic implants and electrical leads. In both cases, any voltages and currents that are induced in the conductors of the lead may cause them to resistively heat. Leads for use with implanted devices, monitors and IPGs are typically designed for the conduction of direct current (DC) or audio frequency (AF) signals, and are typically electrically insulated along their length except for electrode contacts. However, such DC/AF insulation typically provides little or no impediment to RF signals passing between tissues and the conductors, noting for instance that insulated wires are routinely used on wires without affecting their ability to detect FM radio signals at 81-108 MHz. Thus, it is conceivable that induced voltages and currents induced in such leads or implanted devices can be deposited in the tissue adjacent to the lead, electrode(s) and implanted devices. In cases where electrode(s) have small surface contact areas with tissue, and where the electrode is at a terminal end of a lead such that the induced current and voltages are higher than on the rest of the lead, the contact tissue may present an increased risk of heating. Similarly, at terminal ends of leads that connect to implanted devices such as IPGs, excessive levels of induced currents and voltages may conceivably damage the device.

Devices incorporating designs and arrangements of conducting implantable leads according to embodiments of the invention can significantly ameliorate sensitivity to induced RF currents and RF power deposition and/or other RF or MRI based heating phenomena. These arrangements can reduce the magnitude of the induced RF current and/or voltages, thereby suppressing to a significant extent the RF power deposited on and/or associated with the lead, and consequently deposited in tissue adjacent to the lead (and electrode (s)). By this, the local temperature rise in the tissue adjacent the lead and/or electrode(s) is reduced.

Typically, as exemplified for in vivo 1.5 T and 3 T MRI results herein, the lead is able to heat local tissue less than about 10 degrees Celsius above ambient or body temperature, more typically about 5 degrees Celsius or less, when a patient is exposed to target RF frequencies at a peak SAR of at least about 4 W/kg, typically up to at least about 20 W/kg, and/or a whole body average SAR of at least about 2 W/kg, typically up to at least about 10 W/kg. In some embodiments, with a peak input SAR of between about 4 W/kg to about 12 W/kg, the lead can induce a limited increase in temperature of less than about 6 degrees Celsius, typically about 5 degrees or less, with the temperature increase at a peak SAR of about 4.3 W/kg being less than about 2 degrees Celsius so that a maximum temperature rise associated with the lead is less than about 2 degrees Celsius. In some embodiments, the lead is able to heat local tissue less than about 6 degrees Celsius when exposed to a peak SAR of between about 8 W/kg to about 12 W/kg, with the temperature increase at a peak SAR of about 8 W/kg and/or a whole body average SAR of about 4 W/kg is typically less than about 4 degrees Celsius, and, in some embodiments can be below about 1 degree Celsius.

While not wishing to be bound to any particular theory of operation, it is contemplated that embodiments of the invention can employ one or more functional underlying mechanisms incorporated by arrangements of conductors to thereby suppress and/or minimize RF coupling, induced currents, and/or RF power deposition when implemented as external, implantable or intrabody leads subjected to RF EM fields. These suppression mechanisms shall be discussed further below, in embodiments of the invention detailed herein.

As noted above, the leads can be used in several situations where individuals who have external or implanted conductors and devices may be exposed to EM fields that could induce currents in them and thereby present a safety concern or equipment malfunction, such as, for example, but not limited to, RADAR, radio, wireless (cellular) telephone or communications and TV transmission and reception installations/facilities/equipment (fixed or mobile), RF devices, as well as MRI. Without limiting the intended scope of the current invention, for illustration purposes only, the description primarily describes embodiments of the invention in the context of exposure to RF in the context of medical MRI situations, such as, for example, during an MRI guided interventional procedure or during MRI diagnostic imaging procedures.

Figure 2:
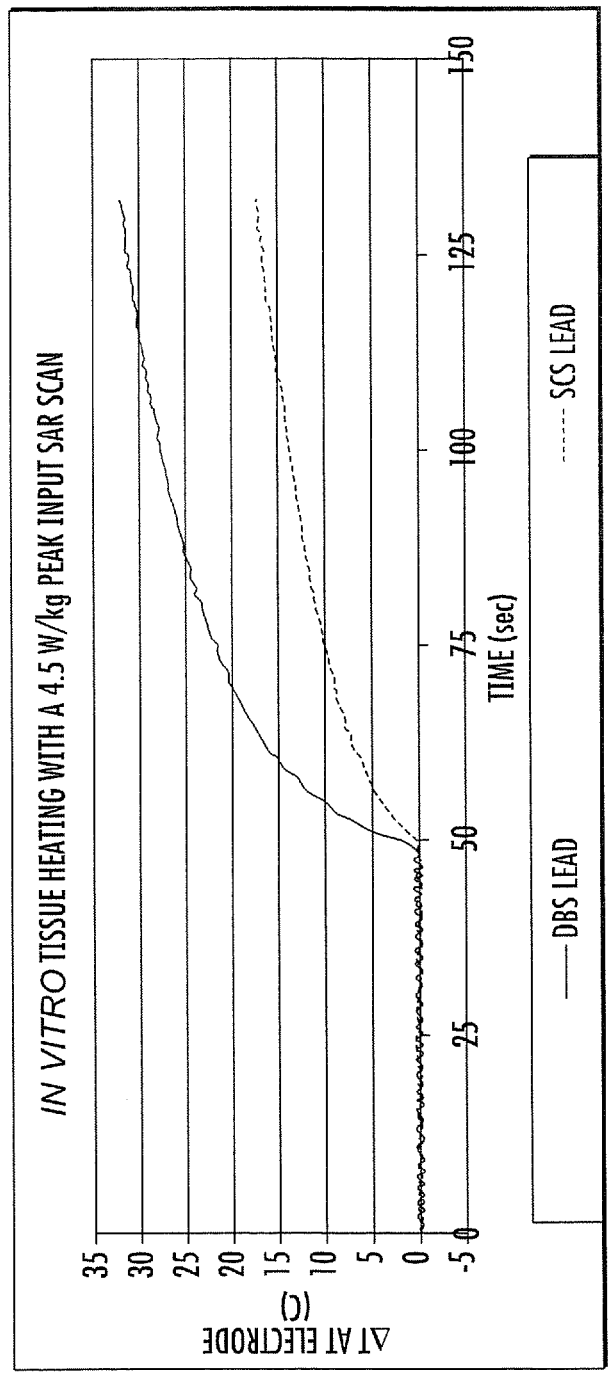
FIG. 2 is a graph of time (sec) versus temperature (C) at the electrode shown in FIG. 1 based on a 4.5 W/kg peak input SAR MRI scan.

While not wishing to be bound to any particular theory of operation, it is currently believed that when a body such as a human or animal or a biologically analogous model object ("phantom") is placed in an MRI scanner and an external RF magnetic field pulse is applied to the body to excite tissue for MRI during the scan, local electric fields ("E fields") from the excitation coil and eddy currents can be induced in the body. The magnetically induced eddy currents are in a direction orthogonal to the applied RF field and at the same frequency. Magnetic flux may also be generated. When one or more conductors are placed in the body, they can couple with the local E-fields and eddy currents can be deposited on the conductors 2 of the lead 1 as shown in FIG. 1. Because the applied excitation fields will in general be substantially uniform over the cross-sectional dimension of the one or more conductors, the coupled and induced currents in the conductors are in the same direction, and shall henceforth be termed "common mode currents". This current travels back and forth at the RF, and can cause a local temperature to rise to unsafe levels especially where currents peak at the ends, in tissue adjacent to electrodes, for example as shown in FIGS. 1 and 2. FIG. 2 illustrates temperature rise on two different leads, an SCS (spinal cord stimulation) lead and a DBS (deep brain stimulation) lead. The local temperature rise can be proportional to the total RF power deposited on the conductor, which is a function of: the applied RF field strength, frequency and duty cycle; the electrical length of the conductor in the body, which is a function of the conductor's RF impedance (its conductivity, insulation thickness and the complex impedance of the environment around the conductor); and the size and RF electrical properties of the body.

In reference now to one theory of operation with respect to the common mode currents, if two conductors (e.g., wires or filars) of substantially equal or equal electrical length (the electrical lengths and need not be the same as the respective physical lengths) are placed in the same electromagnetic (EM) fields in the same orientation, the magnitude and direction of current deposited on them will be substantially the same or the same. Now, it will be seen, in accordance with some embodiments of the present invention, that these conductors may be arranged in such a way so as to suppress (balance, offset, null, reduce and/or limit) the common mode currents by forming a conductor that turns on itself two or more times, e.g., formed into sections that include lengths whose direction is reversed in a longitudinal and/or lengthwise direction. By this configuration, it is contemplated that a reduction or a cancellation of the common mode current in an electrically equivalent forward length of conductor may be affected, thereby substantially reducing the overall current, which flows to the ends of these conductors. However, it will be appreciated that with this concept, the conductor (e.g., wire) still traverses the distance from one component to another, e.g. an electrode to an implanted device or IPG. In accordance with embodiments of the present invention, the electrical length of reversed sections are modified so as to alter their physical length, while providing a canceling, nulling or offset affect of common mode currents. The lengths of the sections are chosen based on considerations described hereinbelow, which also include factors that relate the impedance and transmission line characteristics of the conductor, and/or its EM wavelength. The reverse sections can have a physical length that is less or the same as at least one adjacent (neighboring) forward section and may have an electrical length that is less, the same or more than that of the at least one adjacent (neighboring) forward section.

Figure 3:
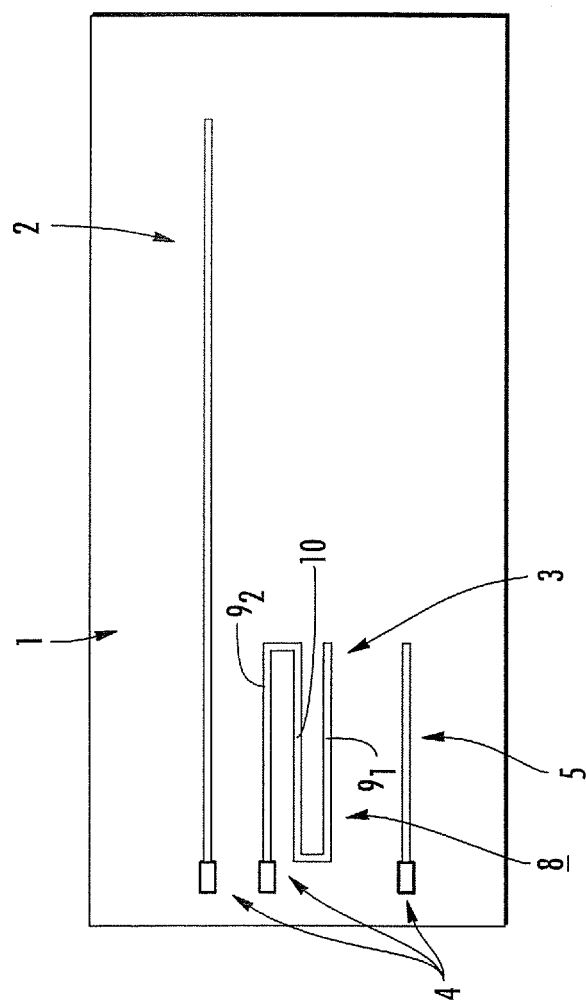
FIG. 3 is a schematic illustration of three different conductor configurations according to embodiments of the present invention.

Referring to FIG. 3, three different conductor configurations are illustrated. The top conductor 2 configuration is of a 27 cm long straight conductor. When this configuration conductor was placed in a simulated tissue gel phantom and subjected to external RF fields in a 1.5 T MRI scanner operating at about 64 MHz, a local temperature change of about 20° C. was measured in the tissue adjacent to the electrode (see, FIG. 8C). In contrast, modifying the 27 cm conductor 2 configuration as shown by conductor 3 with the conductor 3 turned upon itself (in about 9 cm sections) to define a conductor portion or segment having a BS section 10 and two FS sections 9 causes a substantially lower local temperature change, measured as less than about 1° C. during the same MRI scan carried out for conductor 2, which is similar to that seen with a conductor 5 having a 9 cm conductor as shown by the bottom conductor configuration. Conductor 5 has a physical length of about 9 cm and may have an electrical length of about λ/4 or less. The temperature reduction is believed to reflect reduced coupling to the local E-fields because of the reduced length of each section (9 cm vs. 27 cm). In the context of some particular embodiments of the invention, a common mode current may be induced in all three sections of the turned 27 cm conductor 3. However, again according to one contemplated theory of operation, the current in one forward section $9_1$ of the conductor 3 may be thought of as being canceled or reduced by the current in the reverse (backward) section 10, leaving a reduced (or net un-canceled) current in the third (9 cm) section $9_2$ consistent with this conductor 3 producing substantially the same heating as the shorter (9 cm) length conductor 5, alone. However, other or additional operational mechanisms may be responsible for the reduced heating.

As shown schematically by the lead configuration in the middle of the three leads in FIG. 3, reversing the direction of the conductor 3 appears to offer an induced current suppression mechanism that is potentially frequency non-specific and might be considered "broadband" suppression. However, in practice, several factors that are frequency dependent can be considered. In particular, at RF of about 30 MHz and higher, the length of implanted leads can become comparable to the EM wavelength of current in the leads, which generally results in modulation of the currents as a function of distance along the lead due to the EM wave, which can cause any heating that occurs in the exposed sections ($9_1$, $9_2$, and the like) to vary with position in response to variations in the current amplitude, and can thereby modulate the common-mode suppression strategy outlined above.

Accordingly it may be desirable in some embodiments of the present invention to divide the long conductors used in lead systems into a plurality of individual RF-induced current suppression modules 8 that are small compared to the wavelength. Thus, in some embodiments, each individual CSM 8 or a respective BS 10 and/or FS 9 thereof may have an electrical length that is preferably no more than about $\lambda/4$, typically shorter than $\lambda/4$, where $\lambda$ is the EM wavelength of the conductor in the body at the RF of interest (e.g., the operational frequency of the MRI scanner). Generally stated, each module 8 has at least two sections, a forward section (FS) 9 and a backward section (BS) 10. The FS 9 and BS 10 can have similar or substantially equal electrical lengths, and thus experience a similar extent of coupling to the EM fields and similar magnitudes and direction of induced common mode current when immersed in the same EM fields. According to one common mode current suppression mechanism theory, these similar magnitudes and directions of the currents induced in the forward and backward sections can be thought of as meeting each other at the ends of each section, resulting in a substantial cancellation of the current, as distinct from conventional straight leads wherein the current(s) can continue unabated and even increase, potentially causing undesired heating. Other non-equivalent electrical length configurations may be used, for example, a shorter electrical length in a FS 9 relative to a corresponding BS 10, and in the location of the BS 10 on a proximal length, or on a distal length, relative to the overall physical length of the conductor 3 (e.g., wire or filar), and/or symmetrically disposed relative to a first turn or bend in the conductor 3.

Figure 4:
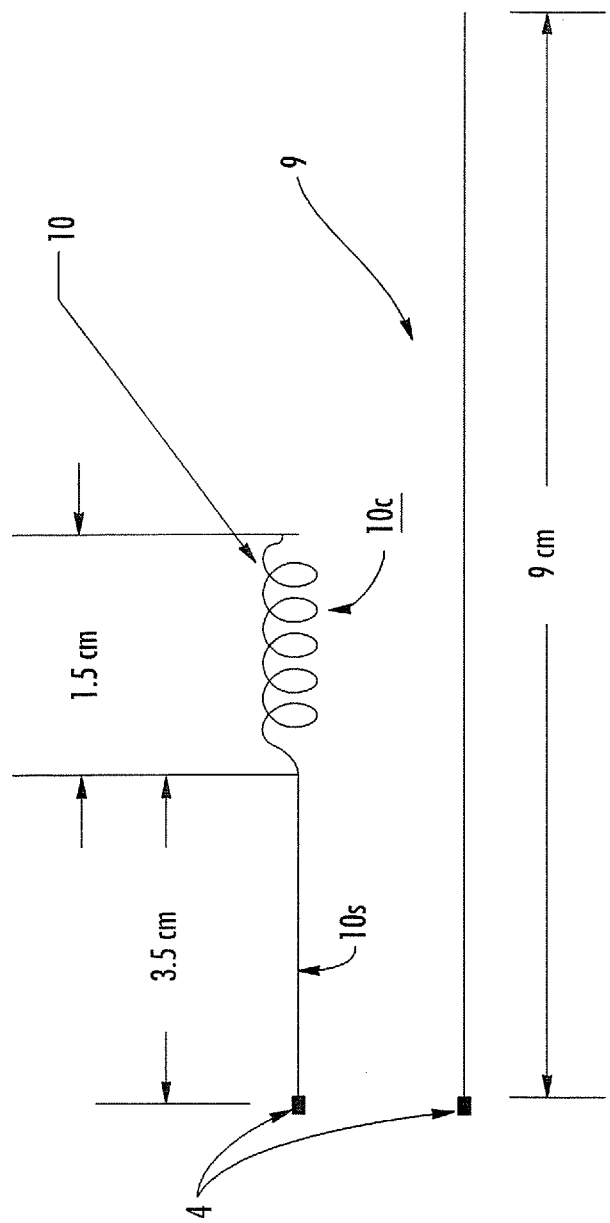
FIG. 4 is a schematic illustration of two different lead configurations according to embodiments of the present invention.

The electrical length and wavelength ($\lambda$) of a conductor is a function of its physical length, RF impedance, the insulator/dielectric material surrounding it and the electrical properties of the medium it is placed in. For example, at 64 MHz and in a saline solution (0.9%) a copper wire of the type used for winding magnetic coils ("magnet wire") 9 cm long is roughly equal to $\lambda/4$. If insulation is added to the conductor, depending on the insulation thickness and dielectric constant of the insulation, X increases, i.e., the 9 cm long conductor with insulation now has an electrical length that is shorter than $\lambda/4$. Also, coiling a length of the conductor can affect the effective physical and electrical lengths. The $\lambda/4$ length of the coil depends on the diameter of the conductor and the diameter of the coil. For example, as shown in FIG. 4, a 9 cm straight conductor (e.g., magnet wire) 9 is electrically equivalent in length to a wire 10 having a 3.5 cm straight section 10s and a 1.5 cm coil 10c formed of the conductor (e.g., magnet wire (diameter 0.040" ID)); and to a 2.5 cm of the same conductor (e.g., magnet wire) coiled 10c to an ID of 0.040" (FIG. 9). FIG. 5 illustrates that the backward section 10 has a coiled section 10c and an overall physical length "$L_{CB}$" of about 5 cm to provide substantially the same electrical length as the forward section 9, shown here with a linear (straight) length of about 9 cm.

As will be discussed further below, one or both of the FS 9 and/or BS 10 segments of each or some CSMs 8 on a lead may each be coiled or comprise coiled segments. According to embodiments of the present invention, in operation, sections 9 and 10 are subjected to the same or a similar EM field such that the common mode currents are induced in the same direction, depicted here by arrows, will provide a certain level of cancellation where the sections meet. It would appear that if sections 9 and 10 are of electrically substantially equivalent lengths, and if the EM field is the same across the lengths of both sections, then cancellation should be complete. However, it is appreciated that, in practice, current cancellation may not be 100% for various reasons, including for example variations in the coupling electric field in the two sections, but is sufficient to suppress common mode current(s) to within acceptable limits. In vitro tissue heating tests of leads configured as shown in FIG. 7 resulted in local temperature changes in the gel surrounding the test lead of ~1° C. as shown in FIGS. 8A and 8B.

In considering the mechanisms by which induced currents are ameliorated according to embodiments of the present invention, it will be recognized in addition that the FS and BS portions 9, 10 of proposed current suppression modules 8 have RF electrical impedances comprised of the total resistance of the section, and a reactive component comprised primarily of the inductance of coil portions. It will be understood by those skilled in the art that the term "coil" can include discrete circuit inductors (which are typically microwound coils; non-magnetic and MRI-compatible for MRI applications) in addition to those coils formed by the conducting leads.

Figure 6B:
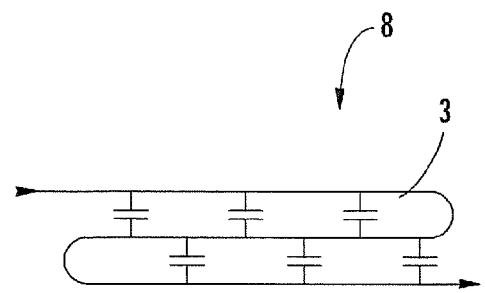
FIGS. 6B-6E are schematic illustrations of a conductor with a current suppression module of forward and reverse segments and exemplary capacitance configurations according to embodiments of the present invention.
Figure 6C:
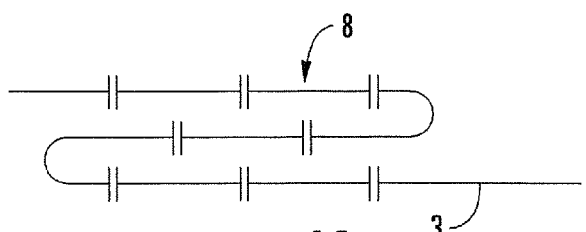
Figure 6D:
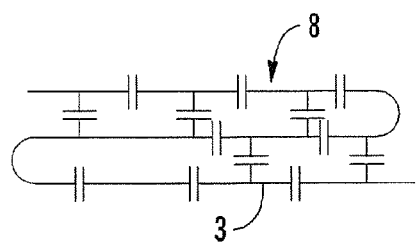
Figure 6E:
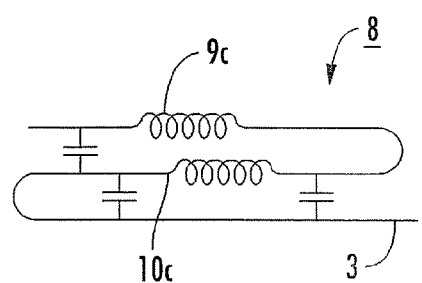

In addition, the reactive component may include parallel capacitance depicted as connecting between FSs 9 and BSs 10 and that is distributed mutually between lead sections or included as discrete components, as well as stray capacitance between the surrounding environment in which the lead is placed, as illustrated in FIG. 6A. The distributed capacitance may vary from being of negligible value to tens of pF. Discrete circuit elements (capacitances and/or inductors) may also be used in series in the lead in accordance with embodiments of the present invention. The reactance is a determinant of the EM wavelength in the sections, and their electrical lengths as discussed above. Thus, when considering the impedance properties of the modules 8, the conductor arrangements of FS 9 and BS 10 as shown in FIG. 5, may potentially be thought of as adding the benefit of a high-impedance filtering effect when the magnitude of the impedance at the RF frequency of interest is large, for example $\geq 100$ Ohms. In general, this can occur over a range of frequencies, and in addition, higher levels of filtering can be expected at certain specific frequencies where the conductor electrical lengths correspond to integral multiples of $\lambda/4$. While the latter property may be limited to a relatively narrow RF range ("narrow-band" suppression), the RF filtering may be due to the impedance of the modules that is typical of that of inductor-capacitor (LC) circuits: the impedance at a particular frequency is determined by the series inductance formed substantially by the coils incorporated into the sections, and by the parallel capacitance, which can arise between the conducting lead and the adjoining environment, including nearby conductor portions (e.g., 9 and 10).

Thus, when considering impedance effects, as exemplified in FIGS. 5, 6A-6E, 9 and 10, the substantially straight sections 9 in conjunction with the BS coiled section 10C may be thought of as forming an equivalent of an LC circuit that provides an RF filter affect. As shown schematically in FIG. 6A, the coiled section 10c can be an electrical equivalent of a series inductor and a capacitance 7 that may be created by a (insulated) coil between the straight section 9 and the coiled section 10c, insulated by a dielectric (e.g., a polymer), thus potentially creating a high impedance which suppresses induced RF currents. FIGS. 6B-6E are schematic illustrations of a conductor with a CSM 8 of forward and reverse segments 9, 10 and exemplary electrical equivalents of capacitance configurations according to embodiments of the present invention. In these embodiments, the capacitance/capacitors are used in conjunction with the inductance of the conductor (FIGS. 6B, 6C, 6D) or with one or more coiled sections (FIG. 6E) to reduce the physical length of the lead for a fixed electrical length in order to suppress common mode currents and/or to provide the a high impedance RF filtering effect. Note that of these, FIGS. 6C and 6D, may not be suitable for applications involving passage of direct currents (DC) or low frequency currents for pacemakers etc. . . . , due to the presence of the series capacitances. A purpose of the series capacitances in FIGS. 6C and 6D, can be to augment the impedance of a FS 9 to further improve the RF filter effect. The embodiment of FIG. 6E includes a coil 9c in FS 9 in addition to the one in BS 10. These coils are wound in opposite directions to each other, and may be cowound with the FS conductor 9 next to the BS conductor 10 at substantially the same coil radius, or wound one on top of the other in two or more layers, or consecutively coiled. A purpose of the added coil 9c can be to augment the impedance of a FS 9 to further improve the RF filter effect, and may be of different length, diameter, and possess a different impedance from 10c. Also, coil 9c may be formed in either or both of the upper and lower FS 9 portions. When using only a distributed capacitance, FIG. 6E, may be accomplished just by forming conductor 3 into FS coils 9c and BS coils 10c.

It will now be seen that these concepts and principles of embodiments described herein can be extended to embodiments including longer leads, multiple CSMs 8 with respective FS and BS sections 9, 10. One or more of the CSMs 8 can include BS sections 10 having coiled portions 10c and FS sections 9 having coiled portions and leads 20 can include a plurality of conductors 3, as depicted, and described in the examples presented hereinbelow.

FIG. 7 depicts a prototype single lead system that has a length $L_1$ (such as about 36 cm long) with a single electrode 4 showing four of six RF induced current suppression modules 8 each with two FSs 9 with a length $L_2$ (such as about 9 cm long) corresponding to approximately $\lambda/4$ at 64 MHz, and each with one with a BS 10 with a length $L_3$ (such as about 5 cm) including a longer straight length $L_4$ (of about a 3.5 cm) and a shorter coiled length segment (of about a 1.5 cm) 10c. In the embodiments shown, the conductor is formed from 0.007" diameter magnet wire and the coiled sections 10c have an inner diameter of 0.040". In considering the impedance of each suppression module 8, the coiled BS 10 provides the inductance, and FS 9 couples with the inductor, with the stray capacitance contributed by the electrical coupling between the FSs 9 and BSs 10 themselves and the environment. In considering the common mode induced currents in each section, since both the respective sections 9, 10 of the module 8 are in close proximity, they can couple to substantially the same local E-fields and have substantially the same direction of RF current induced in them at a given time, so that, in accordance with the above discussion, the current deposited on the forward section 9 may be thought of as being cancelled to a significant extent by the current induced in the backward section 10 at the point where the sections meet, and overall less induced current flows toward the electrode 4 and into the adjacent tissues compared to that which occurs without CSMs 8.

The prototype shown in FIG. 7, underwent in vitro tissue heating tests in a 1.5 T MRI scanner operating at 64 MHz by placing it in an gel medium having similar electrical properties as a healthy muscle (conductivity, 0.7 Siemens/m conductivity). Local temperature rise in various sections (namely in gel adjacent to electrode 4) was measured using a fiberoptic temperature measurement system. FIG. 8A illustrates the change in temperature (° C.) versus time (seq) for this lead in the gel at the electrode end, which is less than 0.5° C. In contrast, a control lead of a straight conductor of the same length in the same field displayed a 20° C. temperature rise in the gel adjacent to the electrode (FIG. 8C).

A 27 cm prototype was fabricated according to the design shown in FIG. 7, but with a reduced number of modules 8 (four versus six) with the same FS 9 and BS 10 configurations. FIG. 8B illustrates the in vitro tissue heat test data performed under the same conditions. The heating at the electrode is slightly higher for the 27 cm lead, at about 1° C., but remains within an acceptable range and greatly reduced compared to the 20° C. seen in some conventional leads (FIG. 8C).

Another embodiment of a CSM 8 in accordance with the present invention is shown in FIG. 9, which depicts a portion of the conductor 3 with a single suppression module 8 that can be used to form a four-electrode and/or four-conductor lead 20. In this case, each backward section 10 has a coiled segment 10c that runs substantially the entire length thereof, for example, about 2.5 cm, rather than about 1.5 cm, as noted above. Other lengths and coil diameters and coil sizes may also be used. As also shown, the four conductors or leads can be co-wound to provide cowound coiled sections 10c of sections 10 to counter the common mode currents. Other configurations are possible including, for example, forming the coil 10 outside and surrounding the FSs 9 and BSs 10, such that each lead set reverses directions and runs back through the middle of the coil to its opposite ends to provide the cancellation effect discussed above. As shown in FIG. 10, from the standpoint of the RF impedances of the lines, the coils 10c may serve as series inductances, which, together with stray capacitance 7 with other sections 9 and/or surrounding environment, provide a current suppression affect.

Figure 11:
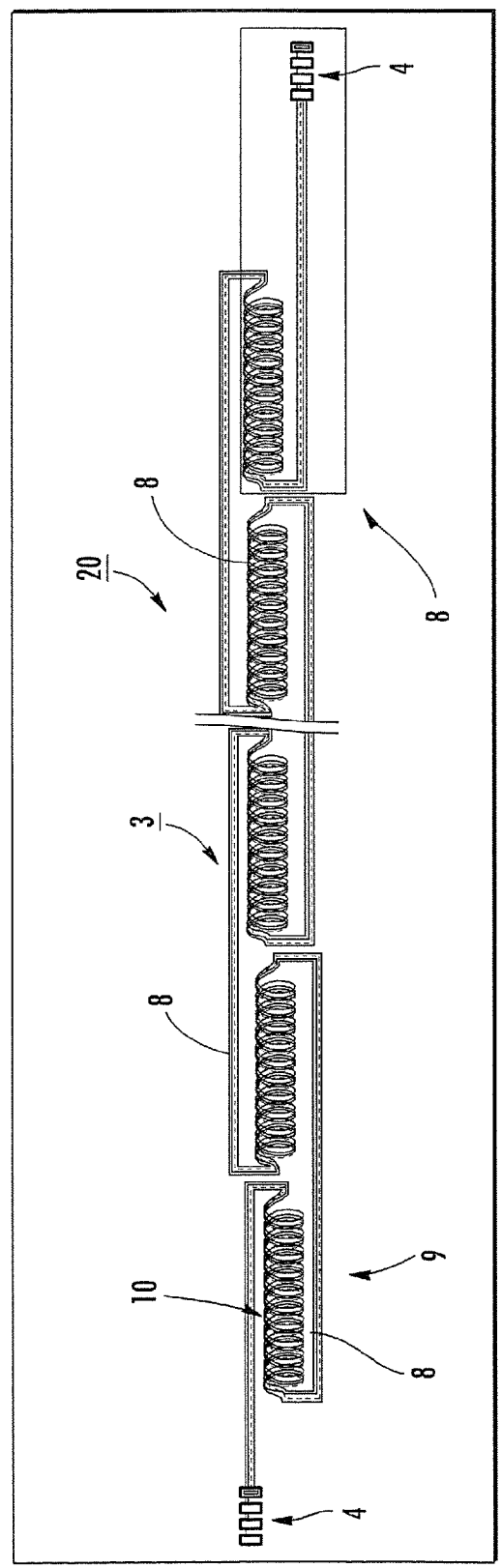
FIG. 11 is a schematic illustration of a lead with multiple conductors and multiple sensors and/or electrodes and multiple reverse and forward segments according to embodiments of the present invention.

A multi-electrode, multi-conductor lead system 20 is illustrated in FIG. 11 for a four electrode 4 and/or four conductor 3 lead system 20. FIG. 11 illustrates a subset of the modules 8, e.g., five CSMs 8 of an exemplary 11 CSM conductors of a 58 cm lead 20, and five CSMs 8 of 12 CSMs of conductors of a 64 cm lead system. For prototypes of the design shown in FIG. 11, each lead 20 was made with four conductors, namely 0.005" magnet wires (4 wires), each having a straight FS 9 about 9 cm long, and a coiled BS 10c (also interchangeably called a "CBS") about 4.3 cm long. The coils 10c had a 0.046" ID with respective coiled segments 10c of the different conductors being substantially co-wound. Multiple digital photographs of a prototype lead 20 for connecting between electrodes and an IPG or pacemaker are shown in FIGS. 12A-D: 12A the entire lead; 12B the distal end showing the electrodes; 12C and 12D, close-up photographs of the modules 8 and coils 10c. These leads 20 were tested for in vitro tissue heating performance in a gel phantom in a 1.5 T (64 MHz) MRI scanner system. The local temperature changes in the gel around different sections of the lead (distal end "DM1", proximal end "PM1", near electrode "electrode") were measured and are reported in FIGS. 13A and 13B. Less than a 1° C. temperature rise was recorded in the gel adjacent to the lead 20 at these three locations when using an MRI sequence having a peak SAR input of >4 W/kg.

While a four-electrode 4 containing four CSMs 8 is shown in FIG. 11, CSMs 8 for multi-conductor lead systems can typically comprise between about 2-100 conductors 3 and/or electrodes 4, but even greater numbers of conductors 3 and/or electrodes 4 can be formed according to the embodiments described herein are included within the scope of the present invention.

In embodiments of the present invention, one or more such CSMs 8 of the type illustrated in FIG. 11 for multiple conductors can be arranged so that a CSM 8 of a respective conductor is separated from a neighboring CSM 8 by an electrical length of $\lambda/4$ or less, analogous to the single line arrangement depicted in FIG. 7, where $\lambda$ is the EM wavelength of the straight (uncoiled) lead in the medium in which it is to be implanted. Although shown as having electrodes 4 on both ends, in other embodiments all electrodes may be at one end portion and connectors/interfaces to the power source or other device at the other end. Alternatively, multi-electrode and/or multi-conductor (>2 conductor) embodiments of the present invention can include conductors having separate suppression modules as shown in FIG. 7. The multiple conductors 3 can be grouped with the coil locations 10c displaced one from the other so that the coils 10e do not coincide in space, and the maximum lead diameter does not become excessive. Combinations of cowound and non-cowound coiled sections and grouped or ungrouped conductors may also be used. In some embodiments, each coiled segment of a respective conductor can be axially (displaced lengthwise) with respect to others, while in other embodiments some or all of the conductors can be stacked one over the other and/or cowound.

The configuration details of the conductors 3 and CSMs 8 are for illustration purposes only and not meant to limit the scope of the present invention. While not wishing to be bound to one theory of operation, it is contemplated that the primary purpose of one or more of the cooperating pairs of forward and reverse sections, the coil sections 9c and/or 10c, and/or the reactive elements depicted in FIG. 6A-E (coils and/or capacitors) is to alter the electrical length of the associated conductor lengths so that common mode currents induced on longer sections can be suppressed, offset or inhibited and an electrical connection can be provided between physically separated parts, such as electrodes and IPGs or pacemakers, or external EKG leads (or blood pressure transducer, or blood oxygen transducer, or sonography transducer) and a monitoring system, for example.

Figure 12A:
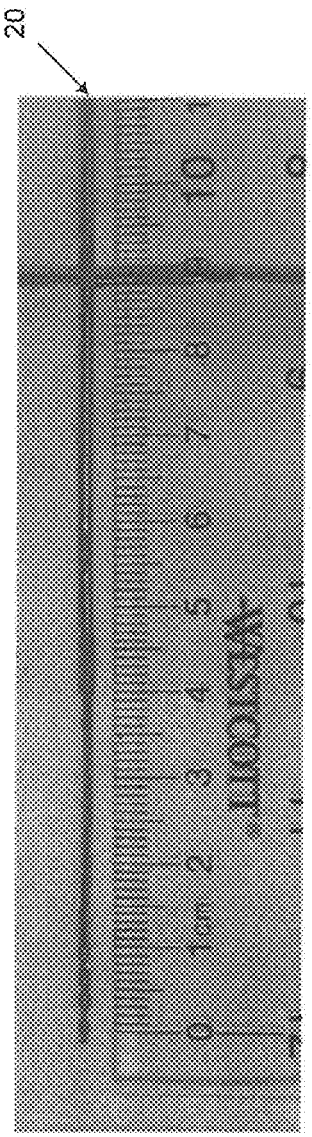
FIG. 12A is a digital photograph of a prototype flexible lead according to embodiments of the present invention.
Figure 12B:
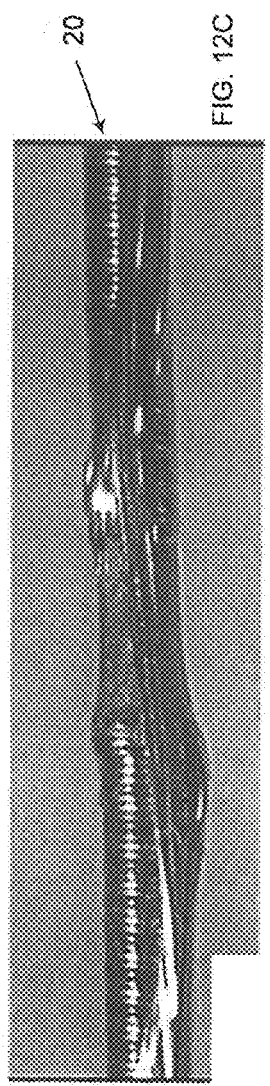
FIG. 12B is a partial view of the prototype shown in FIG. 12A with the end of the lead shown straight with respect to a ruler.
Figure 12C:
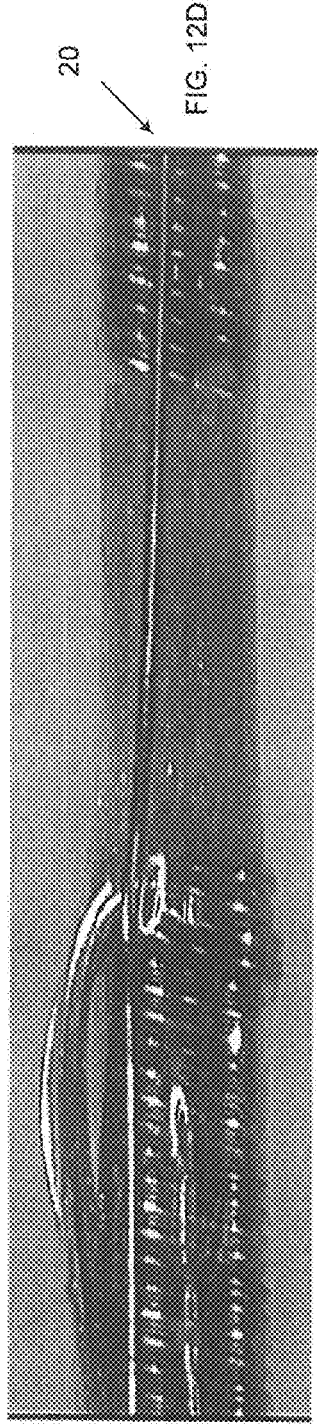
FIGS. 12C-12D are enlarged images of a portion of the lead shown in FIG. 12B.
Figure 12D:
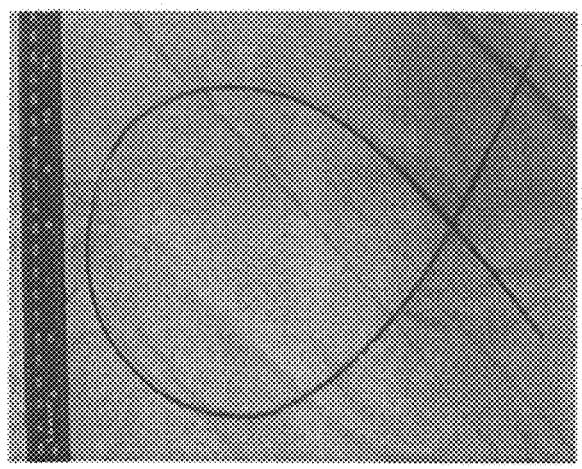

FIG. 12A is a digital photograph of a prototype flexible lead according to embodiments of the present invention. FIG. 12B is a partial view of the prototype shown in FIG. 12A with the end of the lead shown straight with respect to a ruler. FIGS. 12C-12D are enlarged images of a portion of the lead shown in FIG. 12B.

Figure 13A:
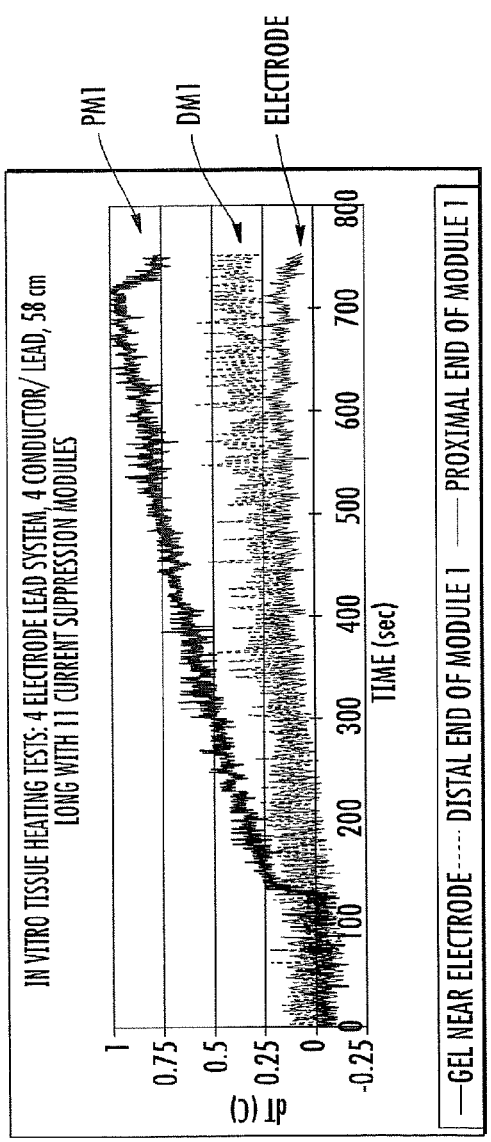
FIGS. 13A and 13B are graphs of temperature change (C) over time (seconds) for four electrode and four conductor lead systems according to embodiments of the present invention.
Figure 13B:
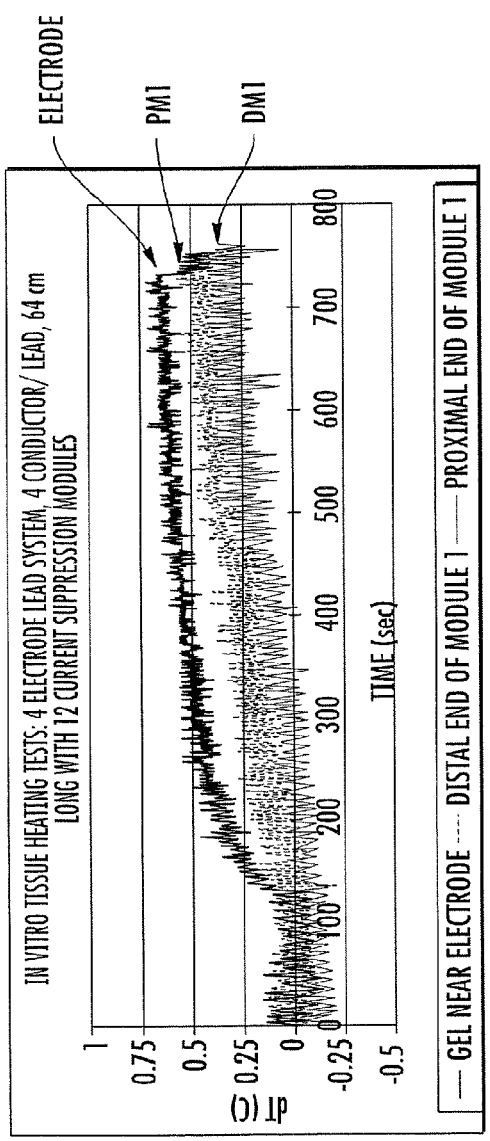

FIGS. 13A and 13B are graphs of temperature change (C) over time (seconds) for four electrode and four conductor prototype lead systems according to embodiments of the present invention. The graph in FIG. 13A illustrates temperature rise over time at a distal end of a CSM module 1 (DM1) and at a proximal end of CSM 1 (PM1) and in the gel near the electrode if a 4 electrode lead system with 4 conductors and 11 CSM modules having a length of about 58 cm. The graph in FIG. 13B illustrates the temperature rise of a 64 cm long prototype lead with 4 conductors and 4 electrodes and 12 CSMs.

Figure 14A:
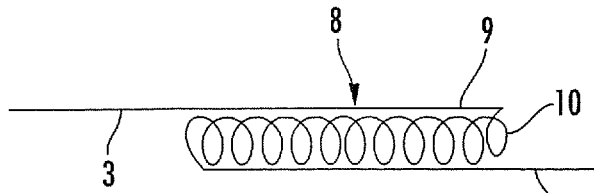
FIGS. 14A-14M are schematic illustrations of conductor configurations according to embodiments of the present invention.
Figure 14B:
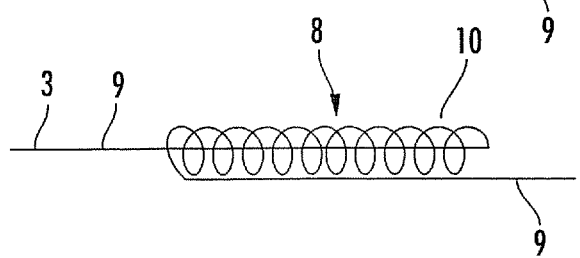
Figure 14C:
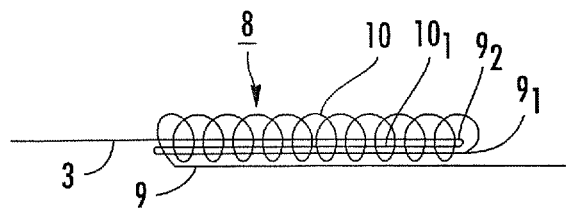
Figure 14D:
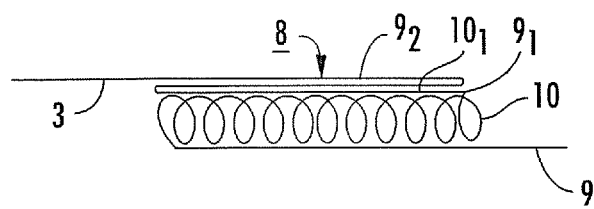
Figure 14E:
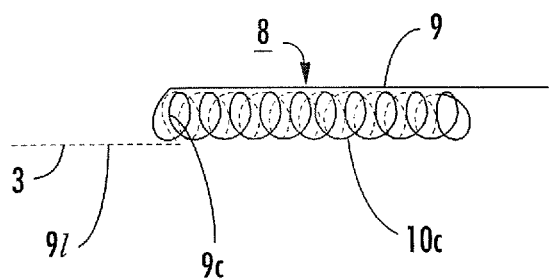

In particular, FIGS. 14A-14I illustrate exemplary CSM 8 configurations with alternative conductor 3 configurations and BS 10 and FS 9 according to some embodiments of the present invention as applied to a single conducting lead 3. In FIG. 14A, conductor 3 has BS 10 with a coiled segment 10c that runs substantially the entire length thereof analogous to the CSM shown in FIG. 9. FIG. 14B illustrates that one FS 9 may extend inside the coil of a BS 10 to provide the cancellation effect discussed above. The FS 9 passing through the coil may pass through any interior portion of the coil, thereby generally resulting in a reduction in the outer diameter of the lead as compared to FIG. 14A, but also affecting the RF impedance. This configuration is readily extended to multiple co-wound leads, for example with respect to FIG. 9, by running one bundle of leads FS 9 through the middle of co-wound coil 10c, to minimize lead diameter. FIGS. 14C and 14D illustrate that a FS 9 can axially loop or turn several times above, below and/or through a BS 10 (defining several "mini" or "sub" FS $9_1$, $9_2$ and an intermediate "mini" BS $10_1$) before extending axially downstream of the primary BS 10. The looping back and forth in this configuration provides an additional means of altering the electrical length of the section in accordance with the mechanisms of operation discussed above, thereby essentially creating a coil/inductance as in FIG. 14A, but with coil axis rotated about 90 degrees to augment coil 10. FIG. 14E illustrates that the FS 9 can include a coiled segment 9c and a linear segment 91, analogous to FIG. 6E. The coiled segment 9c can reside proximate the BS 10c. The BS coil 10c and the FS coil 9c can be substantially cowound but with each coil in opposing directions or coiled over or about one another or proximate each other to electrically couple, potentially produce current cancellation at the end of the BS and may generate increased impedance, such as, for example at least about 100 Ohms, and typically about 300 Ohms or more. The coil diameter, conductor size and/or type, and length of coil may be the same in the 9c and 10c sections, or one or more of these parameters may be different. The conductor 3 can be a single continuous conductor along substantially its entire length, and is typically the same conductor at least along a length of a respective CSM 8.

Figure 14F:
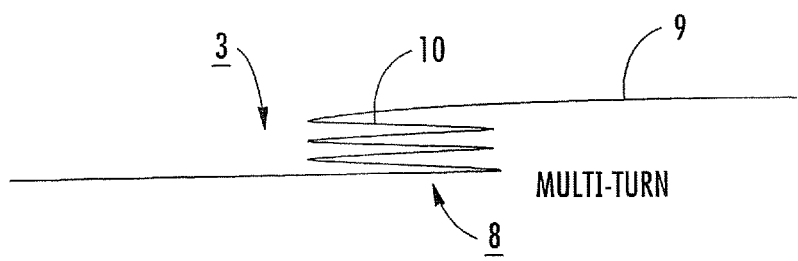
Figure 14G:
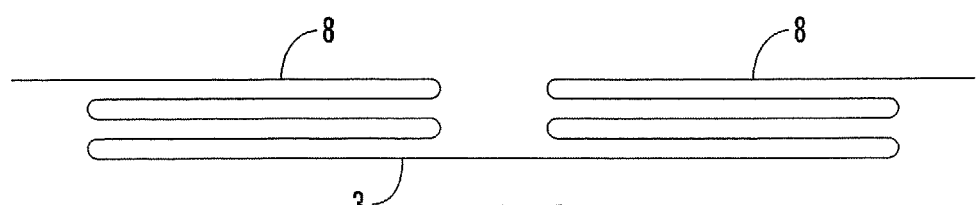
Figure 14H:
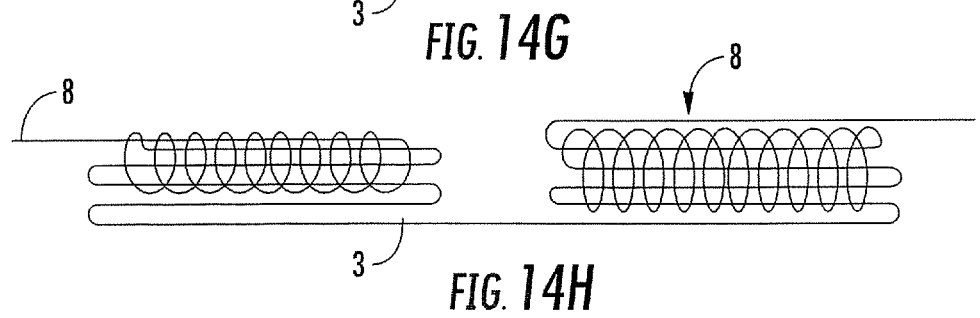
Figure 14I:
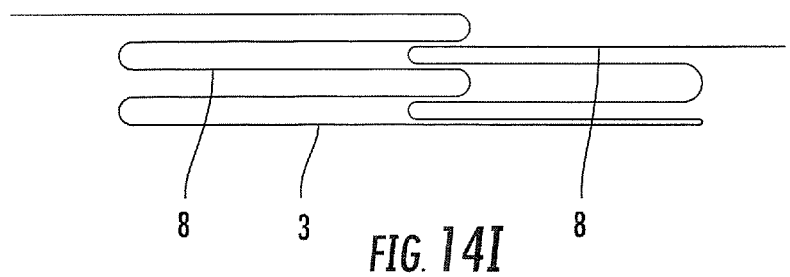
Figure 14J:
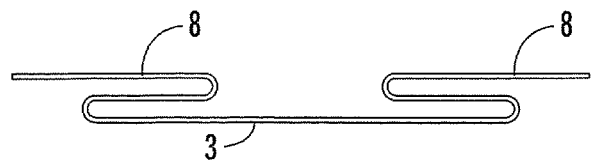
Figure 14K:
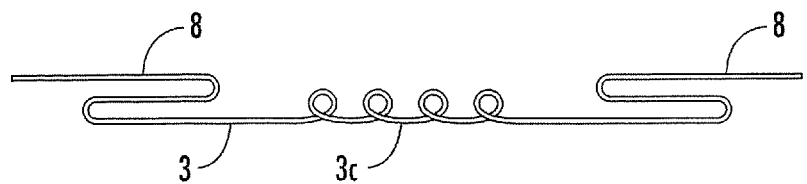

FIG. 14F illustrates that the conductor 3 can include a continuous closely spaced section of conductor that turns on itself several times in a lengthwise direction, analogous to the axial/lengthwise turns or loops introduced in embodiments FIGS. 14C and 14C. This configuration is similar to that in FIG. 14A, except that the coil axis is rotated 90 degrees, whereupon multiple BSs 10 are created by the coil windings. FIGS. 14G-14I illustrate yet other conductor CSM 8 configurations with a plurality of adjacent longitudinally extending back and forth lengths (which may be straight, taper or may be curvilinear) forming a series of stacked reverse and forward segments 10, 9, respectively. Although not shown, one or more coils 3c may extend between the adjacent CSMs 8, such as is shown in FIG. 14K (which also illustrates that the CSM 8 can include one double turn (one reverse segment) configuration. FIG. 14J illustrates a configuration similar to FIG. 14K but without the coiled intermediate segment 3c. Of course, the lead can include combinations of different types and configurations of CSMs 8.

FIG. 14H illustrates that the modules 8 can include both the side (lengthwise) extending segments and a coiled segment with the side extending segments being inside and/or outside the coiled segment and the coiled segment can be a forward or a reverse segment, analogous to FIG. 14C. FIG. 14I illustrates that the side segments of adjacent modules 8 in FIG. 14G, may be interleaved in part. In further embodiments, the interleaving of the conductor(s) is extended in whole, so that the axial and/or lengthwise loops are cowound and form a single module. This can be obtained, for example, by forming a flat loop of conductor at the center of module 8, then folding the loop several times and laying it against the two FSs 9. An alternative embodiment is to wrap the flat loop as a coil around a FS 9.

Figure 14L:
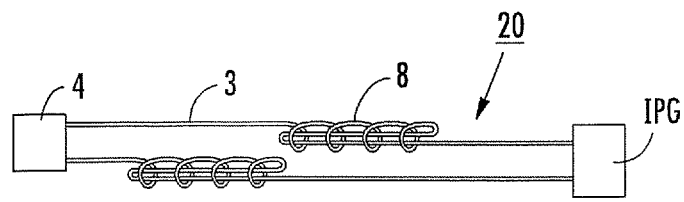
Figure 14M:
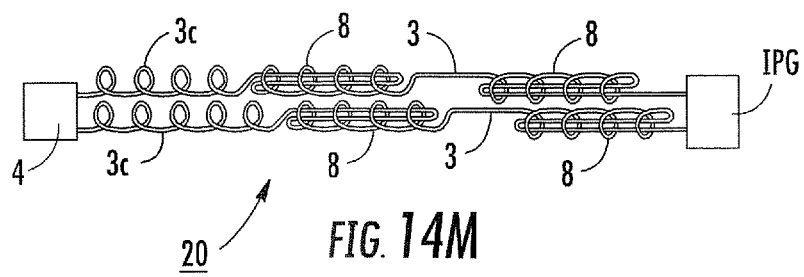

FIGS. 14L and 14M illustrate that the lead 20 can have at least one conductor 3 at least one CSM 8 that extends between an electrode 4 and a power source, such as an IPG. FIG. 14M illustrates that the distal end of the conductor 3 can be coiled as it connects to the electrode 4 to further reduce heating proximate the electrode. Also, FIG. 14L illustrates that more than one conductor 3 may be used to connect a single electrode 4 for redundancy and/or lower power or energy transmission or the like.

Figure 15A:
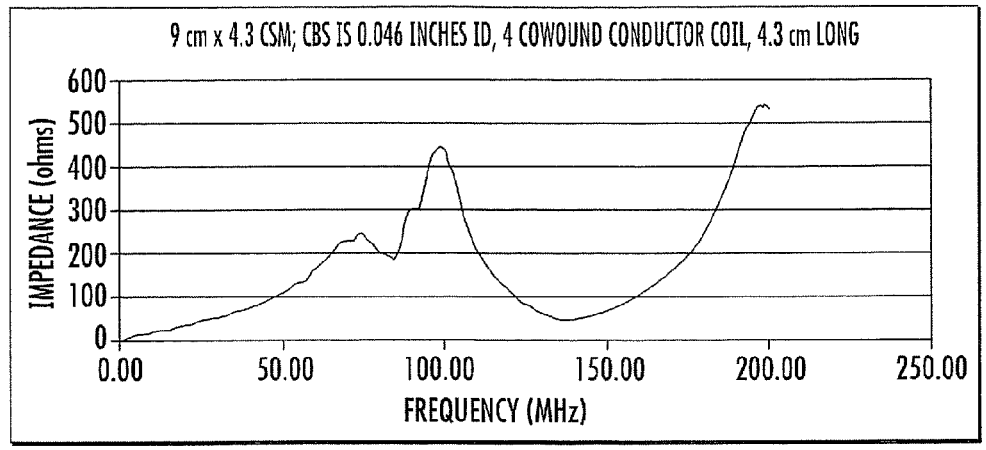
FIGS. 15A and 16 are graphs of impedance (Ohms) versus frequency (MHz) for some exemplary leads measured in saline according to some embodiments of the present invention ("CBS" in FIG. 16 means "coiled backward section" and "CSM" means current suppression module).
Figure 15B:
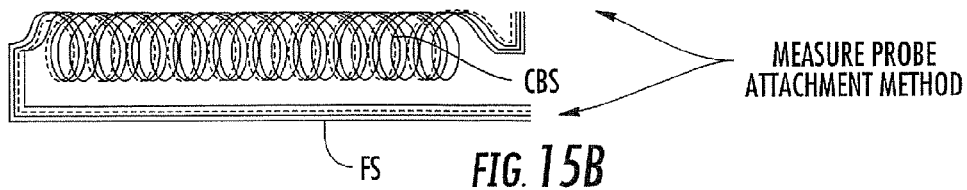
FIG. 15B is a schematic of a measurement probe attachment configuration that can be used to measure impedance such as the results shown in FIG. 15A according to some embodiments of the present invention.

FIG. 15A illustrates impedance versus frequency for a single CSM when immersed in a physiological saline solution. The CSM comprises 4.3 cm Coiled Back Sections (CBS) and 9 cm (straight) forward sections (FS). The CSM has 4 cowound conductors (for prototype proposes, magnet wires, 0.005" diameter) with the CBS having about a 0.046 inch inner diameter. FIG. 15B illustrates that the impedance can be measured by connecting the impedance measurement probe to the CSM at the two points shown by the arrows.

Figure 16:
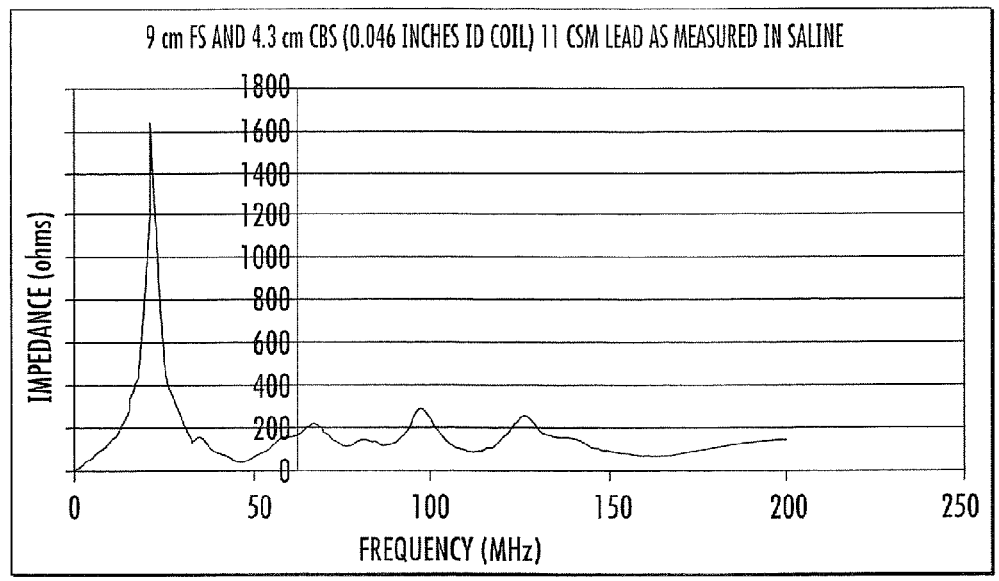

FIG. 16 illustrates impedance versus frequency for an entire lead with eleven axially spaced consecutive CSMs, when immersed in a physiological saline solution. The lead is a 4 electrode system with FS having a length of about 9 cm and the CBS having a length of about 4.3 cm and an inner diameter of about 0.046 inches. The use of multiple CSMs may alter the impedance dispersion in accordance with the cumulative impedance and wavelength effects associated with the longer lead length. The impedance data shows very low resistance (~1 ohm) at DC frequencies and around 60-300 Ohm impedance at RF frequencies, although a peak of around 1600 Ohm is evident at ~20 MHz. Thus, the conductors 3 can have broadband low pass filtering, while affording a higher impedance narrowband filtering effect at specific frequencies.

Although the local maxima of the exemplary impedance is shown at between about 20-25 MHz, the location and/or maxima impedance characteristics can be adjusted to other desired RF frequencies by re-configuring the CSM, e.g., changing one or more of the length of the BS 10, the diameter of conductors defining the coil 10*c* (e.g., inductors) and/or or part of the FS 9*c*, and/or the number of revolutions on the conductors in the coiled BS 10*c*. Also, the leads 20 can be configured with multiple FSs 9 and BSs 10, to generate maxima at multiple frequencies (or frequency bands) by adjusting the configuration, e.g., length/diameter/number of revolutions of different ones of the FSs 9 and/or BSs 10.

Thus, according to some embodiments, the conductors 3 with CSMs 8 can have an impedance that varies and exhibits local maxima at a frequency band and/or over a target frequency range. In some particular embodiments, the CSMs 8 can exhibit an impedance of at least about 100 Ohms over its respective length at a target radio frequency of interest. The FS and BS sections 9, 10, respectively, can be configured such that at least one local impedance maxima substantially coincides with at least one frequency (or frequency band) of interest (e.g., 64 MHz for 1.5 T, 128 MHz for 3 T, etc.) within that range. Because the local maxima are relatively broad, the target frequency band can be within +/−about 5 MHz of the typical RF frequency of an MRI scanner. In some particular embodiments, the target impedance local maxima can also be the global maximum.

FIG. 17 shows heat-test data from the eleven-CSM lead whose geometry and impedance properties are shown in FIG. 16 obtained using the MRI parameters: FSPGR sequence, TE=4.2, TR=17.3, BW=125, FA=170, 256=128 image matrix; TG=155—peak input SAR~4.2 W/Kg. FIG. 17 is a graph of local temperature change measured at different locations along the length of the lead with eleven CSMs (corresponding FS and CBS) in a 1.5 T MRI scanner operating at 64 MHz. The test method is as described with respect to FIGS. 8A-8C.

FIG. 18 illustrates local temperature change measured at different locations along the length of a lead with eleven CSMs in a 3 T MRI scanner with measured peak input SAR=4.2 W/Kg. The MRI RF frequency in this case is 128 MHz. The lead corresponds to that analyzed with respect to FIGS. 16 and 17, and the same test method as described for FIGS. 8A-8C was used.

It is noted with reference to the eleven CSM lead depicted in FIGS. 16-18, that impedance maxima in FIG. 16 do not exactly coincide with the two MRI frequencies of 64 and 128 MHz. Nevertheless FIGS. 17 and 18 show that the leads are still highly effective at limiting heating at the higher frequencies. This is consistent with the common mode mechanism playing a significant role at the frequencies of interest. Also, the same lead can be effective at limiting heating at two MRI scanner frequencies, e.g., both at the 1.5 T frequency and at the 3 T frequency, and thereby potentially provide suppression of potentially injurious lead heating and/or device damage in multiple MRI scanner and/or RF environments. In particular, the conductors 3 may provide for rejection of induced voltages and currents over a broad band of RF in the range between about 10 MHz to about 200 MHz. In some embodiments, the local maximas can correspond to two or more RF frequencies of interest, where one or more is an RF MRI frequency corresponding to 0.1, 0.3, 0.7, 1.0, 1.5, 2.5, 3, 4, 4.7, 7, and 9.4 Tesla.

Figure 19:
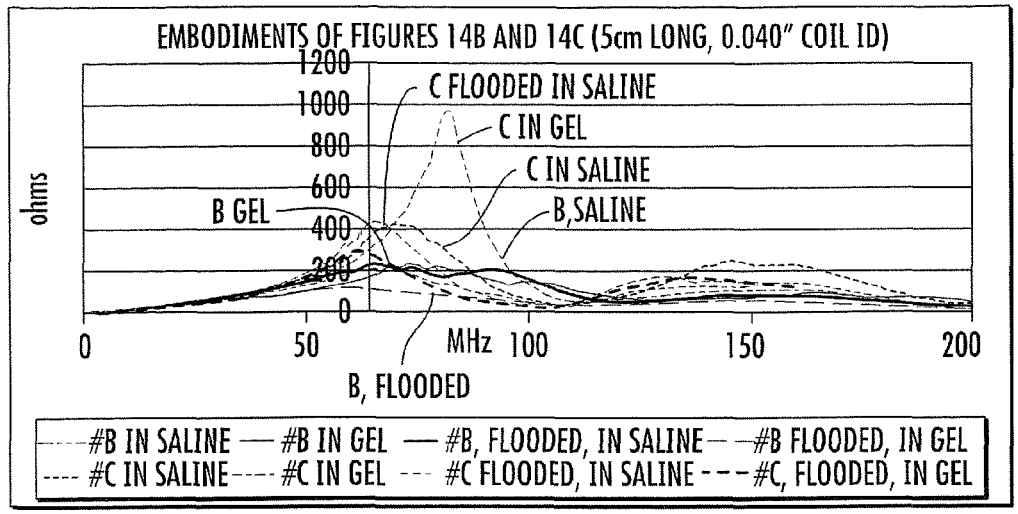
FIGS. 19 and 20 are graphs of impedance (Ohms) versus frequency (MHz) of leads measured in various materials (saline, gel).
Figure 20:
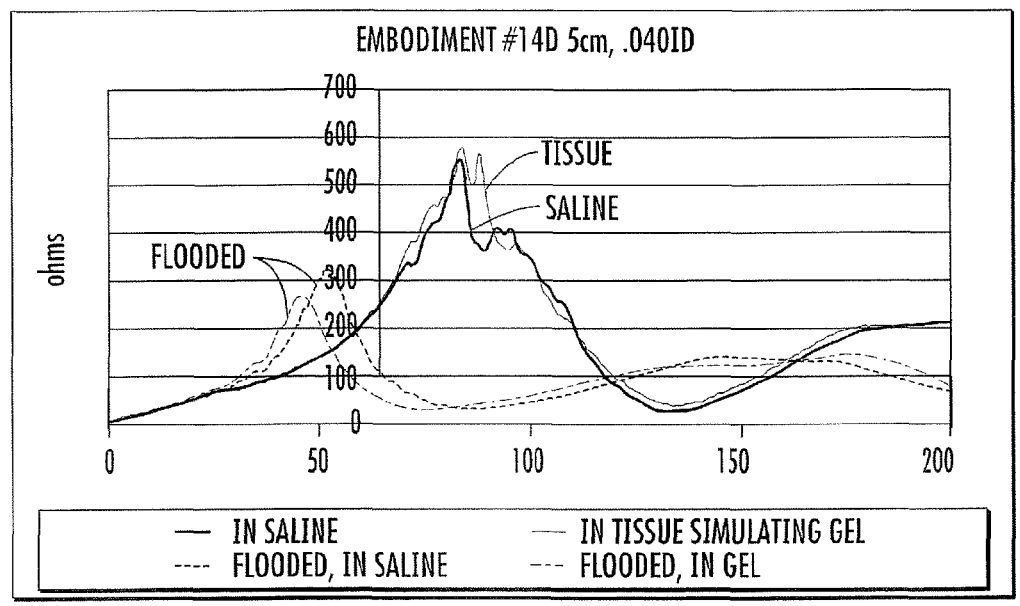

FIGS. 19 and 20 are graphs of impedance versus frequency (MHz). In these graphs, embodiment "B" refers to the embodiment shown in FIG. 14B, embodiment "C" refers to the embodiment shown in FIG. 14C and embodiment "D" refers to the embodiment shown in FIG. 14D. Each embodiment is able to generate multiple local maximas over an RF frequency range (MHz) with Embodiment C generating about 1000 Ohms at between about 70-80 MHz and generating over 200 Ohms between about 50-100 MHz. The word "flooded" means that there was no polymer layer on the conductor (magnet wire) CSMs so that the conductors are in complete contact with the surrounding medium (saline or gel).

As shown, the conductors 3 can be configured to increase the impedance and/or shift the frequency of local maxima of the impedance depending on the length of the CSM (FS 9, BS 10, FS 9) and the orientation of the FS 9 with respect to the coiled BS 10*c*. In general, discrete or distributed impedance elements such as inductors and/or capacitances, may be included in the leads for increasing impedance or tuning the local impedance maxima and providing desirable current suppression capabilities.

It is further noted that the conductors 3 and/or current suppression modules 8 may incorporate one or more of the above configurations described above and/or other features, such as, for example, but not limited to, one or more of the following:

1) Thicker insulation on the FSs 9 as compared to the BSs 10. Thicker insulation on the FSs 9 of the current suppression module 8 may reduce the current deposited on FSs 9 and thereby allow the length of the forward section to be increased.
2) In other embodiments, shielding of the conductor(s) 3 and/or the lead FSs 9 can inhibit RF deposition and thus reduce the current deposited on the FSs 9 as compared to no shielding. Discrete or wound RF chokes as inductive elements, and/or capacitive elements may be arranged between the shielding to provide improved suppression capabilities. The shielding can be continuous, discontinuous, or may be achieved by multiple methods, to list a few, e.g., insulating conductors with polymers filled with conducting metals doped for conductivity, a braided covering and the like.
3) Making the FSs 9 physically longer than the BS 10, but forming the FSs 9 to be electrically substantially equivalent or of shorter length.
4) Different ones of the RF-current induced suppression modules 8 for a respective lead or a respective conductor can be configured to have a different physical length and/or configuration to provide a desired electrical length and RF current suppression at a different operational frequency. For example, for a multi-electrode system, some of the RF-current induced suppression modules 8 thereof can be configured to provide the λ/4 wavelength or less at a different MRI scanner frequency than others, allowing for compatibility with different high-fields, for future compatibility or backward compatibility.

5) The lead can be between 1 French to about 40 French. For cardiac leads, the size can be between about 1 French to about 10 French. The lead and conductors may be flat or have a geometric shape, tubular or otherwise. The lead is typically flexible but can be configured to be substantially rigid.

In some embodiments, standing wave formation on long (coaxial) conductors may be attenuated by incorporating balun circuits or RF chokes at various locations on the longer FSs 9 or sections of the lead 3 that extend between CSMs 8, or between electrodes or an electronic device and a CSM, or on a shield where this is included in embodiments noted above. See, Atalar et al., U.S. Pat. No. 6,284,971, entitled, Enhanced Safety Coaxial Cables, the contents of which is hereby incorporated by reference as if recited in full herein. See also, Ladd et al., *Redaction of resonant RF heating in intravascular catheters using coaxial chokes*, Magn Reson Med 2000; 43 (4): 615-619. See also, PCT Application Serial No. PCT/US2005/028116, filed Aug. 9, 2005, entitled, Implantable MRI Compatible Stimulation Leads and Antennas and Related Systems and Methods, the contents of which are hereby incorporated by reference as if recited in full herein. Generally stated, this co-pending application describes incorporating RF chokes on (DBS and CP) lead systems, and again would be applied in embodiments herein to the longer FSs or portions of lead 3 that extend between CSMS, or between electrodes or an electronic device and a CSM, or on a shield where this is included as above.

Some physical and electrical parameters or characteristics of the conductor 3 and/or FS 9 and BS 10 with modules 8 incorporated in the leads 20 include:

1) Physical lengths of each current suppression module 8 of a conductor between about 1 cm to 3 m long, but typically about 4 cm to about 10 cm.
2) Numbers of CSMs per conductor: typically between about 1-100, and more typically between about 1-25.
3) Transverse spacing of each or some CSMs of a respective conductor can be between about 0.1 mm to about 20 cm, and typically between about 1 cm to about 9 cm.
4) RF impedance of a CSM can be any suitable value, from low impedance to high impedance, such as above about 5 ohms, typically >20 ohms, and in some embodiments about 100 Ohms or greater along the length of a respective CSM at RF frequencies of interest.
5) Overall RF impedance of the conductor and/or lead can be any suitable value, but, in some embodiments, can be about ≥100 ohms.
6) Low DC resistance (allowing for lower power requirements and/or longer battery life in some embodiments).
7) Cross-sectional width, typically diameter, of the conductor(s): 0.0001 inches to about 0.5 inches, and typically between about 0.001 inches to about 0.2 inches, and more typically between about 0.002 inches to about 0.1 inches. One or more of the conductor(s) can be insulated and/or insulated and shielded.
8) The conductors may be circular, flat, rectangular, square or elliptical or other shape in cross-section. The insulator, where used, can be conformal so that when they are applied to the conductor, does not change the shape.
9) The conductors can comprise any MR and biocompatible material, including, for example, Au, Ag, Nitinol, Ti, Pt, Ir or alloys thereof, MP35N, SST, DFT (drawn filled tube, typically with a MP35N outer layer and a conductive (metallic) core such as a silver core).
10) The conductors can be insulated by biocompatible materials such as, for example, Teflon, Nylon, polymers, PTFE, ETFE, silicone, polyurethane, PEEK (poly ether ethyl ketone), and/or epoxy, which also act as dielectric material distributed between the various conducting section in the leads.

FIGS. 21A, 21B, 21C and 22A, 22B, 22C are examples of leads 20 comprised of stacked multi-layers 8m forming the CSMs 8 of conductor 3. FIG. 23 shows a lead 20 with at least one conductor 3 formed with a plurality of CSMs 8 spaced apart in a lengthwise or longitudinal direction.

Figure 21A:
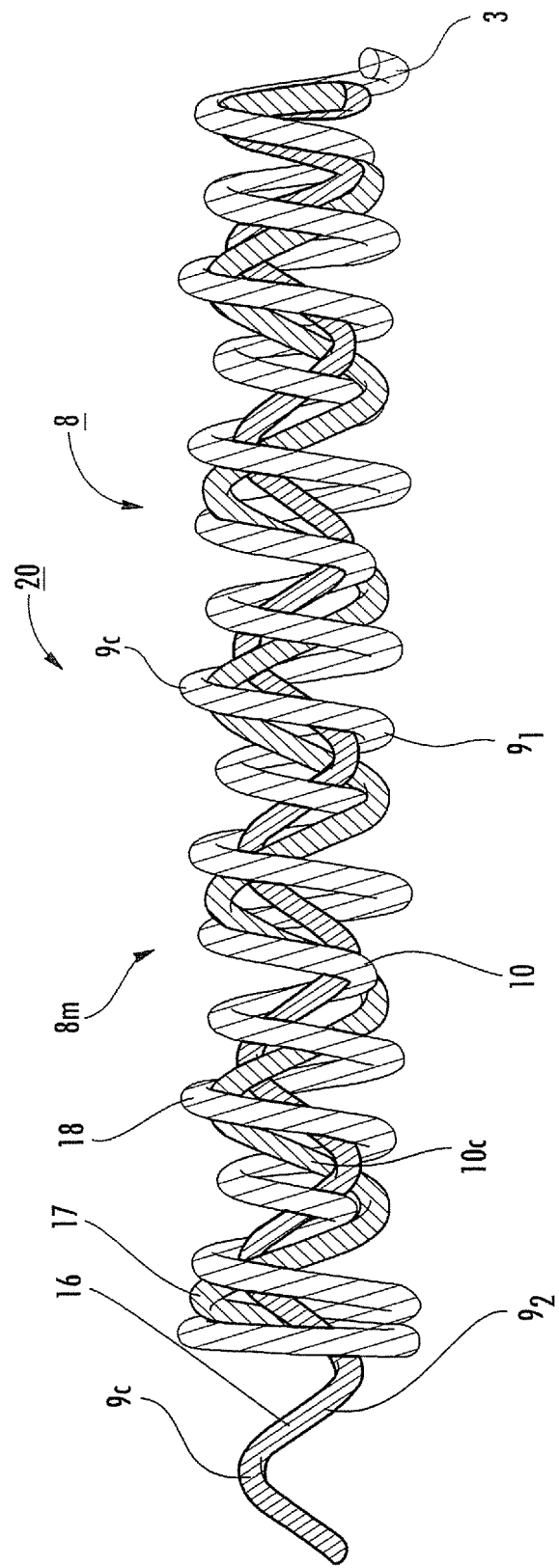
FIG. 21A is a schematic illustration of a single conductor with a multi-layer stacked coil configuration (tri-layer) of two forward segments connected by one reverse segment according to embodiments of the present invention.

In particular, FIG. 21A illustrates a tri-layer configuration with three coiled segments closely stacked over each other, with a first inner layer coil 16 as a FS 9c, an intermediate second layer coiled back section 17 (10c) and a third outer layer coiled forward section 18 (9c). FIG. 21B illustrates a single conductor triple stacked or tri-layer configuration 8m while FIG. 21C illustrates a two conductor $3_1$, $3_2$, triple stacked configuration 8m. As shown in FIGS. 21A-21C, the outer coil 18 and inner coil 16 can form two FS 9 ($9_1$, $9_2$) and the intermediate coil 17 can be a BS 10. For leads with more than one conductor 3n (where n>1), two or more of the conductors 3n can be cowound to form the three layers, analogous to FIG. 9, as shown, for example, in FIG. 21C which illustrates a two conductor $3_1$, $3_2$ stacked CSM configuration 8-2. For a three (or more layer configuration), the first layer 16 (8i) can be wound from left to right (distal to proximal end of the lead), the second layer 17 (8k) can be wound over the first layer and is wound right to left (from proximal to distal end of the lead), the final layer 18 (8o) on the top of the two can be wound left to right (distal to proximal end of the lead) and may have the same or smaller (e.g., closer) pitch than the first two layers. In this embodiment (stacked three-layer), all the layers 16, 17, 18 can be coiled maintaining the same rotation direction (CW or CCW) for the coil winding equipment. A fourth or additional layers can be stacked on the third layer 18 (not shown).

FIG. 21D illustrates a single conductor 3 in a tri-layer stacked configuration 16, 17, 18 (with each successive coil on a different but closely abutting over layer) held about an integral flexible inner sleeve 190, which may define an open lumen (not shown). As shown, at least one end portion of the conductor 3p (e.g., the proximal end) can be configured so that the last or first CSM 8 merges into a wider pitch coil 3w for a number of revolutions, such as, for example, 3-10 revolutions. As also shown, a relatively short outer sleeve 199 can be placed over a portion of the CSM 8 as well as the coils 3w to help hold the conductor 3 in position/shape before the outer layer is placed thereon (e.g., by molding or other suitable method). The short outer sleeve 199 length can vary, but in some embodiments can be between about 0.5 cm to about 2 cm long.

FIGS. 22B and 22C also illustrate a two-layer multi-stacked CSM 8m, with FIG. 22B illustrating a single conductor CSM 8 and FIG. 22C illustrating a two conductor $3_1$, $3_2$ CSM 8-2. As shown, the inner layer 8i includes one FS 9c and one BS 10c, which reside under the other FS 9c formed as the outer CSM layer 8o.

FIGS. 22D-22F illustrate a portion of a lead 20 with a two-conductor 8-2, double stacked CSM 8. FIGS. 22D and 22F show the top layer 8o in section view to illustrate the underlying layer 8i of the pattern of the two conductors $3_1$, $3_2$. As shown in FIG. 22F, the conductors $3_1$, $3_2$ change rotational direction once at an end portion 33 of a respective CSM 8. FIG. 22E illustrates that a short length of a sleeve (such as a PET heat shrink tube) 199 can be placed over the end portion of the CSM 33 at least one end of the lead and a few revolutions of the conductors $3_1$, $3_2$ proximate thereto to hold the conductors in position against the sleeve 190 and/or mandrel 190m. In addition, a small amount of UV adhesive or other suitable adhesive (or other temporary or permanent attachment means) can be placed on the conductors $3_1$, $3_2$ and/or sleeve 190 at position 33 to help hold the conductors in position prior to winding the next CSM 8. Other inner diameter sleeves/tubes can be positioned at different locations to help hold the conductor(s) in position, such as for attaching one or more electrodes/sensors or transducers to the lead body (not shown).

In some embodiments, the leads are multi-conductor leads 20, such as, for example, but not limited to, leads having between about 2-100 conductors 3, typically between about 2-50 conductors 3, and more typically between about 3-16 conductors and some or all of the conductors 3 can be wound side-by-side in a substantially flat or level first layer in a first direction (e.g., front to back or right to left direction).

In some embodiments, the co-wound conductors can then be wound to form a second layer interleaved with and/or over the first layer, then wound to form at least a third layer (or even more layers), again with the third layer interleaved with and/or above the first and/or second layer. Depending on the crossover of the conductors as the conductors 3 transition to the different lengthwise directions, the second and third layers (or additional layers where used) may have a varying diameter, but the layers may be substantially concentric with each other.

Each coil within a CSM 8 can have a different pitch or some or even all of the coils in a single CSM 8 can have substantially the same pitch. In some embodiments, the first layer coil(s) can have a wider (lower) pitch and one or more of the overlying coil(s) can have a closer/more narrow (greater) pitch. Each layer of one or more coils of a respective conductor(s) can have a relatively thin thickness corresponding to the size of the conductor (with insulation), such as between about 0.0001 inches to about 0.2 inches. In some embodiments, each layer has a thickness of about 0.001 inches to about 0.006, such as, for example about 0.0026 inches, for a total thickness of the lead being less than about 0.20 inches (depending on the thickness of the outer encasement layer), such as, for example, between about 0.015 to 0.020 inches.

The different closely spaced and/or stacked coiled subportions of a single conductor 3 can be wound with the same or different pitches to form a CSM 8 and/or a CSM as well as the leading portion of the next, neighboring CSM 8 and/or a bridge to the next neighboring CSM 8.

In some particular embodiments, the different CSMs 8 of a respective conductor 3 can optionally be formed using multiple lengths of discrete conductors attached together, rather than a single continuous length of conductor. For a continuous length conductor, the windings can be substantially continuous along a length of a respective conductor (or, where used, multiple conductors co-wound during the same winding set-up) and can be formed by substantially continuously or intermittently winding a respective conductor using an automated coil winder, such as, for example, an Accuwinder Model 16B, available from Accuwinder Engineering Co. having a place of business at San Dimas, Calif.

A lead incorporating multiple CSMs 8 (as illustrated in FIG. 23) was prototyped and tested with two 0.007" diameter 35N LT-DFT conductors (e.g., wires/filars) with silver core (19 filar cable, 0.005" conductor OD and 0.001" wall ETFE insulation), with the conductors (e.g., wires/filars) cowound parallel to each other and coiled in three layers. The first layer (coiled forward section) has an inner diameter of 0.023", the second layer (coiled back section) is coiled over the first and the third final layer (coiled forward section) is over the first and the second layers. This CSM had an impedance of over 200 ohms at 64 MHz and length of 4.7 cm. The winding details are listed in Table 1 below.

TABLE 1

EXEMPLARY TRI-LAYER CSM

| Layer # | Winding Direction | Direction of rotation | Pitch | Length |
|---|---|---|---|---|
| Layer #1 | Left to Right | Clockwise | 0.050" | 4.7 cm |
| Layer #2 | Right to left | Clockwise | 0.050" | 4.7 cm |
| Layer #3 | Left to Right | Clockwise | 0.020" | 4.7 cm |

Figure 24A:
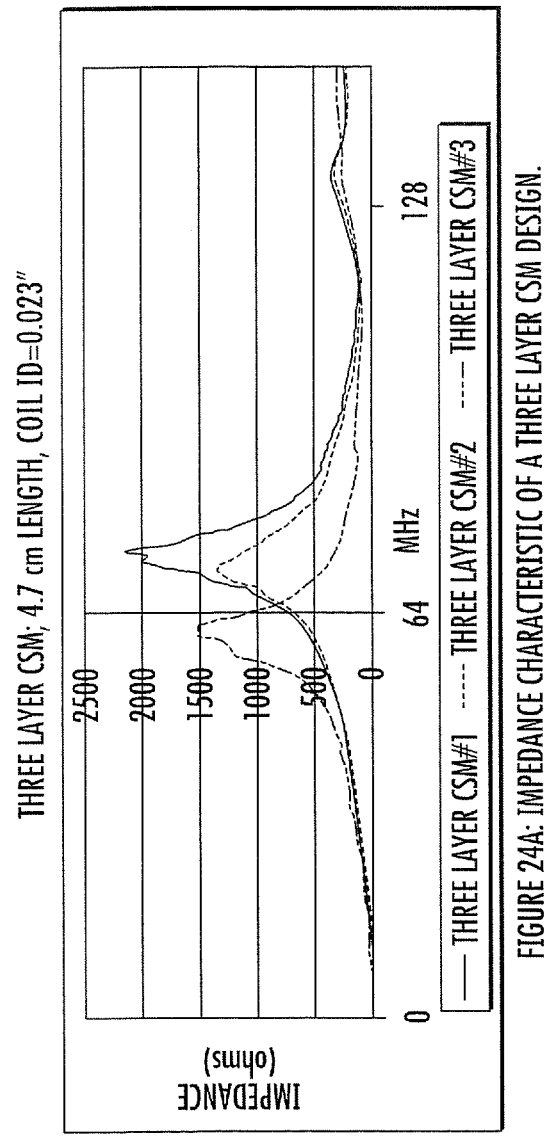
FIG. 24A is a graph of impedance (Ohms) versus frequency (MHz) of a lead having a plurality of spaced apart (in the lengthwise direction) three layer current suppression modules (CSM) described in FIG. 21A.
Figure 24B:
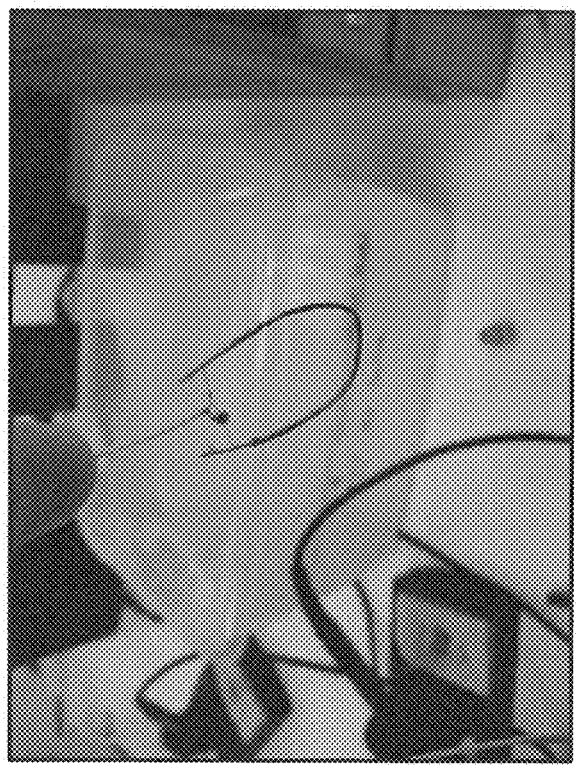
FIG. 24B is a digital photograph of an exemplary method to measure impedance of a current suppression module of a multi-conductor configuration according to some embodiments of the present invention.
Figure 25A:
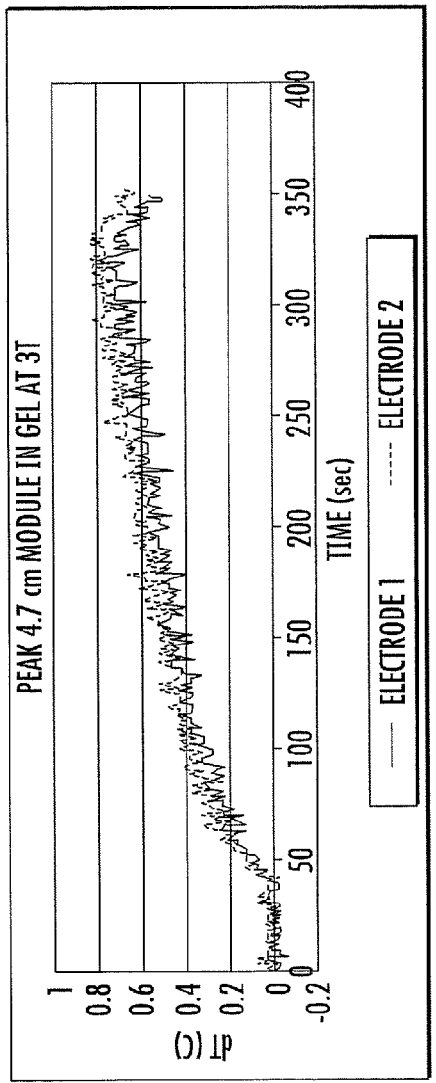
FIGS. 25A and 25B are graphs of temperature change (C) versus time (seconds) of a 61 cm lead with two conductors and with two electrodes, each conductor having three-layer current suppression modules (about 12 current suppression modules along its length) configured as described in FIG. 21A.
Figure 25B:
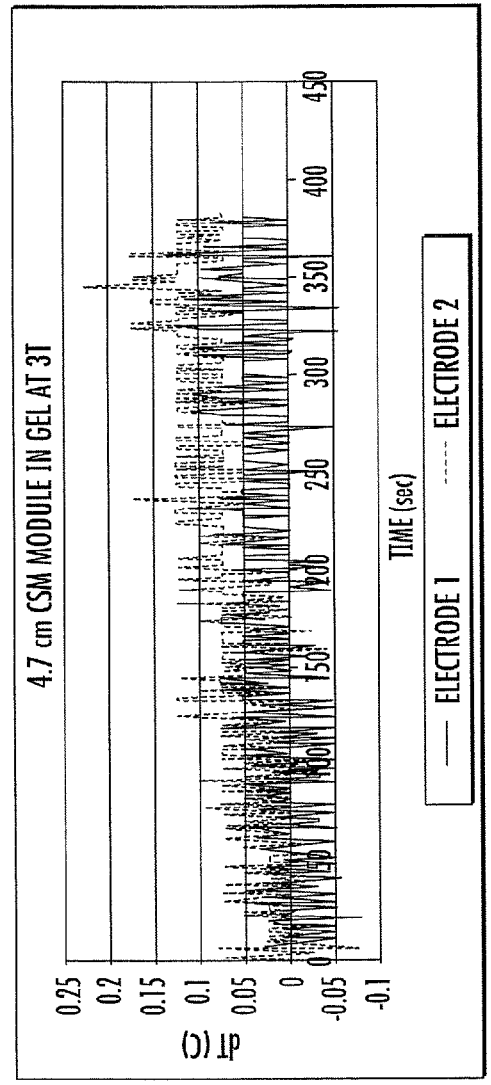

The impedance of the 4.7 cm CSM section is shown in FIG. 24A. FIG. 24B shows one example of a technique that can be used to measure impedance of a multi-conductor configuration (the measurement may be different for different CSM configurations). As shown, the measurement probe can be connected to different conductors of the device, taking care to connect the same conductor on each end of the device to be measured (e.g., conductor 2 of 4) and connect this conductor to the measurement probe shield and core. The network analyzer can be calibrated to the end of the measurement probe and the impedance can be measured when loaded in a saline solution. A two conductor, 62 cm long lead, incorporating 12 cowound trilayer CSMs 8m along the length of the lead, was heat tested in 1.5 T (64 MHz) and 3 T (128 MHz) MRI scanners in an acrylamide gel phantom. The change in temperature ($\Delta T$) in the gel (simulating tissue) adjacent to the electrodes as measured to be less than 2° C. with a 4.3 W/kg peak input SAR, as shown in FIGS. 25A and 25B.

Figure 22A:
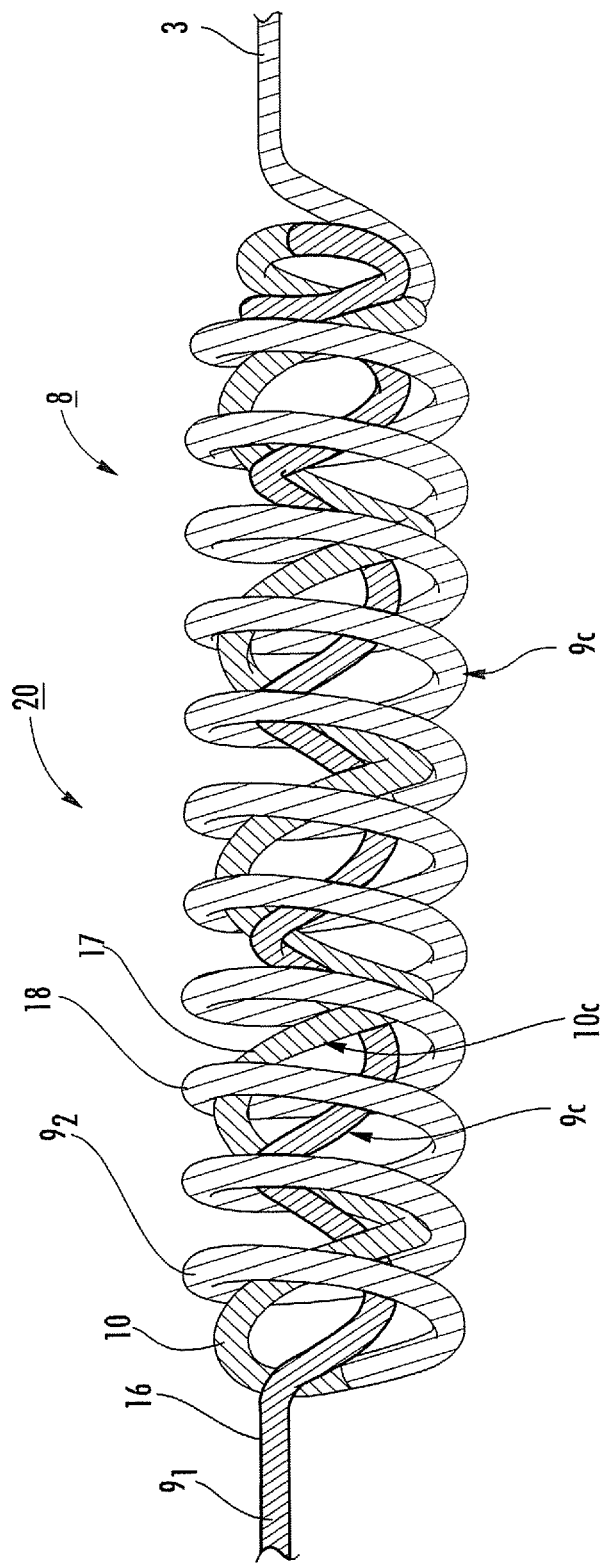
FIG. 22A is a schematic illustration of a single conductor with a multi-layer stacked coil configuration (two-layer) of two forward segments connected by one reverse segment according to embodiments of the present invention.
Figure 23:
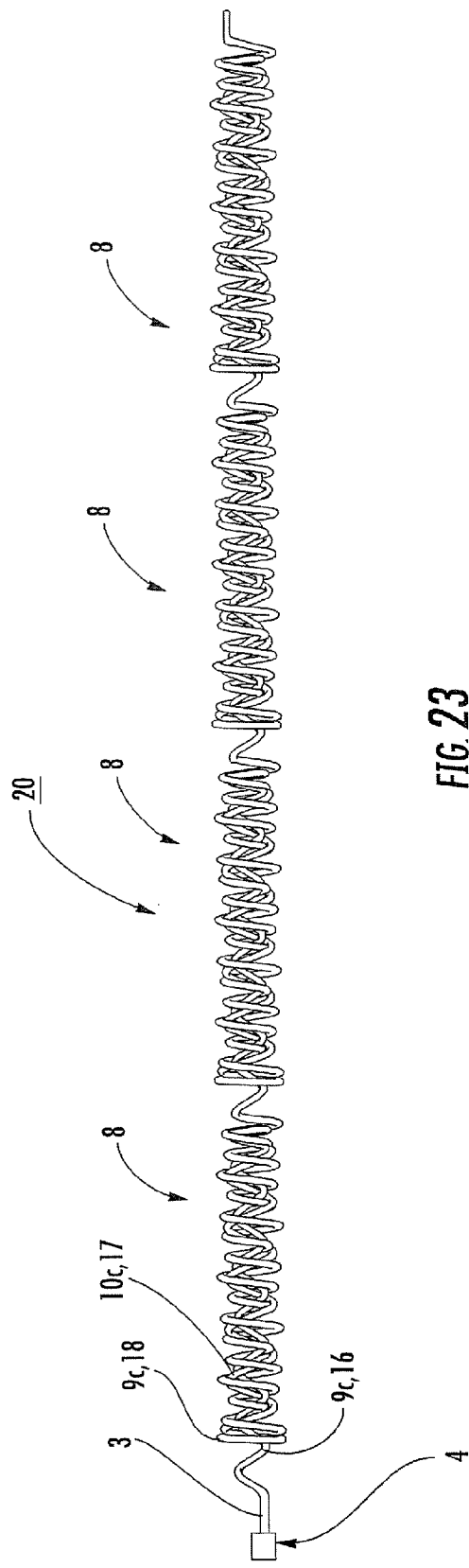
FIG. 23 is a schematic illustration of a lead with a conductor having multiple spaced apart segments of the multi-layered coils connected to an electrode according to embodiments of the present invention.

FIG. 22A is a two-layer coil stack configuration of a conductor 3 where one or more conductors are wound/cowound in forward-back-forward sections. As shown, two coils 16, 17 are on the same layer adjacent and interleaved with each other and the other coil 18 resides over the inner layer. Typically the BS 10 is coiled in the pitch of the first FS $9_1$ on the first layer and the second FS $9_2$ is longer and extends over the BS 10 and FS $9_1$. The first forward and back sections 16 (9c) and 17 (10c) are wound such that these do not overlap, and the back section 17 (10c) fits in the pitch (gap) of the forward section 16. This can be formed by attaching the proximal end of the conductors to a coiling mandrel or sleeve thereon and switching the rotational direction of the winding (left to right CW, right to left CCW, then left to right CCW or vice versa). The final forward section 18 (9c) is coiled in the same direction of the back section and over the first forward and back section. The attaching can be adhesively and/or mechanically carried out.

FIG. 22B illustrates a single conductor 3 configuration of a double stack 8m with both the inner coil FS 9c and the BS coil 10c being inside the second layer 8o with coil FS 9c. FIG. 22C illustrates two conductors $3_1$, $3_2$ coiled to form a two-conductor 8-2 double stack CSM 8m with the inner layer 8i having both a FS and BS 9e, 10c, respectively, and the outer layer 8o having a FS 9c.

As discussed above with respect to FIG. 21D, FIGS. 22D-F also illustrates the optional flexible sleeve 190 (e.g., a biocompatible flexible sleeve). The sleeve 190 is typically placed over the coiling mandrel during fabrication and can remain as an integral part of the lead 20 while the mandrel is typically removed. Other sized sleeves can be used. The sleeve 190 outer diameter is typically sized to provide the desired diameter of the lead (taking into account the outer diameter of the lead will also correspond to the number of stacked layers as well as the outer over encasement or overlayer that defines a substantially constant outer diameter). The sleeve 190 typically has a continuous closed outer wall, but may be discontinuous and/or have open pores or apertures. In some embodiments, the sleeve 190 is biocompatible can comprise any suitable material, typically a polymer such as PTFE or Nylon (such as Vestamid® L2140), and can have any suitable size, such as, but not limited to, an outer diameter of between about 0.01 inches to about 0.1 inches, typically between about 0.01 to about 0.05 inches, more typically about 0.024 inches, a wall thickness of between about 0.001 inches to about 0.02 inches, and can include a through lumen inner diameter of between about 0.001 inches to about 0.025 inches, typically between about 0.010 to about 0.02 inches, such as about 0.014 inches. The lead 20 can be configured so that the MCSMs extend substantially the entire length of the conductor as a series of continuous coils of adjacent CSMs. The leads 20 can be connected to electrodes and be bipolar for some cardiac applications. A distal and/or proximal end of the lead may include a short length of straight or single layer coil that connects to an electrode. To aid in maintaining coiled CSMs in position or to inhibit unwinding/movement of a coil, a small piece or length of heat-shrink tubing (e.g., about 10 mm or less of PET heat shrink tubing) can optionally be placed at different conductor coil segments and heated to compress the conductor against the liner/mandrel to hold the conductor in position.

In addition, in some particular embodiments, the third layer can be formed so that most of the revolutions are at a tight pitch, e.g., 78 revolutions at a pitch of about 0.2 in to end at a few last revolutions, e.g., 5-15 revolutions at a larger pitch such as about 0.7 in for easier electrode installation/connection.

A lead 20 incorporating this FIG. 22A CSM 8 design was prototyped and tested with two 0.007" diameter DFT conductors (with insulation), e.g., wires/filars with silver core, 19 filar cable, 0.005" cable OD and 0.001" wall ETFE insulation, with conductors cowound parallel to each other and coiled in two layers. The first layer (coiled forward section) has an inner diameter of 0.023" and a pitch of 0.05", the second layer (coiled back section) is coiled in the space/pitch of the first layer; and the third final layer (coiled forward section) is on/over the first and the second layers. This CSM had an impedance of over 200 ohms at 64 MHz and length of between about 5 cm and 5.7 cm. The details of the windings are as listed in Table II below.

TABLE II

EXEMPLARY TWO-LAYER CSM

| Layer # | Winding Direction | Direction of rotation | Pitch | Length | Comments |
|---|---|---|---|---|---|
| Winding #1 | Left to Right | Clockwise (CW) | 0.050" | 5.7 cm | Layer # 1 |
| Winding #2 | Right to left | Counter Clockwise (CCW) | 0.050" | 5.7 cm | Layer # 1 |
| Winding #3 | Left to Right | Counter Clockwise (CCW) | 0.020" | 5.7 cm | Layer # 2 |

To form the next adjacent CSM, the winding can continue in the CCW direction (left to right) and the backward section can be coiled in the CW direction (right to left), followed by the other forward section also in the CW direction (left to right). That is, the conductor changes the coiling rotation direction once per CSM and each adjacent CSM alternates the rotation direction of the different FS, BS, FS segments (e.g. CSM module one, CW, CCW, CCW, CSM module two, CCW, CW, CW, module 3, CW, CCW, CCW . . . ). As the conductor 3 exits the upper forward section it continues on to form the lower forward section of the next adjacent CSM 8.

Figure 26:
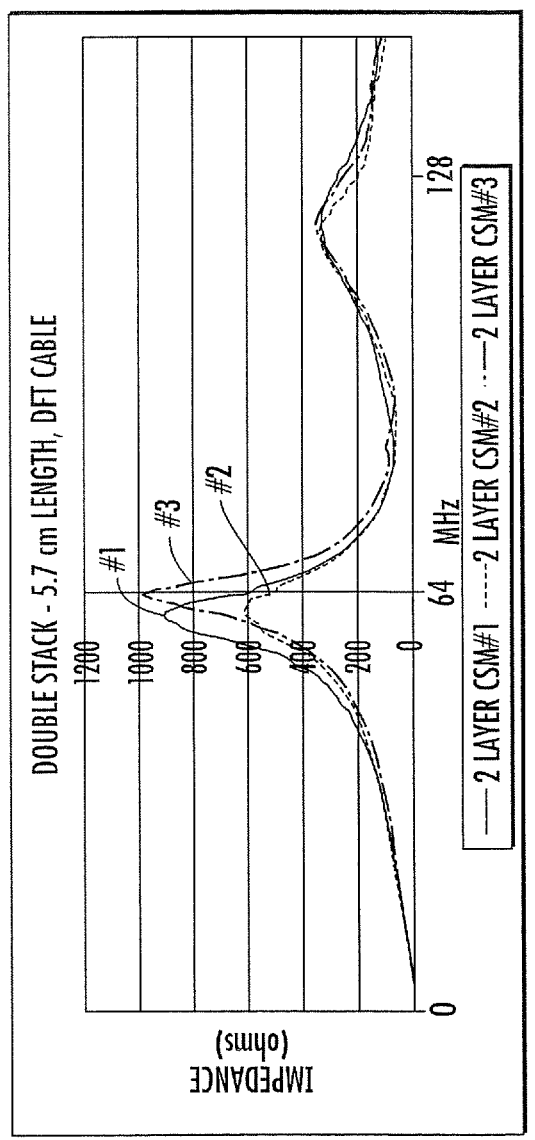
FIG. 26 is a graph of impedance (Ohms) versus frequency (MHz) of a lead having spaced apart (in the lengthwise direction) two layer current suppression modules (CSMs) configured as described in FIG. 22A.
Figure 27:
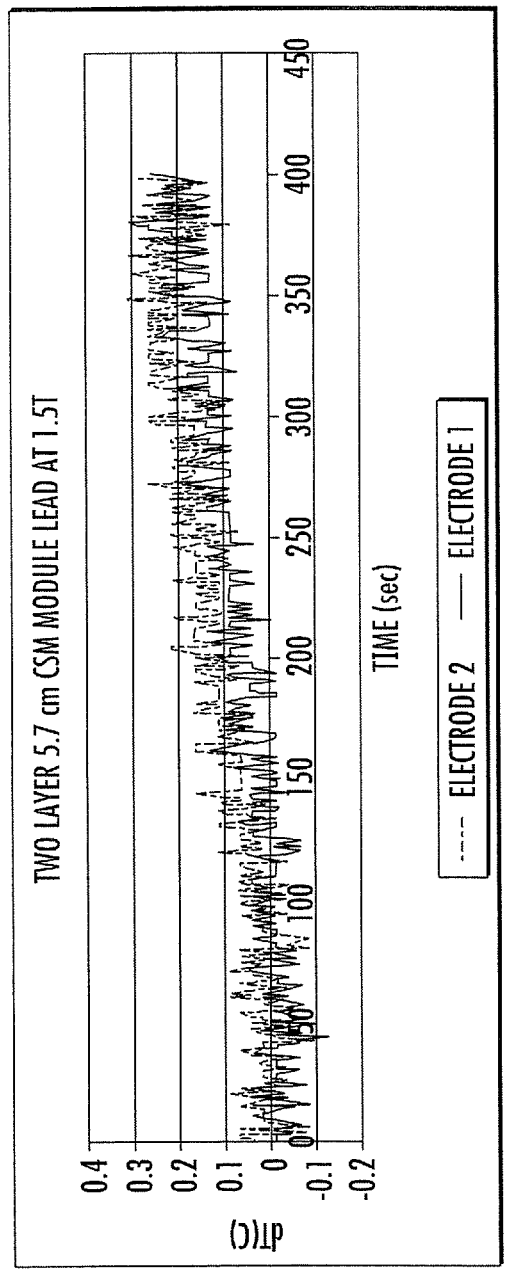
FIG. 27 is a graph of temperature change (C) versus time (seconds) of a lead of about 61 cm with two conductors, each having about 12 two-layer stacked CSM segments having a length of about 5.7 cm. The temperature/time data was obtained for the lead in gel phantom in a 1.5 T MR Scanner at an SAR of the pulse sequence of 4.3 W/Kg.

The electrical impedance of this 5.7 cm CSM 8 is shown in FIG. 26. A lead 62 cm long incorporating 11 CSMs 8 along the length of the lead 20 (analogous to FIG. 23) was prototyped and tested. Heat test results from this lead show less than 2° C. temperature rise in the simulated tissue (gel) adjacent to the electrodes in 1.5 T field strength MRI scanner with 4.3 W/kg peak input SAR (FIG. 27).

FIGS. 28A and 28B are schematic cross-sectional views of a conductor 3 in the plane of its long axis with a multi-layer coiled CSM configuration 8*m*. FIG. 28A corresponds to the first layer of a two-layer configuration such as that shown in FIG. 22A. FIG. 28B corresponds to the three separate layers of a three-layer configuration such as shown in FIG. 21A.

Figure 29A:
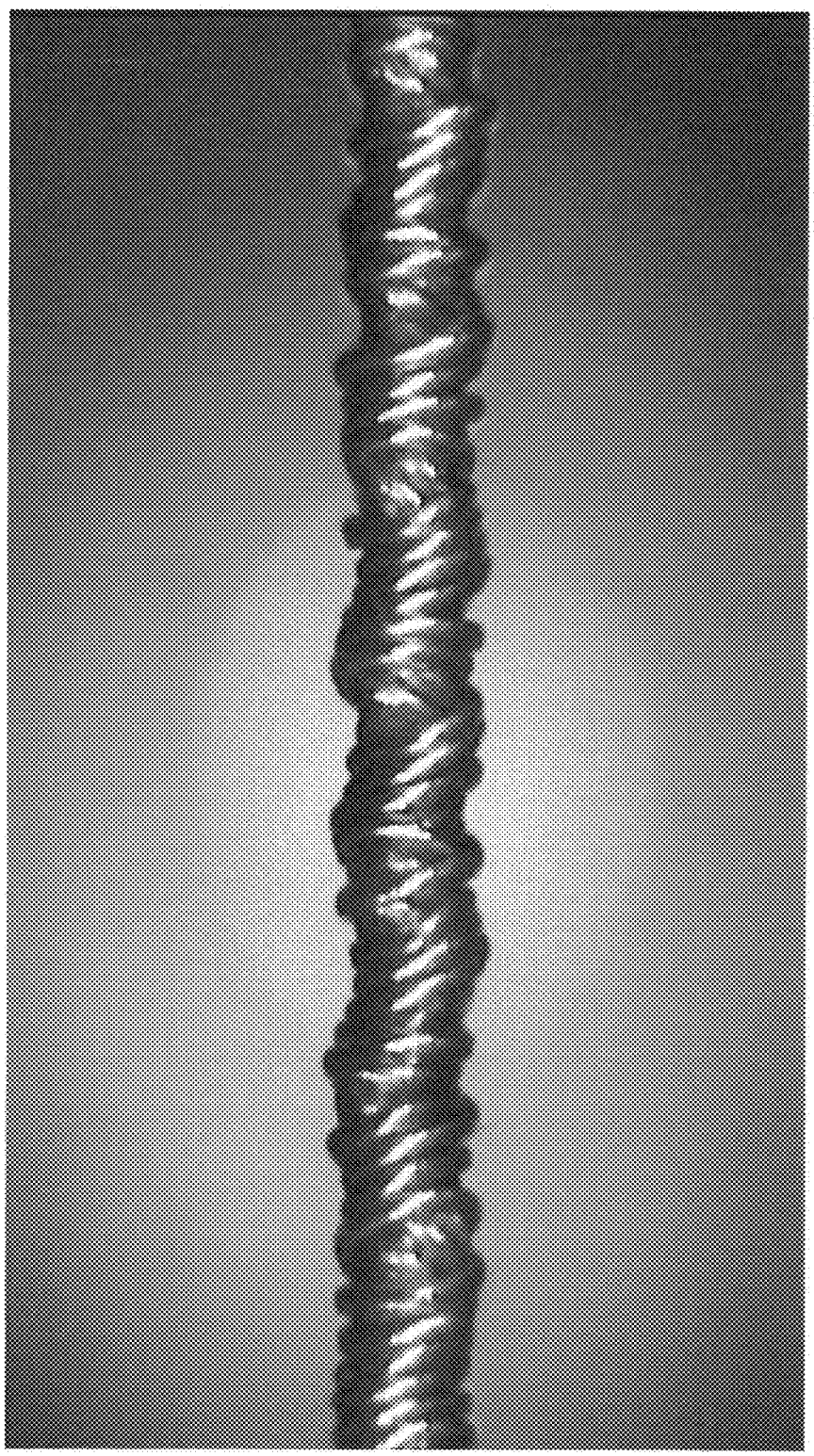
FIGS. 29A and 29B are greatly enlarged digital photographs of a portion of a two conductor lead having a stacked (three layer) CSM configuration according to embodiments of the present invention.
Figure 29B:
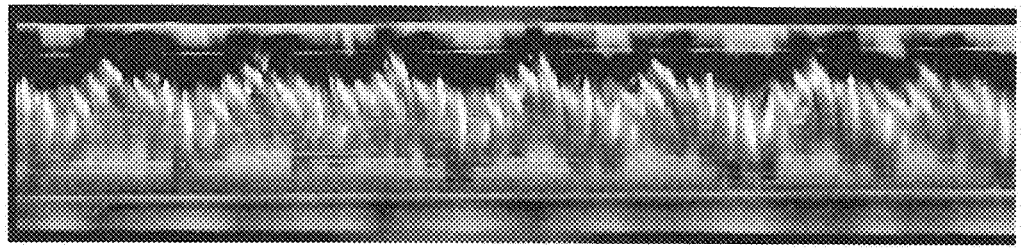
Figure 29C:
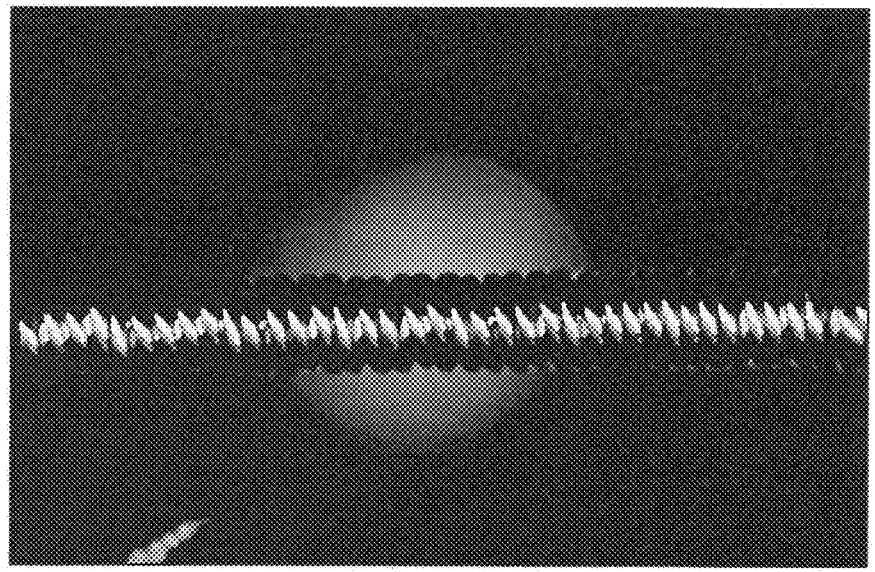
FIGS. 29C and 29D are greatly enlarged digital photographs of a portion of a two conductor lead having a stacked (two layer) CSM configuration.
Figure 29D:
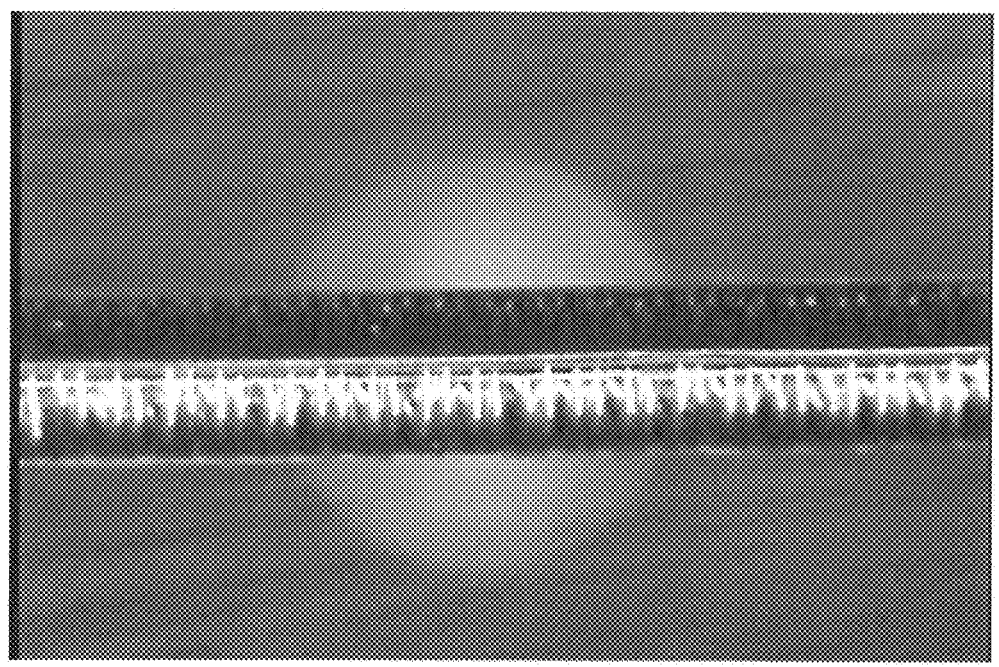

FIGS. 29A and 29B are enlarged digital images of a multi-conductor lead 20 having conductors 3 in substantially continuously arranged triple stacked layers of coils forming a CSM 8*m* according to embodiments of the present invention. FIG. 29B illustrates an outer encasement layer that defines a substantially constant outer diameter over the flexible lead with the stacked CSMs 8*m*. FIGS. 29C and 29D are digital images of an enlarged multi-conductor lead 20 having conductors 3 in substantially continuously arranged double stacked layers of coils forming a CSM 8*m* according to embodiments of the present invention. FIG. 29D illustrates an outer encasement layer that defines a substantially constant outer diameter over the flexible lead with the stacked CSMs 8*m*.

The exemplary coil diameters, coil lengths, and conductor lengths can have a significant range of values within the scope of the invention, typically with a primary design parameter being that of wavelength noted above. While embodiments of the invention have been illustrated in the context of MRI exposure at 64 MHz (1.5 T MRI) and 128 MHz (3 T MRI), it is intended that applications of the present invention to MRI shall include MRI over the full range of RF afforded by MRI scanners, including, for example, 0.1, 0.3, 0.7, 1.0, 1.5, 2.5, 3, 4, 4.7, 7 and 9.4 Tesla (T) systems, especially commercially available scanners such as, 1.5 T scanners, 3 T scanners (128 MHz), 1 T scanners (42 MHz), 0.5 T scanners (21 MHz), 4 T (170 MHz) and 7 T (300 MHz) scanners.

It is also contemplated and included in the present invention that embodiments involving implanted leads include the use of biocompatible materials and/or coatings, and the conductors 3 include aluminum, gold, silver, platinum, rhodium, iridium, rare earth metals, alloys of these and other conducting metals including Nickel Titanium alloys (e.g., nitinol, MP35N, etc.), and conductors formed from coatings of metals, for example, gold coated nitinol, or nitinol or MP35N, etc. with a silver or Pt core, etc., such as, for example drawn tubing formed of MP35N available from Ft. Wayne Industries located in Ft. Wayne, Ind., USA.

For implantable leads 20, the designs can be configured to have the mechano-chemical properties of flexibility, strength, durability, resistance to fatigue, non-corrodible, non-toxic, non-absorbent, and bio-compatible and/or bio-inert. It is further contemplated that embodiments of the invention can be used in any of a range of applications where implanted conducting leads (or external or combinations of same) are required, including but not limited to: connections to IPGs, DBS electrodes, cardiac pacemakers, cardiac electrodes, nerve stimulators, electrodes, EEG and EKG monitors (devices with either or both internal and external leads), cardiac defibrillators, power sources and/or control lines for artificial limbs, power sources and/or control lines for artificial organs (kidneys, etc); power sources and/or control lines for implanted bio-substrates or enzyme delivery devices (e.g., insulin delivery) or other drug delivery devices, and the like.

Figure 30A:
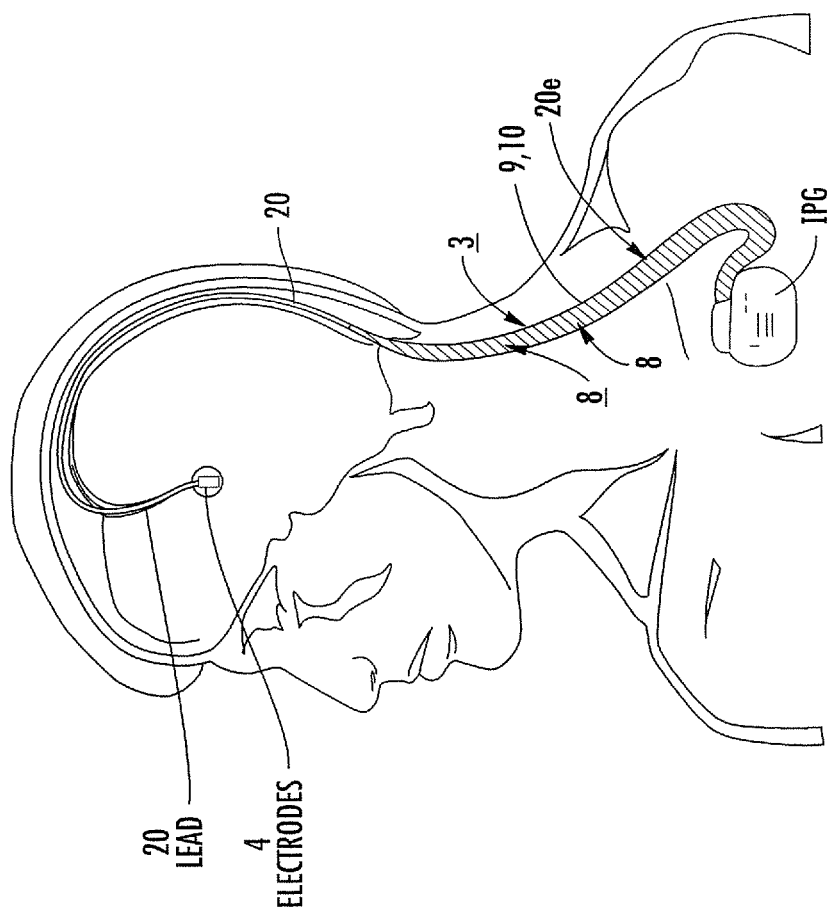
FIG. 30A is a schematic illustration of a DBS system with at least one lead, IPG and electrodes according to some embodiments of the present invention (the DBS system includes two leads and two IPGs).
Figures 30B, 30C:
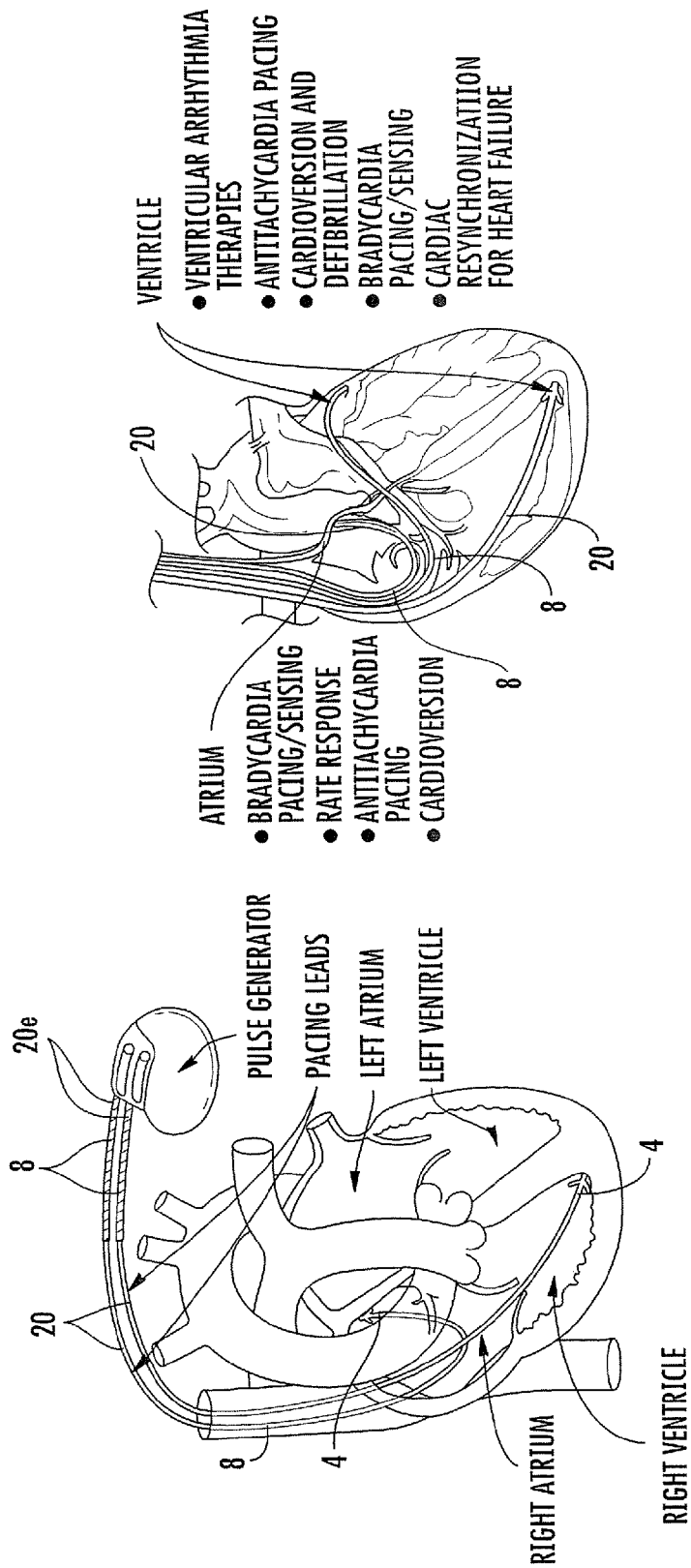
FIGS. 30B and 30C are schematic illustrations of therapeutic systems with leads in communication with a cardiac pulse generator.

FIG. 30A is a schematic illustration of a DBS system with at least one lead (typically two leads) with CSMs 8 and an IPG and electrodes 4 according to some embodiments of the present invention. Optionally, as shown in FIG. 30A, the proximal portion of the lead 20e can be reinforced and/or larger (thicker) than the distal portion. This larger portion 20e can be integral on a single lead or may be provided as a matable/connecting lead extension. The proximal end portion 20e can have a length of between about 2-15 cm, typically between about 5-10 cm. The larger portion/extension 20e can provide increased fatigue or torque resistance or other structural reinforcement proximate a rigid body, such as, for example, an IPG. The proximal portion or lead extension 20e can include one or more CSMs 8 or may not include any CSMs 8. Alternatively, the lead extension 20e may include a differently configured CSM 8 and/or a less dense CSM arrangement (less CSMs per cm) relative to the distal portion of the lead 20. FIGS. 30B and 30C are schematic illustrations of therapeutic systems (medical devices) with leads connected to a cardiac pulse generator. FIG. 30B illustrates the system can include two leads, extending to the right auricle (RA) and right ventricle (RV), respectively, while FIG. 30C illustrates that the cardiac system can have three leads (one each in the RV, RA and left ventricle, LV). FIG. 30B also illustrates that the distal end portion of the lead 20e may have a larger (thicker) and/or reinforced configuration relative to the more flexible distal end portion as discussed with respect to FIG. 30A. Again, the proximal end 20e can have a length between about 2-15 cm, typically between about 5-10 cm.

Figure 30D:
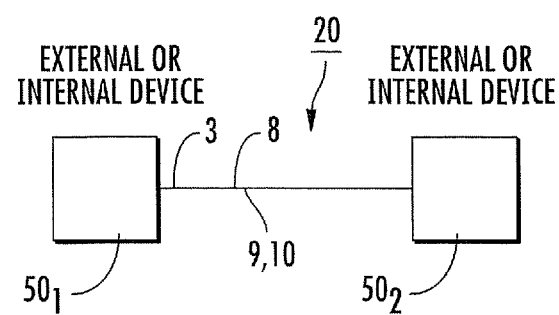
FIG. 30D is a schematic illustration of a lead that connects two internal or external devices according to embodiments of the present invention.

FIG. 30D schematically illustrates that the lead system 20 interconnects two electronic devices $50_1$, $50_2$ residing either inside or external to a human or animal body. In some embodiments, the devices can be non-medical devices, such as communication devices. In other embodiments the devices can be medical devices. For example, at least one end portion of the at least one conductor 3 connects an electrocardiographic electrode $50_1$ and at least another end is connected to an electrocardiographic monitoring device $50_2$. In other embodiments, at least one end portion of the at least one conductor 3 is connected to an electroencephalographic graphic electrode $50_1$ and at least another end is connected to an electroencephalographic monitoring device $50_2$. In still other embodiments, at least one end portion of the at least one conductor 3 is connected to a blood pressure monitoring transducer $50_1$ and at least another end is connected to a blood pressure monitoring device $50_2$. In yet other embodiments, at least one end portion of the at least one conductor 3 is connected to a blood oxygen monitoring transducer $50_1$ and at least another end is connected to a blood oxygen monitoring device $50_2$.

Figure 30E:
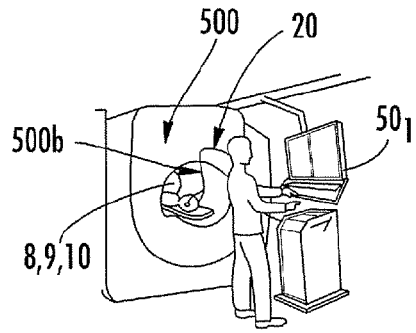
FIGS. 30E-30G are schematic illustrations of cables that extend within a bore of an MR Scanner can be configured with the current suppression modules according to embodiments of the present invention.
Figure 30F:
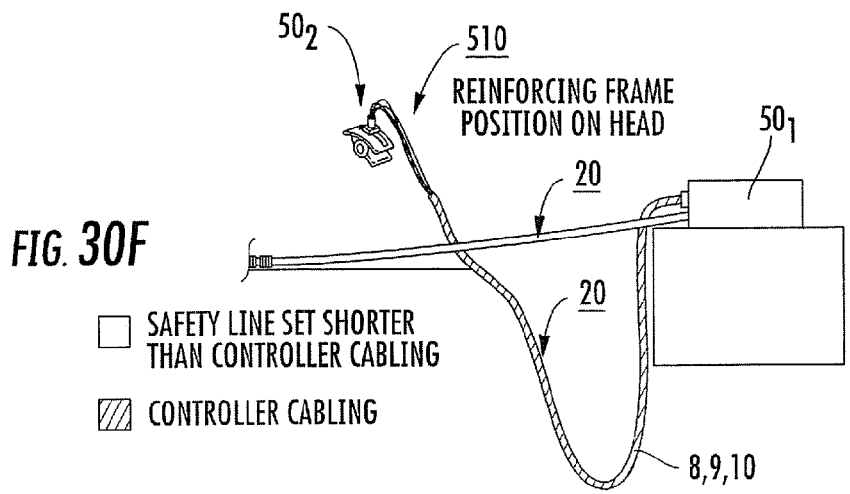
Figure 30G:
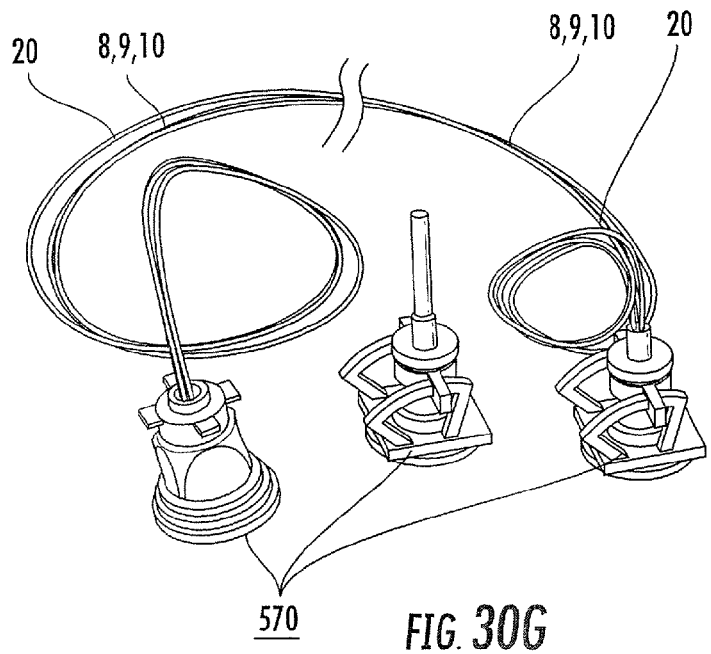

FIG. 30E is a schematic illustration of an MR Scanner 500 with a high-field magnet bore 500b. In some embodiments, the lead 20 can be configured to extend inside the bore 500b during some interventional or diagnostic procedures. The lead 20 can be a cable, extension or guide that manipulates a device such as a robotic or remotely operated tool or other device. The lead 20 can connect an external control unit $50_1$ to an adjustable or moveable component or tool $50_2$ inside the magnet bore 500b. The lead 20 can be torqueable, e.g., rotate to turn or manipulate input or surgical devices or tools. The lead 20 can include at least one cable or conductor with at least one CSM 8 with a respective at least one FS and BS 9, 10. FIG. 30F illustrates that the tool $50_2$ can be an adjustable trajectory frameless head mount 510 that can be used to adjust the trajectory of the implantable lead to place and implant DBS leads using MR guidance while the patient remains in the magnet bore 500b. FIG. 30G is an example of one surgical tool, a frameless head mount 510, with cables or leads 20 configured with at least one CSM 8 according to embodiments of the present invention.

Described below are exemplary designs that can be implemented on any lead, including, for example, cardiac leads, such as bradyarrythmia and tachyarrhythmia or ICD lead systems. Although shown with electrodes, the configurations can be used with other elements or with just a lead or cable, as appropriate to the application. The RF/MRI safe leads 20 can include one or more conductors 3 of the lead arranged in multiple CSMs 8 where each CSM has a length of between about 1.5 cm to about 6 cm, and each CSM 8 is arranged such that it has impedance exceeding about 100 ohms at target MRI frequencies (for example, 128 and 64 MHz).

FIGS. 31A, 31B, 32A and 32B are schematic illustrations of leads that are described as particularly suitable for bradyarrythmia and tachyarrhythmia or ICD lead systems, for which it is desirable to render MRI-safe and/or RF safe, according to embodiments of the present invention These leads and/or features thereof can be modified to fit other applications as well. The leads 20 may include different tissue fixation configurations such as, for example, passive fixation or active fixation. In passive fixation the distal end of the lead is anchored in the folds of the cardiac tissue. In active fixation, the distal end of the lead is a helical screw, which is fixed in the cardiac tissue.

Bradyarrythmia leads or pacemaker leads (FIGS. 31A, 31B) typically have two electrodes 4, a distal pacing and sensing electrode 31, and the proximal ground electrode 33. The conductors 3 connecting the distal electrodes 31 and 33 to IPG contact electrodes 35 and 36, are typically cowound/coiled along the length of the lead 20. In passive fixation leads, the distal electrode 31 may be a conductive contact; whereas in active fixation leads this contact can be a helical screw 37 which can be torqued and turned by turning the proximal end of the coiled conductor via electrode 36.

Tachyarrhythmia leads (FIGS. 32A and 32B) typically have three electrodes; distal pacing and sensing electrode 31, and two proximal shocking electrodes 38 and 40. The conductor 3 connecting the distal electrode is coiled along the length of the lead, and is in the center of the lead. The shocking coils are cowound coils of non-insulated conductors, and are connected to the proximal electrodes/IPG by conductors 39 and 41.

Figure 33:
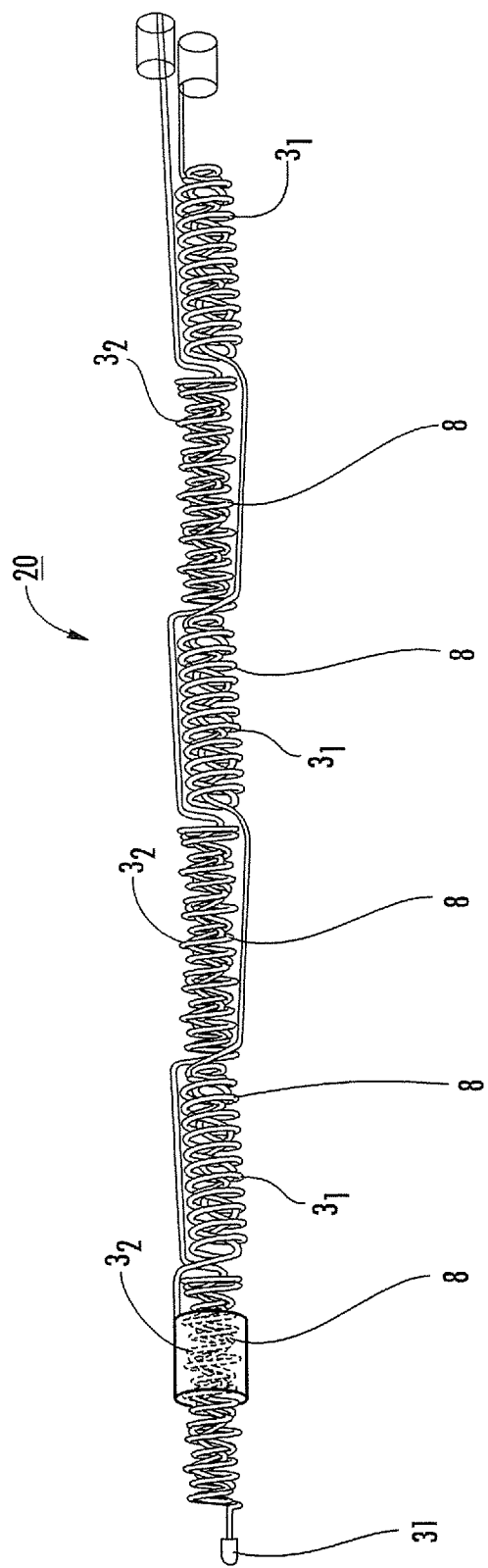
FIG. 33 is a schematic illustration of a multi-conductor lead configurations according to some embodiments of the present invention.

Now in accordance with embodiments of the present invention, conducting leads of the tachyarrhythmia, bradyarrythmia, ICD (implantable cardio-defibrillator) and/or pacing lead system may be formed with CSMs 8 or with CSMs and shield elements to suppress induced RF currents and improve the safety of such devices during MRI, as exemplified in FIGS. 33-44 and FIGS. 55A-58B. Thus, FIG. 33 illustrates a lead 20 with a passive fixation bradyarrythmia lead design with two conductors $3_1$, $3_2$, each conductor is wound in CSMs 8 and arranged along the length of the lead one conductor $3_1$, alternating the other $3_2$. Each conductor has CSMs 8 formed along the length and spaced intermittently. When the lead is assembled, the CSMs of each conductor are interleaved/alternated along the length of the lead. The straight sections of the conductors will typically overlap the CSMs of other conductors. Conductors $3_2$ and $3_1$ connecting to the distal electrode 4 and distal ground electrode 31, respectively, are wound in CSMs 8 which are spaced apart from each other. When the lead 20 is assembled, the CSMs 8 of the two conductors $3_1$, $3_2$, alternate.

FIGS. 34 and 35 show embodiments with two conductors $3_1$, $3_2$, with multiple CSMs 8 along the length of the lead 20; with one conductor $3_1$ CSM assembly substantially concentric to the other $3_2$. The CSMs 8 of the conductors $3_1$, $3_2$, have inner and outer diameters such that they can be concentrically arranged along the length of the lead. One conductor CSM assembly, for conductor $3_2$ can rotate with respect to the other, i.e. in CSM assembly for conductor $3_1$. The CSMs 8 of the conductors $3_2$ and $3_1$ have inner and outer diameters such that they can be concentrically arranged along the length of the lead. One conductor 8 CSM $3_2$ assembly can rotate with respect to the other $3_1$. The center conductor CSM assembly 32 is connected to the fixation helix 37 at the distal end. The fixation helix 37 can be manipulated by torquing the center conductor CSM assembly $3_2$ and this in turn rotates and laterally slides the fixation helix 37 in and out of the lead 20 allowing anchoring in the cardiac tissue.

Figure 36:
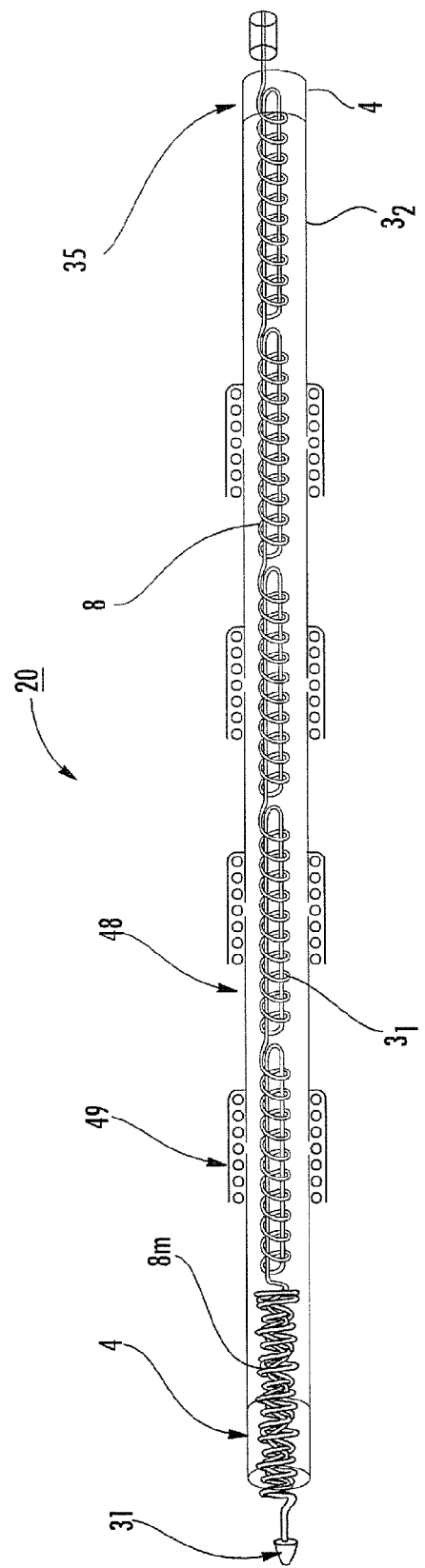
FIG. 36 is a schematic illustration of yet another lead configuration with stacked reverse and forward segments of adjacent lengths of a single conductor forming a respective current suppression module and with an RF trap shield layer according to embodiments of the present invention.

FIG. 36 shows a passive fixation bradyarrythmia lead embodiment with distal electrode conductor 3 wound in trilayer CSMs 8m along the length of the lead and is in the center of the lead 20. The proximal connecter is connected to the IPG by means of a RF high impedance shield layer 48 with RF traps 49 and the shield layer can shield the inner conductor 3 and CSM 8m thereof. The conductor $3_1$ connecting to the distal electrode may be arranged along the length to have one or more CSMs. The conductor $3_2$ connecting the proximal electrode is a high impedance shield 48 incorporating RF traps 49 along the length of the shield. The impedance of the RF trap can typically exceed about 300 ohms and one or more traps can be placed along the length of the lead.

Figure 37:
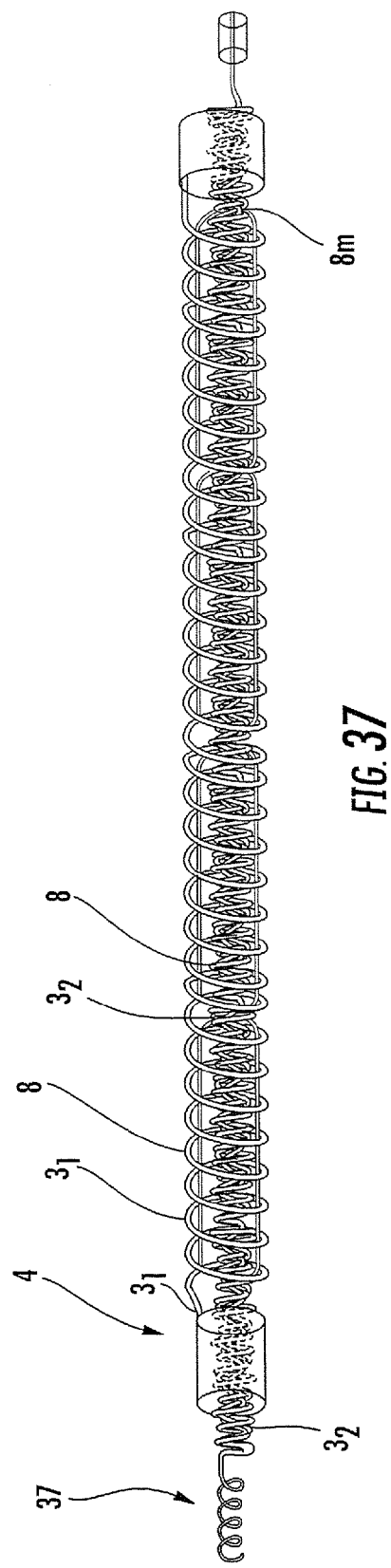
FIG. 37 is a schematic illustration of a lead with at least one inner conductor configured to rotate substantially freely with respect to the lead body according to embodiments of the present invention.

FIG. 37 shows an embodiment of the invention in an active fixation bradyarrythmia lead 20 with distal electrode conductor $3_1$ wound in trilayer CSMs 8m along the length of the lead and is in the center of the lead, and this conductor $3_1$ can rotate freely with respect to (WRT) the lead body. The proximal electrode conductor $3_2$ is arranged in CSMs 8 and is substantially concentrically outside the distal electrode conductor $3_1$.

Figure 38:
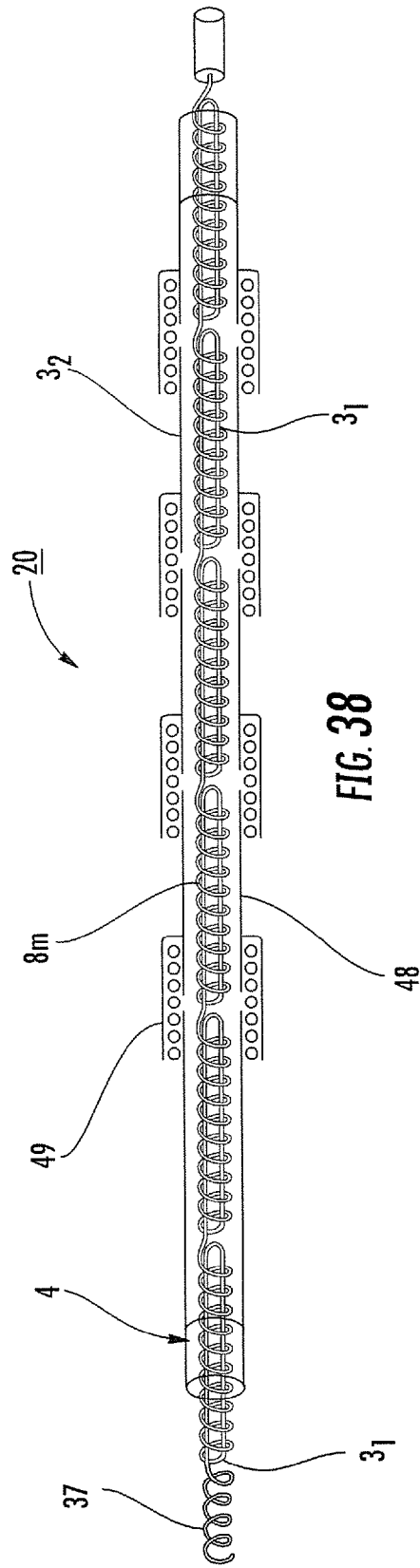
FIG. 38 is a schematic illustration of a lead similar to that shown in FIG. 37 but with the proximal electrode conductor comprising an RF trap(s) along the length of the lead according to some embodiments of the present invention.

FIG. 38 shows an active fixation bradyarrythmia lead 20 with distal electrode conductor $3_1$ wound in trilayer CSMs 8m along the length of the lead and is in the center of the lead, and rotates freely WRT the lead body. The proximal electrode conductor $3_2$ is arranged as an RF trap 49 along the length of the lead and can provide a shield 49 for the inner conductor $3_1$. The center conductor CSM assembly $3_1$ is connected to a helical fixation screw 37 at the distal end. The proximal electrode is connected to the IPG via a high impedance shield 48 with RF traps 49 as discussed with respect to FIG. 37. The inner conductor assembly $3_1$ can be rotated WRT the outer shield 49, by rotating the proximal electrode. This also rotates and drives the fixation screw 37 laterally, thus anchoring in the cardiac tissue.

Figure 39:
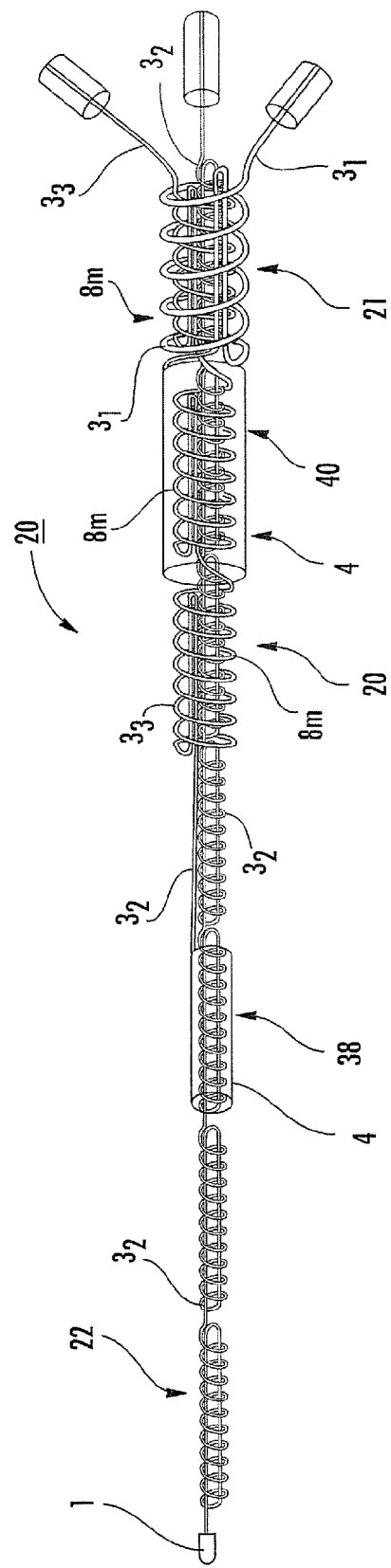
FIG. 39 is a schematic illustration of a lead comprising three conductors with some cowound with others to form at least some current suppression modules for respective conductors according to some embodiments of the present invention.

FIG. 39 illustrates another (passive fixation) tachyarrythmia lead 20 where three conductors $3_1$, $3_2$, $3_3$ are cowound to form CSMs 8. One is connected to the sensing electrode 40, other two to the shocking electrodes 4 (38). The three conductors $3_1$, $3_2$ and $3_3$ are cowound and multiple CSMs 8 along the length in the proximal section, in the mid section (between two stimulation electrodes 38 and 40) two conductors $3_3$ and $3_2$ are cowound to form some CSMs 8, and in the distal part only the distal electrode conductor $3_2$ is arranged to form CSMs 8.

Figure 40:
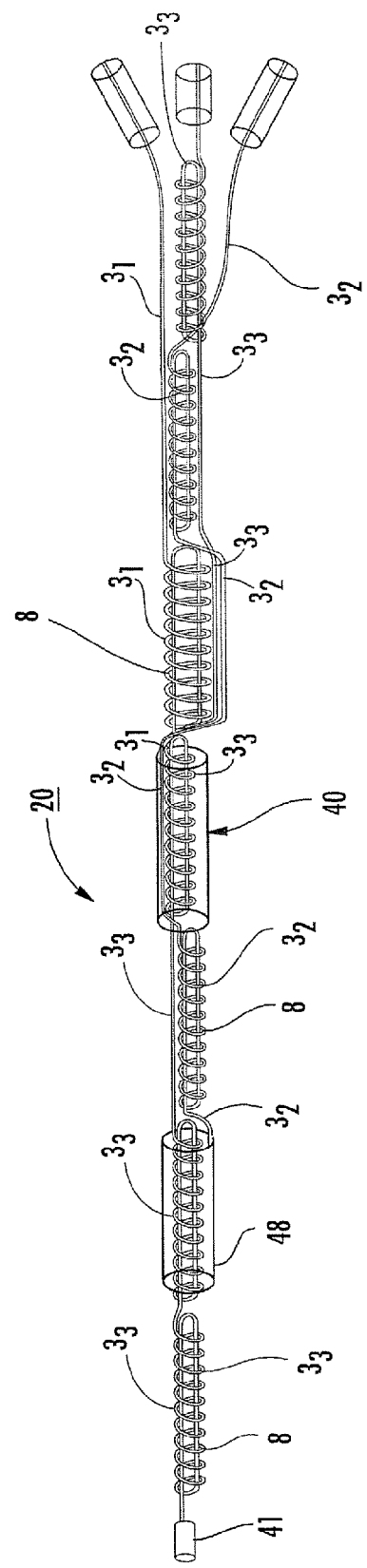
FIG. 40 is a schematic illustration of a lead with multiple conductors having multiple respective current suppression modules spaced apart along the length of the lead according to some embodiments of the invention.

FIG. 40 illustrates a (passive fixation) tachyarrythmia lead where the three conductors $3_1$, $3_2$, $3_3$ are arranged to have CSMs 8 along the length of the lead 20 and the three conductors $3_1$, $3_2$, $3_3$ alternate CSM 8 locations along the length of the lead. CSMs 8 are placed discontinuously or intermittently along the length of each conductor 3. In the distal section the sensing electrode conductor and the distal shocking electrode conductor $3_2$, $3_3$, respectively, are alternated, in the proximal section the CSMs 8 on all the three conductors $3_1$, $3_2$, $3_3$ are alternated. This design may reduce the coupling of the distal electrode conductor $3_3$ with the stimulation or shocking conductors $3_1$, $3_2$ during the shock-defibrillation operation of the ICD.

Figure 41:
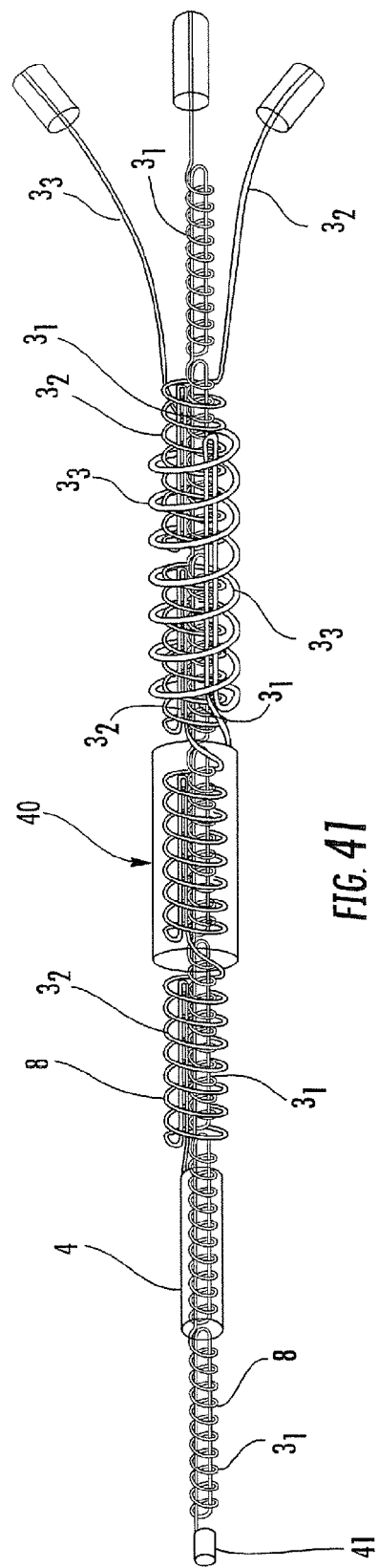
FIG. 41 is a schematic illustration of yet another lead configuration with multiple conductors, each having current suppression modules, with a distal electrode conductor being substantially concentric to and/or inside the shock/stimulation electrode conductors according to some embodiments of the present invention.

FIG. 41 shows a (passive fixation) tachyarrythmia lead 20 where the three conductors $3_1$, $3_2$, $3_3$ are arranged to have CSMs 8 along the length of the lead 20 and the distal electrode conductor $3_1$ is in the center of the lead and concentric to the shocking electrode conductors $3_2$, $3_3$. This design may reduce the coupling of the distal electrode conductor with the shocking conductors during the shocking operation of the ICD.

Figure 42:
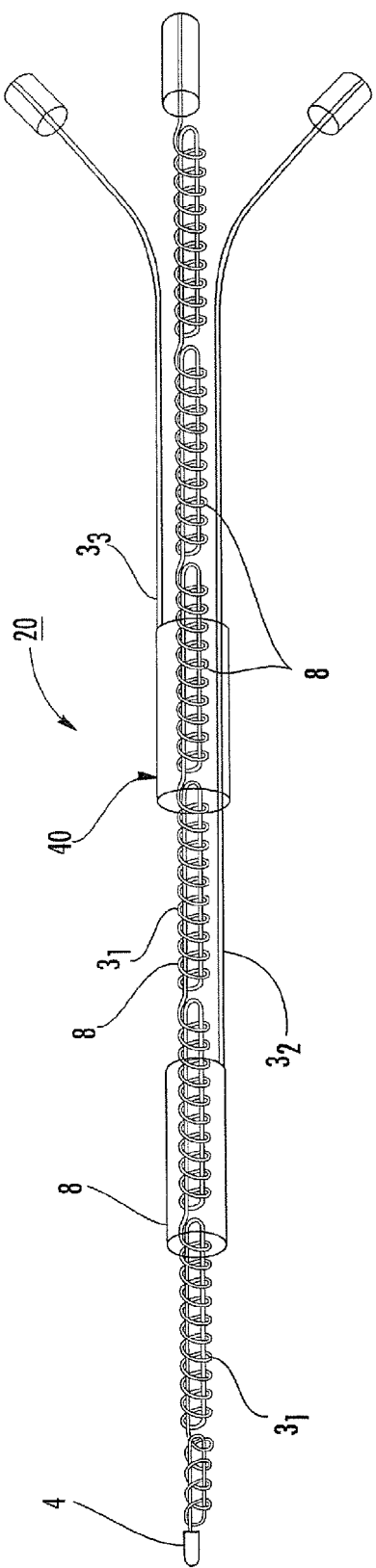
FIG. 42 is a schematic illustration of another lead configuration where the distal electrode conductor comprises current suppression modules but one or more of the other conductors may be substantially straight according to embodiments of the present invention. As shown, the lead may be particularly suitable as a passive fixation tachyarrhythmia lead.

FIG. 42 illustrates a (passive fixation) tachyarrythmia lead 20 where the distal electrode conductor $3_1$ is arranged to have CSMs 8 along the length of the lead 20 and the shocking electrode conductors are straight along the length of the lead.

Figure 43:
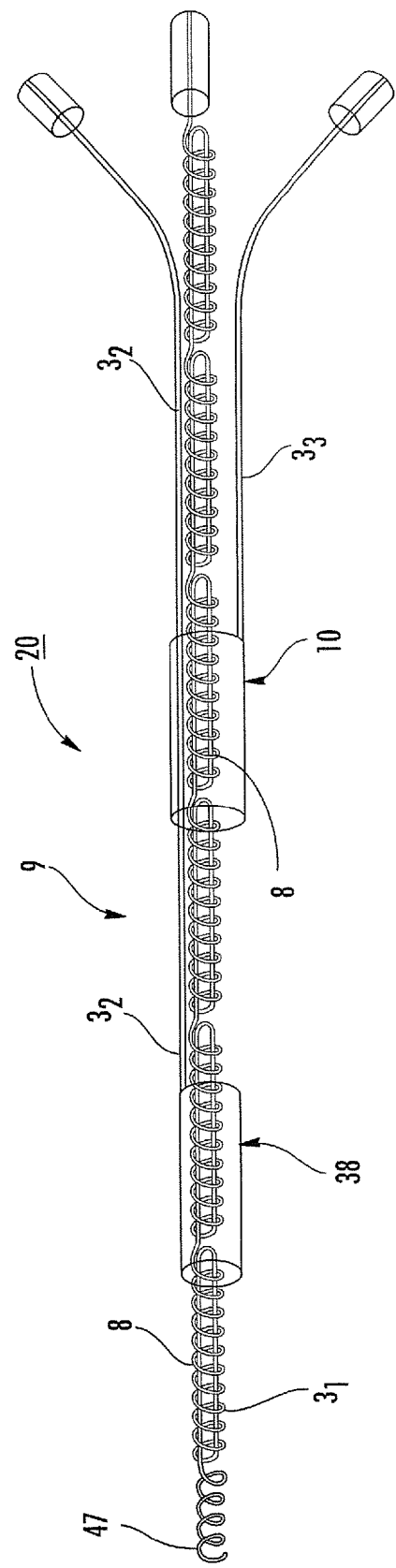
FIG. 43 is a schematic illustration similar to FIG. 42, but with the end configured as an active fixation end according to embodiments of the present invention. This configuration may be particularly suitable as an active fixation tachyarrhythmia lead.

FIG. 43 illustrates an active fixation tachyarrythmia lead 20 where the distal electrode conductor $3_1$ is arranged to have CSMs 8 along the length of the lead 20 and the stimulation/shocking electrode conductors $3_2$, $3_3$ are substantially straight along the length of the lead 20.

Figure 44:
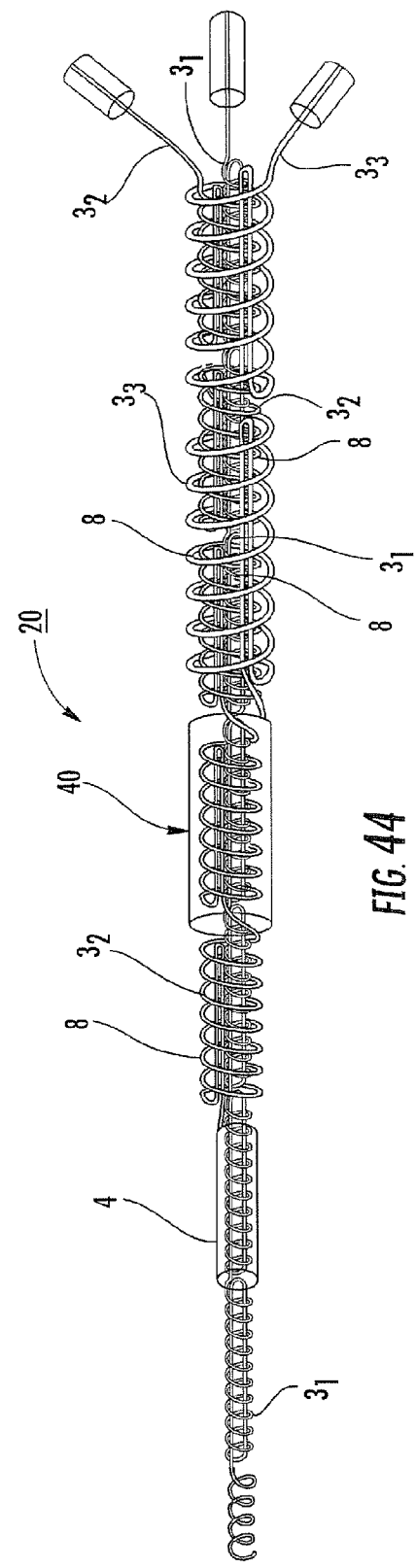
FIG. 44 is a schematic illustration of another lead configuration with multiple conductors where each conductor includes current suppression modules spaced apart along its length according to embodiments of the present invention. This lead configuration may be particularly suitable as an active fixation tachyarrhythmia lead.
Figure 45C:
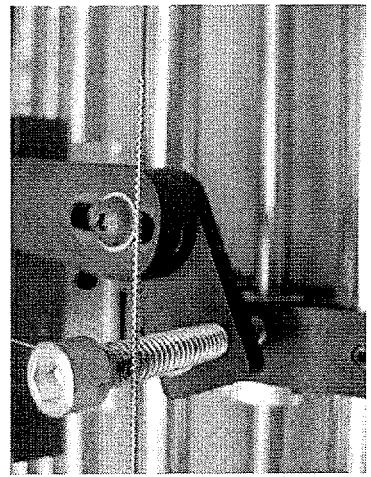
FIGS. 45A-E are images of a winding sequence for fabricating a tri-layer current suppression module using a coil winder (shown with two cowound conductors) according to some embodiments of the present invention.
Figure 45B:
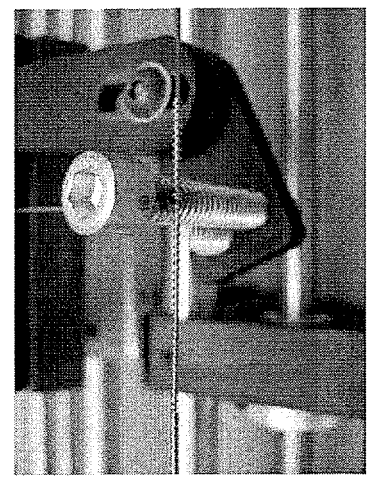
Figure 45A:
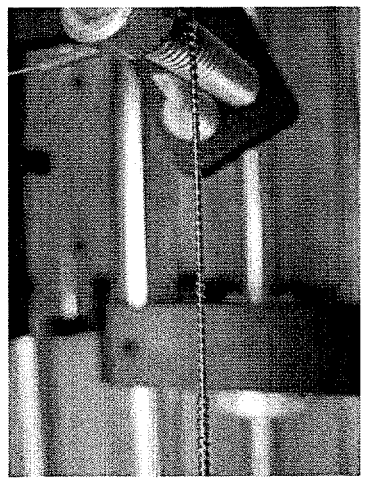
Figure 45E:
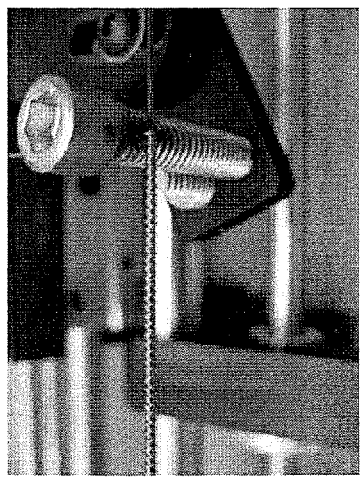
Figure 45D:
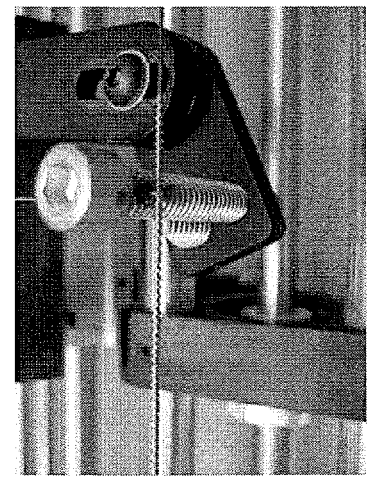
Figure 46A:
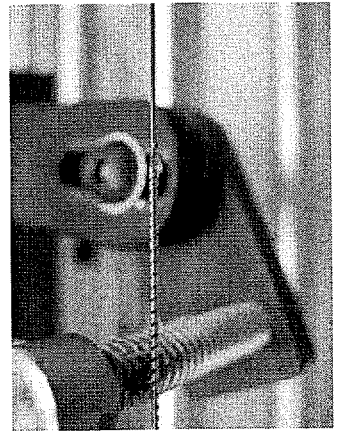
FIGS. 46A-46F are images of a winding sequence for fabricating a two layer current suppression module using a coil winder according to some embodiments of the present invention.
Figure 46B:
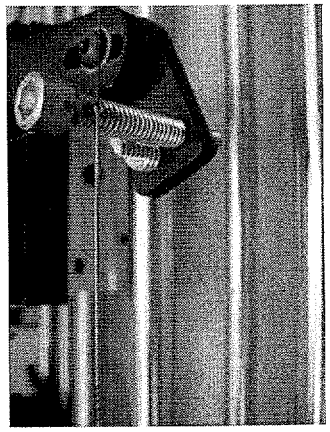
Figure 46C:
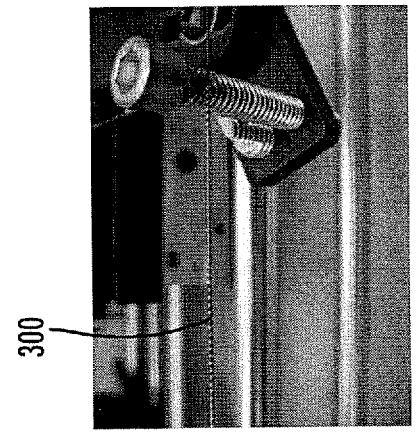
Figure 46D:
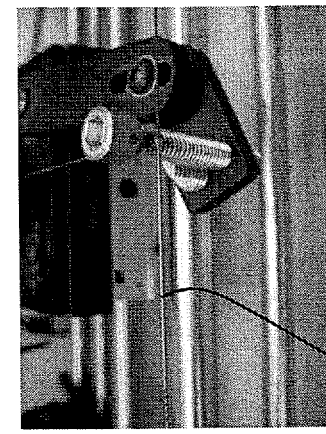
Figure 46E:
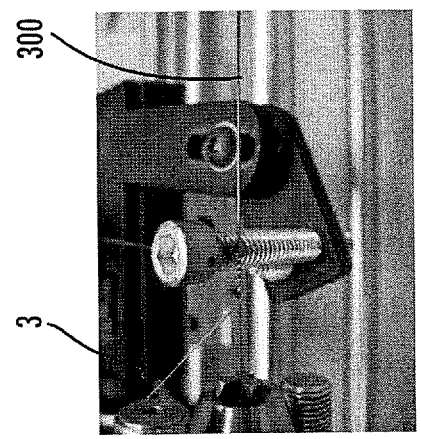
Figure 46F:

FIG. 44 shows an active fixation tachyarrythmia lead 20 where the distal electrode conductor $3_1$ is arranged to have CSMs 8 along the length of the lead 20 and the shocking electrode conductors $3_2$, $3_3$ are arranged so as to have CSMs 8 along the length of the lead.

In some embodiments, the cardiac leads can be configured with shocking electrodes used in ICD leads, the conventional shocking electrodes, which are conventionally 4-5 cm long and comprise a wound conductor may need modification for MRI compatibility. This conductor may be longer than λ/4 at MRI frequencies and may add to temperature rise in the tissue adjacent to the coils. The shocking coils can be electrically reduced in length and this may be achieved by using a flexible stent-like design instead of a coil, e.g., using a sinusoidal helix where one segment is interconnected with other so as to reduce the electrical length of the shocking electrode.

In particular embodiments, every or some alternate CSMs 8 may be wound in opposite directions to suppress currents induced in the lead by alternating magnetic fields and potential nerve stimulation.

The conductor configurations can be used for any lead used during an interventional procedure and/or for any medical device, whether implantable or not and whether for chronic or acute use.

Figure 55A:
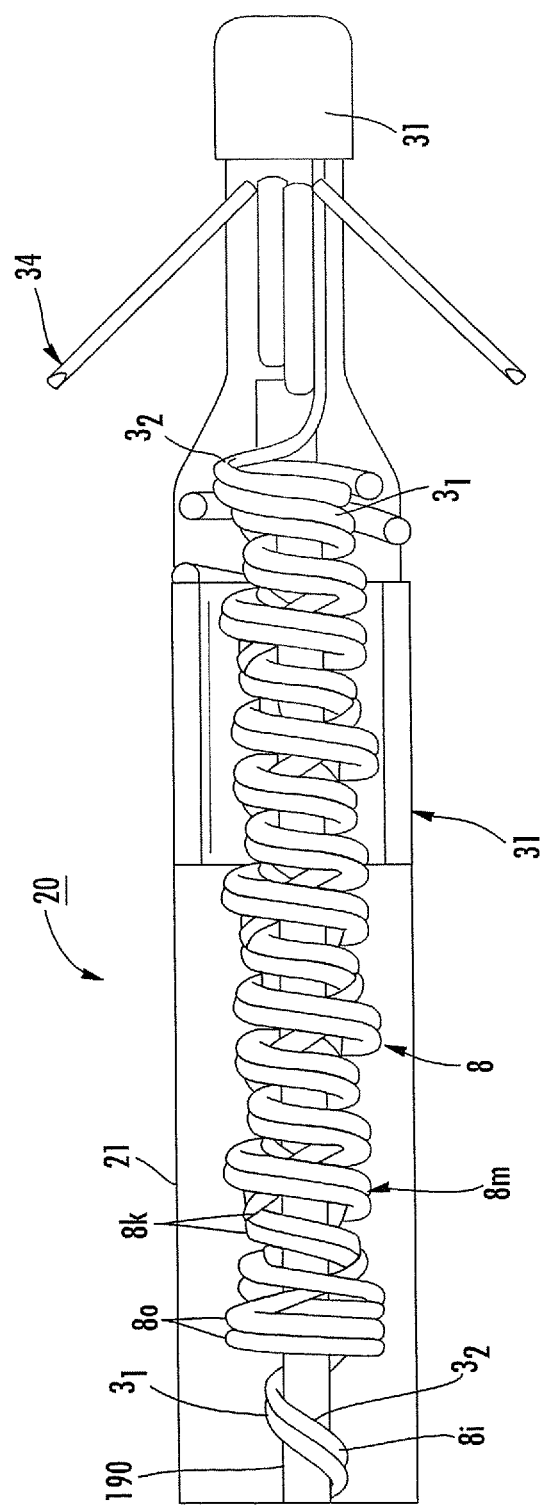
FIG. 55A is a side view of a portion of a lead that may be suitable to be a passive fixation pacemaker lead according to embodiments of the present invention.
Figure 55B:
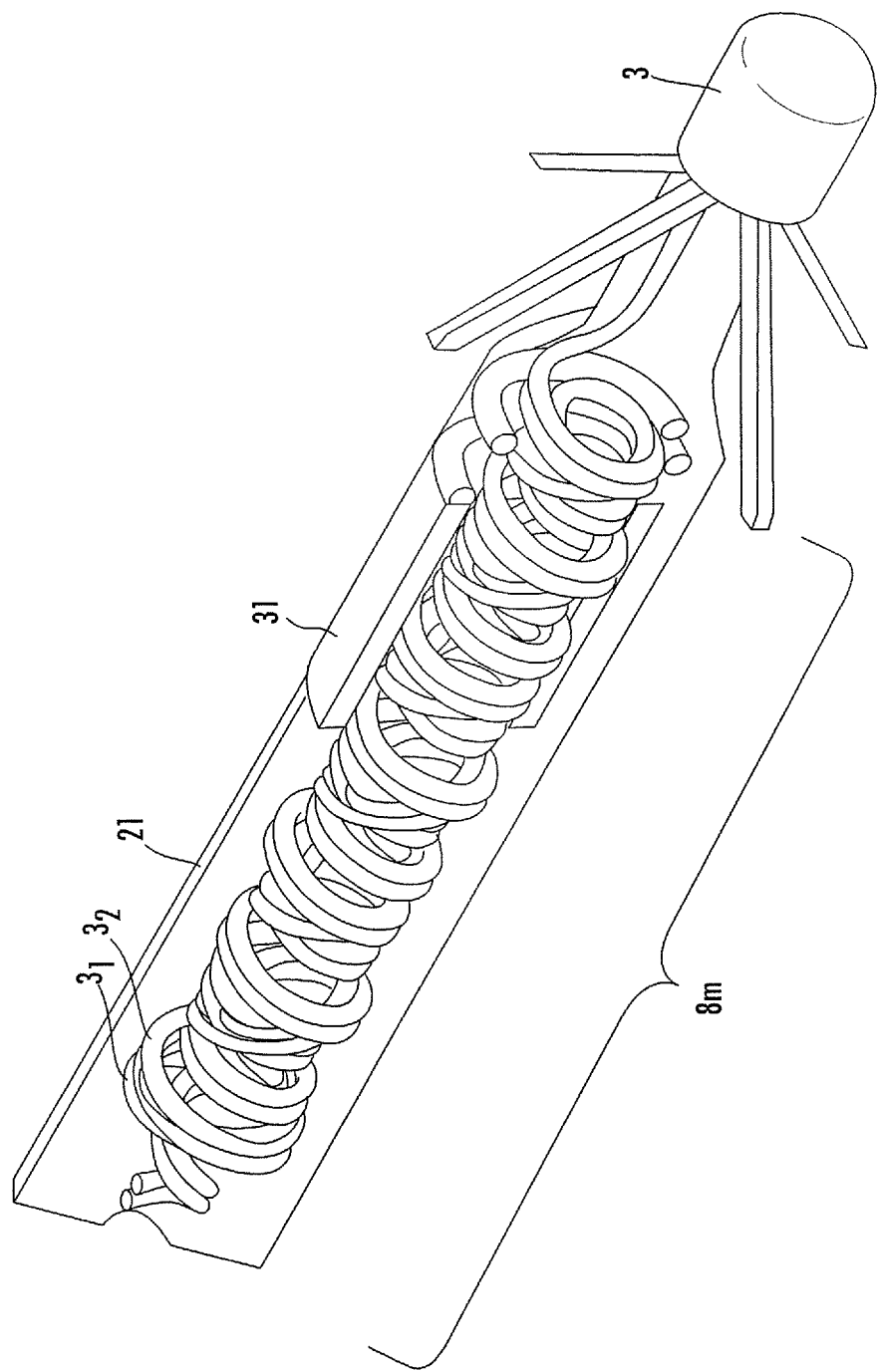
FIG. 55B is a side perspective view of the lead shown in FIG. 55A.

FIGS. 55A and 55B illustrate a distal end portion of a lead 20 suitable for a passive fixation pacemaker lead. As shown, the CSM 8 is a triple stacked CSM 8m having two-conductors CSM 8 with coils in three layers 8i, 8k and 8o. The FS 9c are the inner and outer layers 8i, 8o and the BS 10 is in between the two FS 9c in layer 8k. The lead 20 can include one or more electrodes 31 and a fixation barb 34. As shown, an outer layer 21 of a suitable biocompatible material can be formed over the CSMs 8 to define a substantially constant outer diameter.

Figure 56A:
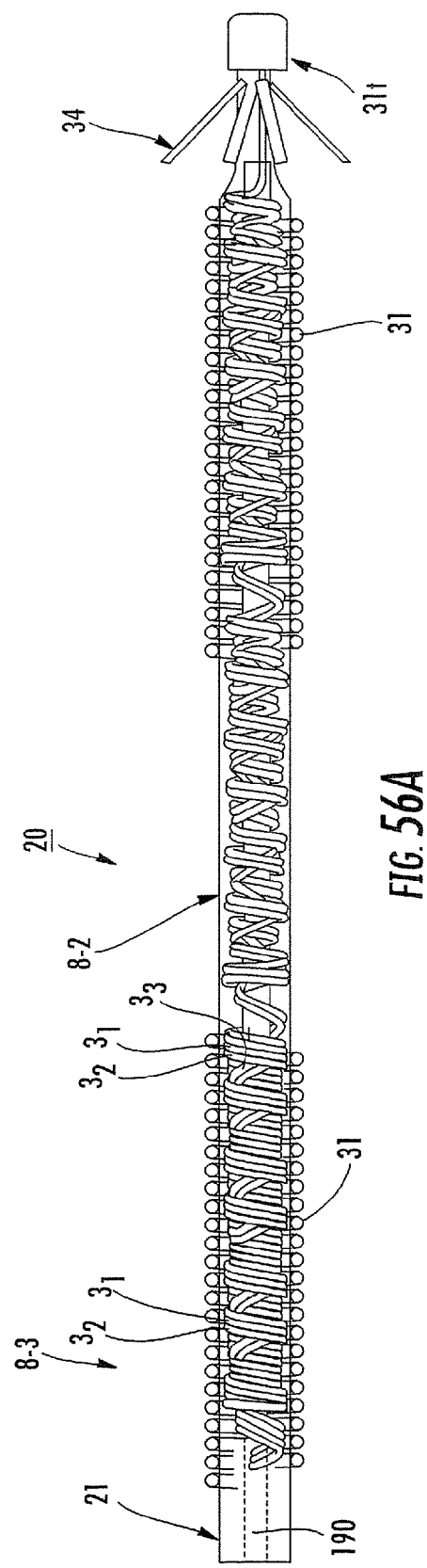
FIG. 56A is a side view of a portion of a lead that may be suitable to be a passive fixation ICD lead according to embodiments of the present invention.
Figure 56B:
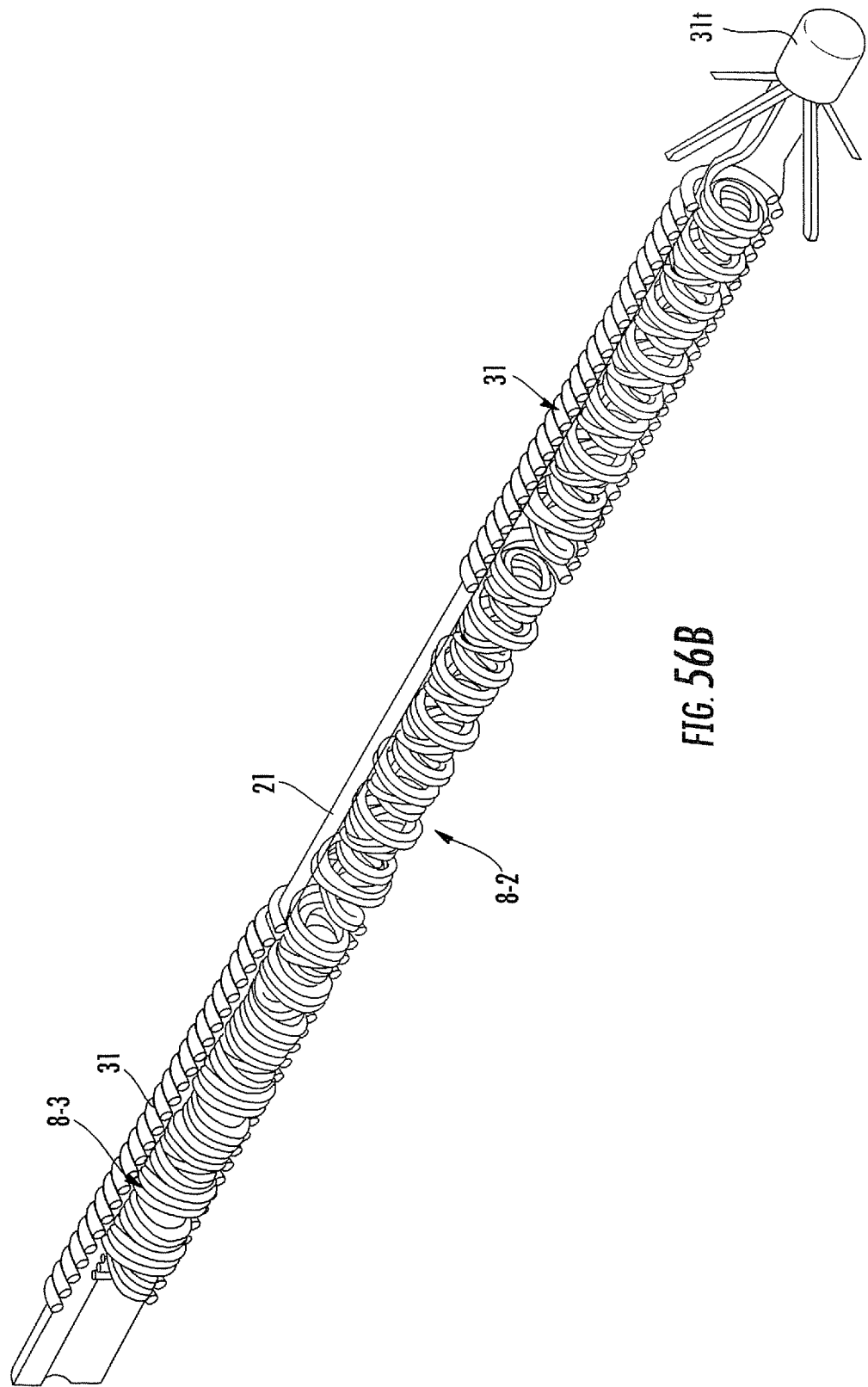
FIG. 56B is a side perspective view of the lead shown in FIG. 56A.

FIGS. 56A and 56B illustrate a distal portion of a lead 20 that may be particularly suitable for a passive fixation ICD lead. As shown, the lead 20 includes both a two-conductor 8-2 and a three-conductor 8-3 CSM 8 (both in a triple-stack configuration). The three conductor CSM 8-3 resides upstream of the two-conductor CSM 8-2 which merges into the tip electrode 31t.

Figures 57A, 57B:
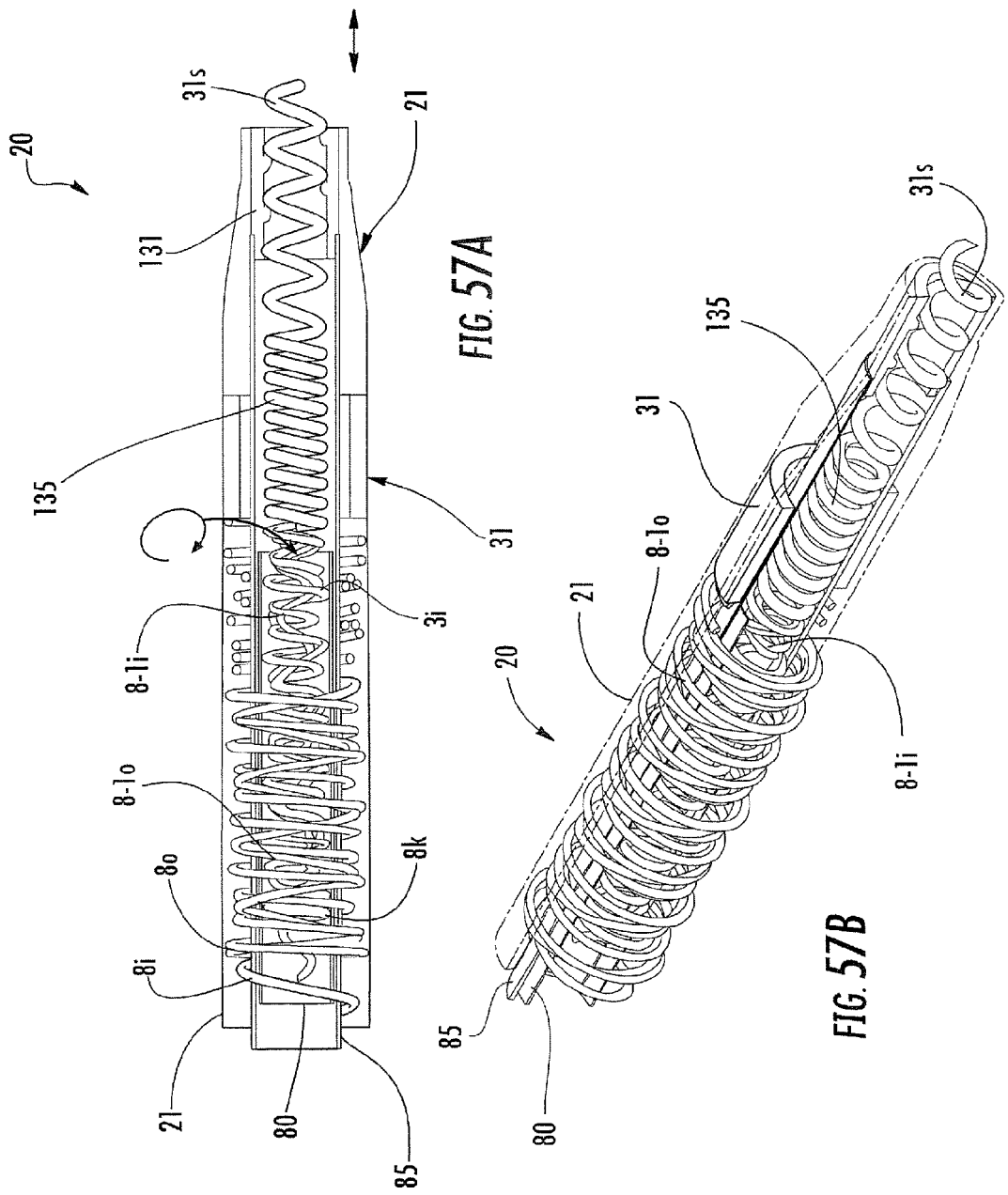
FIG. 57A is a side view of a portion of a lead that may be suitable to be an active fixation pacemaker lead according to embodiments of the present invention.
FIG. 57B is a side perspective view of the lead shown in FIG. 57A.

FIGS. 57A and 57B illustrate another lead 20 which may be particularly suitable for an active fixation pacemaker lead. As shown, the distal tip of the lead 20t can comprise a screw electrode 31s that merges into an expansion spring 135 in communication with a single inner conductor 3i having one or more CSMs 8 (as shown, the inner conductor 3i has a triple-stacked CSM configuration). The lead 20 includes an inner sleeve 80 over the inner conductor 3i and an outer sleeve 85 over the inner sleeve. One or more CSMs can reside over the inner sleeve 85. As shown, a single outer conductor 3o can be configured in one or more outer triple stacked CSM configurations 8-1o that merges into electrode 31. The inner conductor 3i is configured with one or more inner CSM configurations 8-1i and can rotate and/or translate with respect to the outer sleeve 85 to extend the screw electrode 31s out of a lumen defined by the lead. In particular embodiments, the inner sleeve 80 can be a PET shrink sleeve compressed against the inner conductor 3i. The outer sleeve 85 can be a FEP sleeve or other suitable biocompatible material that is bonded or otherwise held to the outer sleeve 85. The lead 20 can include an outer layer 21 over the outer conductor(s)/CSMs 8. A nut 131 can be attached to the distal end of the sleeve 85. Although shown as single conductor outer and inner CSM configurations and illustrated as a triple stack CSM, both the inner and outer conductor configurations can be a plurality of conductors and the CSMs can be formed in other CSM configurations as described herein with respect to other figures.

FIGS. 58A and 58B illustrate another lead 20 which may be particularly suitable for an active fixation ICD lead. This embodiment is similar to that described with respect to FIGS. 57A and 57B, but the lead includes outer two-conductor CSMs 8-2 formed as a triple stack configurations 8m that merge into a single-conductor CSM 8-1o also formed as a triple stack configuration 8m. The two-conductor CSM 8-2o extends to a first electrode 31 and the single CSM 8-1o extends to the next upstream electrode 31. Again, different numbers of conductors and different arrangements or CSM configurations can also be used to form the ICD lead.

FIGS. 45-53 describe methods of fabricating devices and associated fabrication systems or apparatus according to the present invention. Thus, FIGS. 45A-45E illustrate two conductors being cowound on a coiling mandrel to form the stacked trilayer CSM 8m (see, e.g., FIG. 21A). A copper wire or other suitable material elongate substrate, typically but optionally, covered with a tube or sleeve can form the mandrel. FIGS. 46A-46F illustrate a two-layer stacked CSM 8m conductor design during fabrication (see, e.g., FIG. 22A). The coil winder and/or conductors 3 are shown moving back and forth on the mandrel to coil the conductors in the forward and reverse directions (see, e.g., Tables I and II above).

Figure 47A:
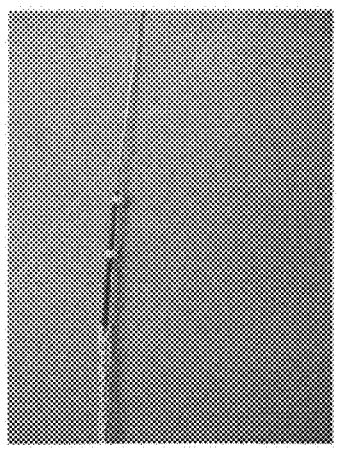
FIGS. 47A-47C are digital photographs of a subassembly of a lead with conductor having wound/stacked current suppression modules according to embodiments of the present invention.
Figure 47B:
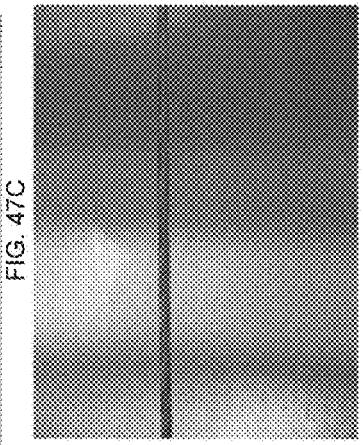
Figure 47C:
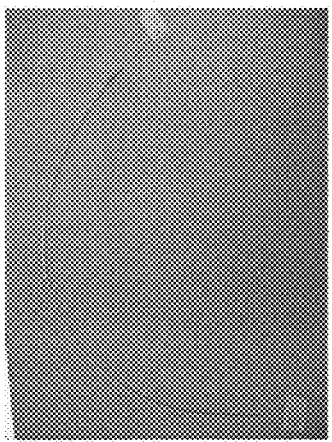
Figure 48A:
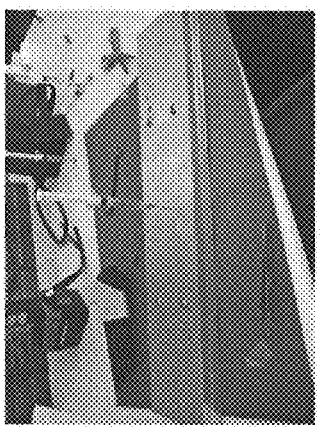
FIGS. 48A-48D are digital images of a mold used to form the flexible lead body of the wound conductor(s) shown in FIGS. 47A-47C according to embodiments of the present invention.
Figure 48B:
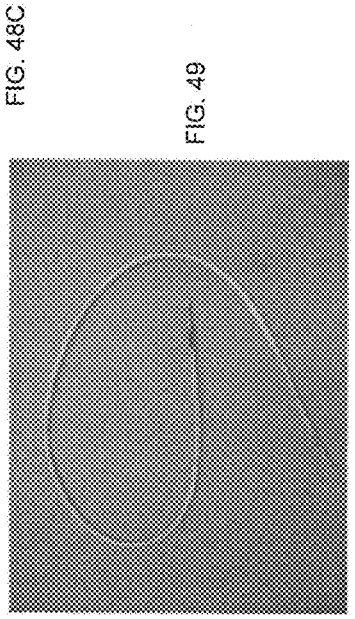
Figure 48C:
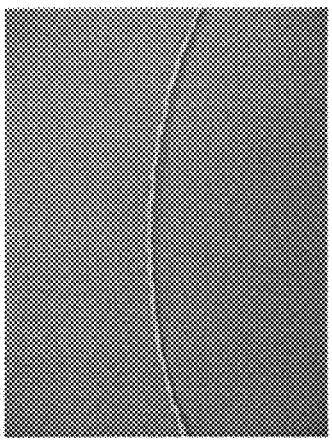
Figure 48D:
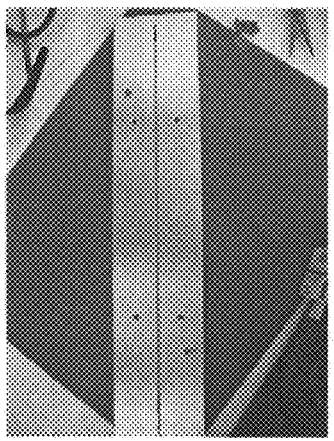

FIGS. 47A-47C show a coiled conductor lead subassembly before an overmolded flexible layer is formed thereover. FIGS. 48A-48D illustrate that the subassembly can be placed in a mold and a material directed therein (shown as being injected when the mold is closed in FIG. 48B). FIGS. 48C and 48D illustrate the molded lead after the mold lid is removed. FIG. 49 illustrates a resultant flexible overmolded lead 20.

Figure 50:
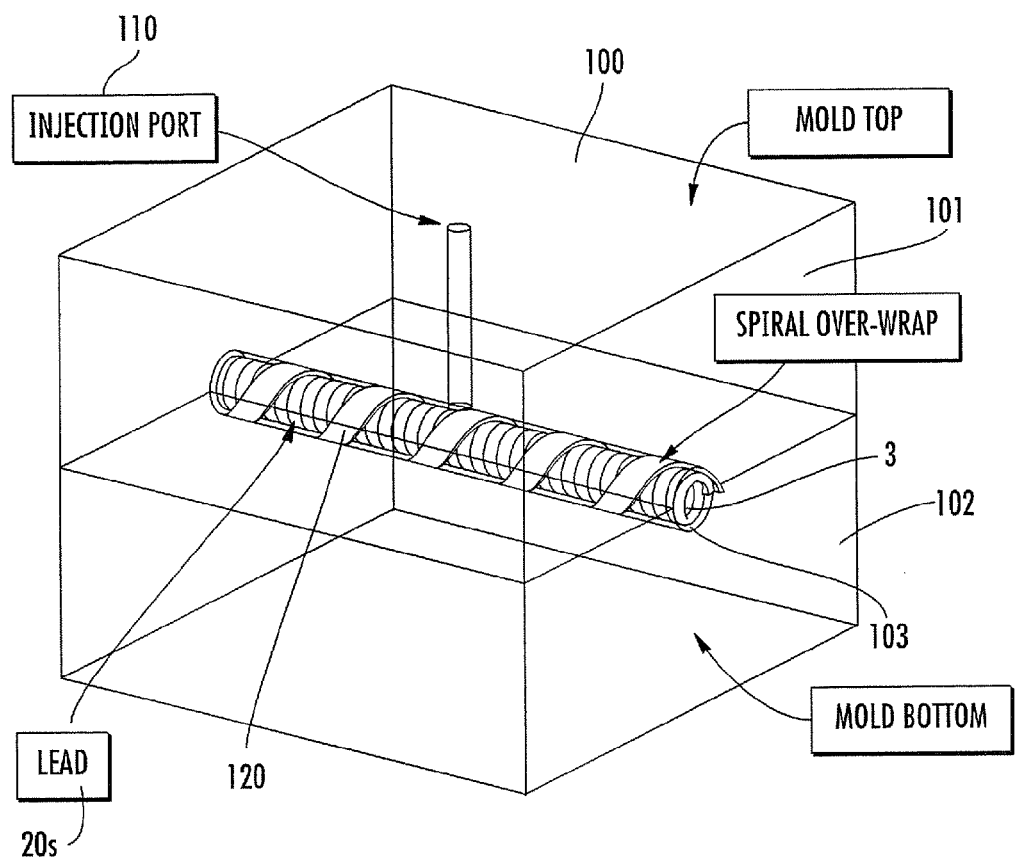
FIG. 50 is a schematic illustration of an exemplary (and optional) mold with a wound conductor subassembly therein according to embodiments of the present invention.
Figure 51:
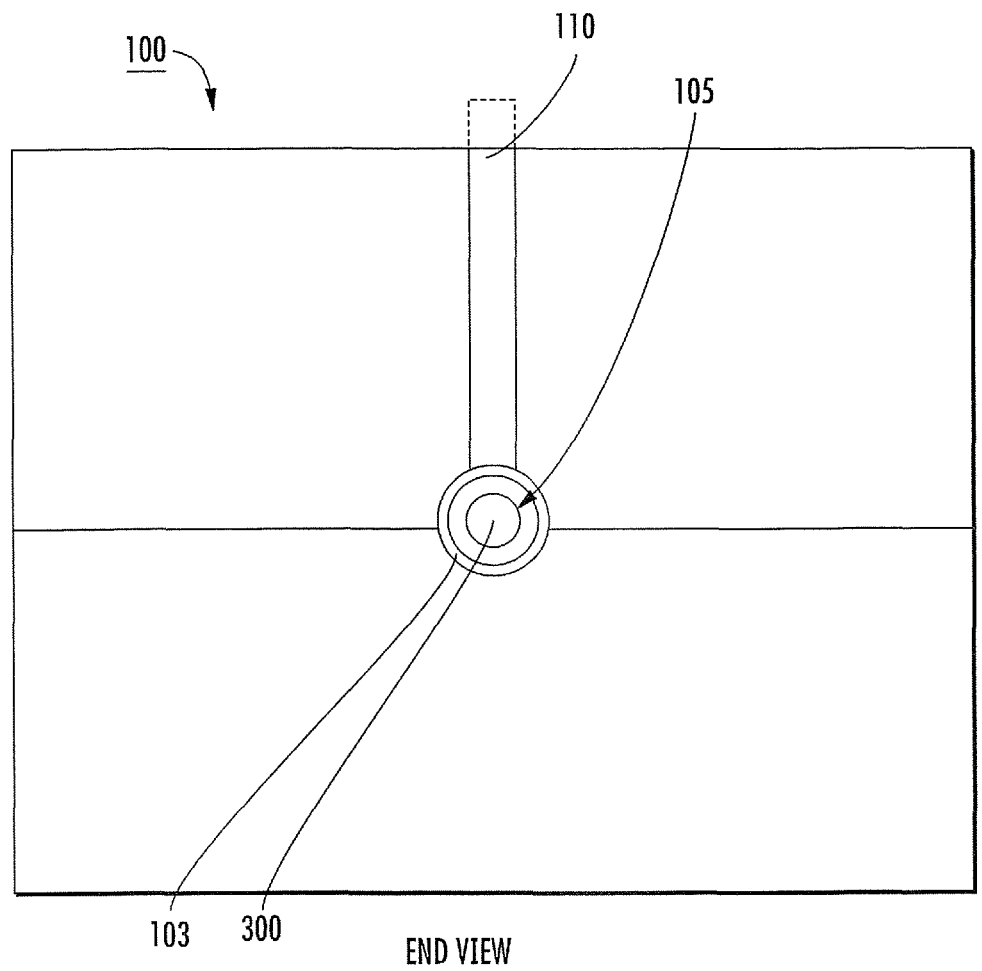
FIG. 51 is an end view of the subassembly and mold shown in FIG. 50.
Figure 52:
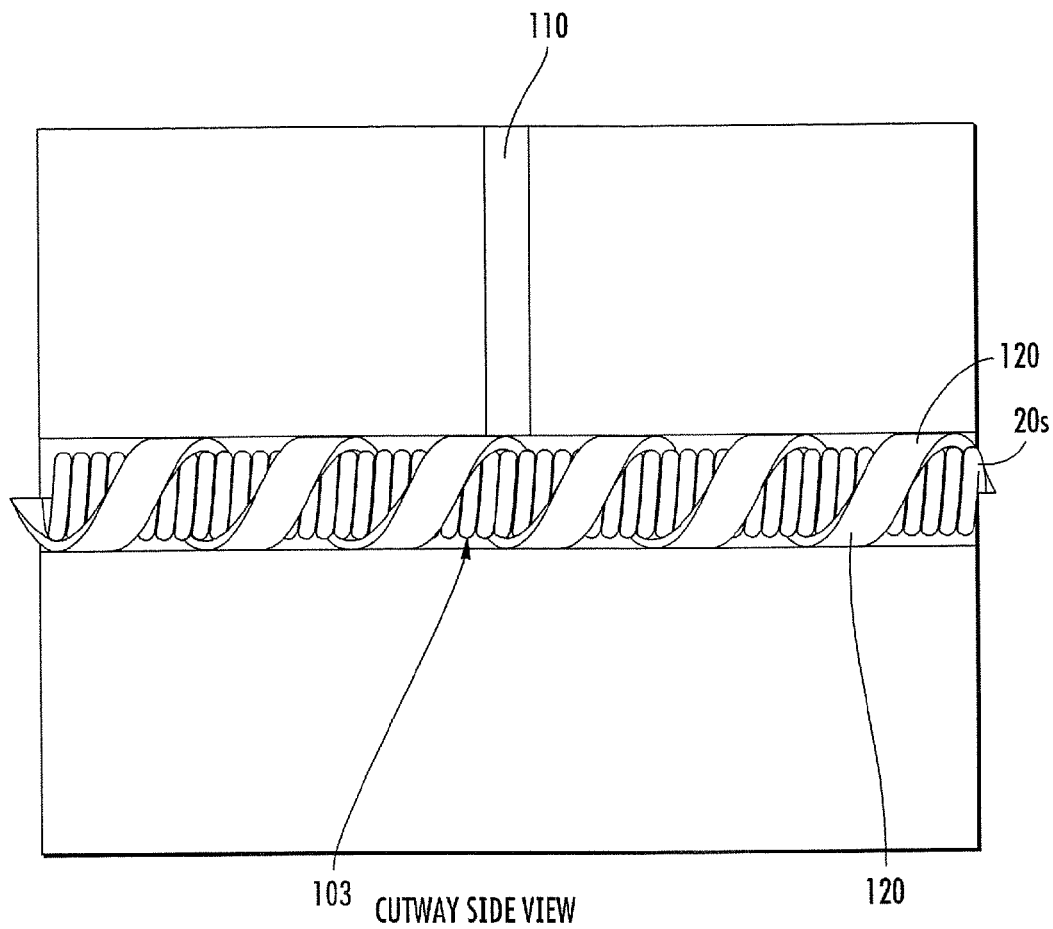
FIG. 52 is a cutaway side view of the subassembly and mold shown in FIG. 50.

FIGS. 50-52 illustrate an exemplary mold 100 used to form the flexible lead 20. The mold 100 is sized and configured to receive the lead subassembly 20s with the coiled conductor(s) 30. The mold has a top and bottom 101, 102 which together form a shallow mold cavity 103 that is sized and configured to receive the subassembly 20s. A spacer 120 can optionally be placed over the subassembly 20s to snugly position the subassembly in the cavity 103 to inhibit the lead subassembly from moving during introduction of a desired moldable material, such as a flowable polymer, that will form the polymer skin or encasement of the lead 20. Movement of the relatively long flexible conductor (wire(s)) may cause varying or a non-uniform thickness in the outer layer and/or skin. The spacer 120 can be a spiral wrap can be placed about the subassembly 20s. The spiral wrap 120 can be configured to allow the molded outer layer to form on the subassembly without affecting the thickness of the skin or outer layer. The spiral wrap 120 can be formed using a silicone tape and/or an application of semi-solid flexible silicone, polyurethane, epoxy or other polymer, co-polymer or derivatives thereof and/or combinations of same or other suitable material. Other spacer 120 configurations may also be used, such as, for example, discrete polymer geometrically shaped members such as pellets or balls and/or holding tabs rods or cones. Over-wrapping the subassembly before placement in the mold cavity 103 can allow the lead subassembly 20s to remain centered even during introduction of the flowable (e.g., gelatinous or liquid) polymer. Suitable overmold layer materials include, but are not limited to, polymers (homopolymer, copolymer or derivatives thereof), silicone, polyurethane, Nylon, Teflon, ETFE, FEP and the like.

The mold 100 can include one or more open exit ports 105 (FIG. 51) that may remain open during molding. The mandrel 300 (FIGS. 51 and 45a) used to coil the subassembly can be removed after the subassembly is molded by pulling from the end of the mold via port 105 (FIG. 51). In other embodiments, the mandrel 300 can be held inside a flexible thin sleeve or tube during the winding. The sleeve can form an integral part of the subsequent lead. The mandrel can remain in position during the molding or pulled from the sleeve prior to inserting the subassembly (held on the sleeve) into the mold cavity 103 (FIG. 52). The mandrel can be inserted into a PTFE tube (1/10 inch inner diameter) and/or be formed by a coated copper or SST wire or other suitable support device.

Figure 53:
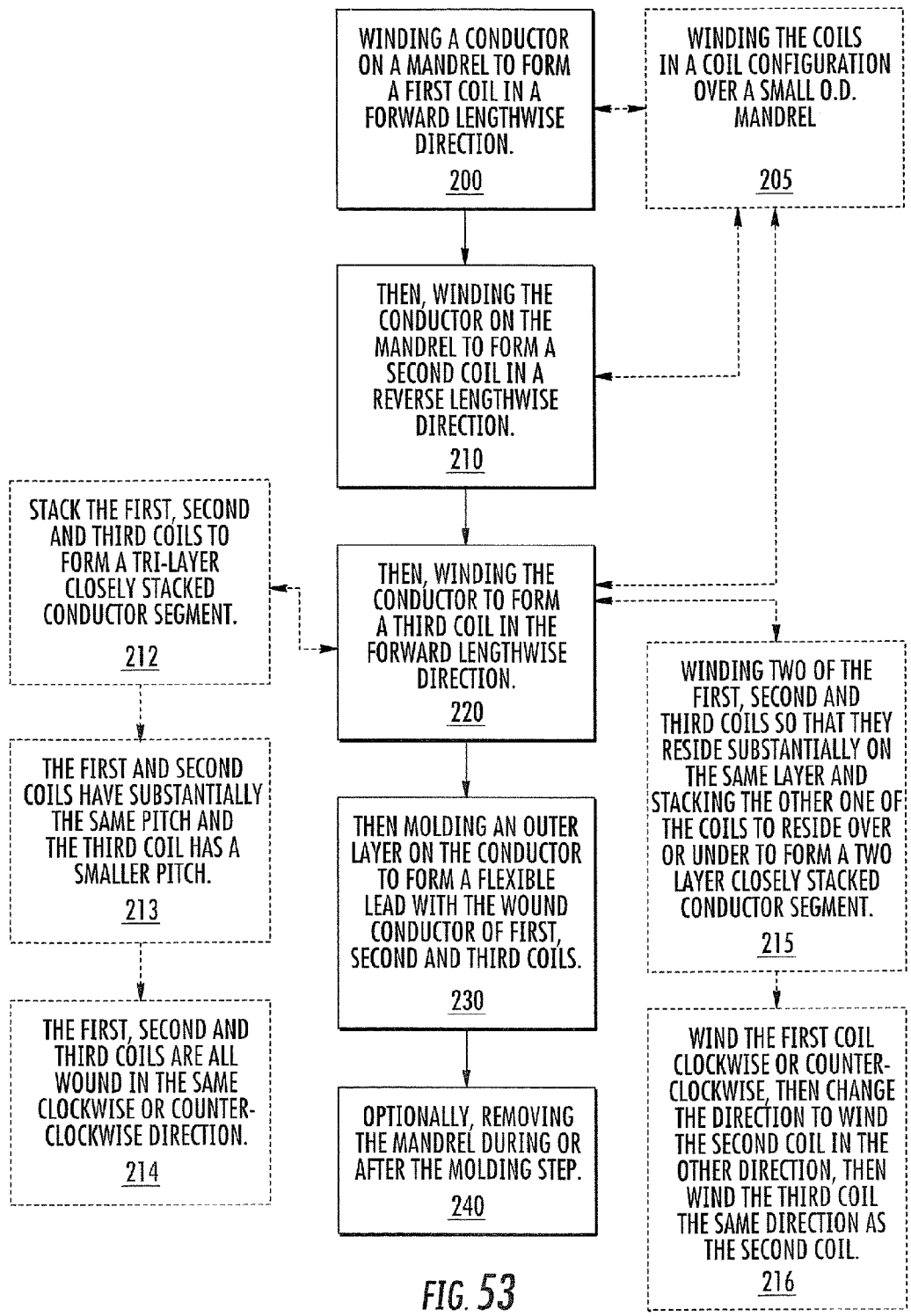
FIG. 53 is a flow chart of operations that can be used to fabricate a lead according to embodiments of the present invention.

Referring to FIG. 53 which describes exemplary operations that can be carried out in support of the fabrication process, the winding operations used to form stacked coils of CSMs can be carried out by winding a conductor on a mandrel to form a first coil in a forward lengthwise (or longitudinal) direction (e.g., left to right) (block 200). The mandrel can be a wire held in tension during the winding operation(s). After winding the first coil, the conductor can be wound over the mandrel to form a second closely spaced coil in a reverse lengthwise direction from the winding direction of the first coil (e.g., right to left) (block 210). The second coil can be formed all or partially over the first coil or all or partially next to the first coil on the same layer as the first coil in the gaps formed by the pitch of the first coil. Then, the conductor can be coiled in a third coil in the forward lengthwise direction (e.g., left to right, the same longitudinal direction as the first coil) (block 220). This can be repeated for a desired number of CSMs. Next an overmolded outer layer can be molded onto the conductor with the coils (block 230). Optionally, the mandrel can be removed from the center of the stacked coils before, during or after the molding step (block 240). In some embodiments the mandrel is placed in the mold with the lead subassembly and removed (pulled from the lead body) after about 10-30 minutes or longer (e.g., 1-3 hours) after the polymer overcoat material is placed in the mold and the mold material heated or cured as desired.

The outer surface layer can have a substantially constant diameter formed over the stacked coils. Also, although some embodiments describe a two or three layer stacked-configuration, additional numbers of stacked layers may also be used, e.g., four, five, six, seven, eight or even more by continuing the back and forth winding of the conductor.

Although the overmolding process has been described above, in other embodiments, other types of manufacturing processes can be used to form the biocompatible outer coating to form a suitable biocompatible substantially constant outer diameter (for at least a portion of the lead). In some embodiments, the outer diameter is not constant, but varies over the length of the lead at least one or more times. Examples of alternative outer layer forming processes include extrusion, injection molding and heated draw down. For example, in an extrusion tube, such as a silicone tube with an inner diameter that is smaller than the conductor winding can be expanded (such as, for example, using hexane). Once expanded, the wound conductor body can be placed inside the tube. As the hexane or other expander evaporates, the tube contracts to original size against the coil winding configuration. The electrodes (where used) can then be attached and an overlayer formed over them as appropriate, typically using liquid injection molding. Another alternative is the use of standard injection molding which may include silicone or a thermoplastic polymer such as thermoplastic polyurethane (e.g., Pellethane™) in standard injection molding equipment. Pellethane™ is available from Dow Chemicals, Inc.

Yet another process that may be used is heated drawdown. This process employs a heated die that is drawn across a thermoplastic extruded tube (such as Pellethane™), to cause the tube material to reflow. As the material reflows it is drawn down on the conductor winding body. The extruded tube can have a slightly larger inner diameter than the outer diameter of the conductor winding body and the conductor winding body is placed inside the tube. The assembly can then be loaded into a Drawdown machine such as one manufactured by Interface Associates of Laguna Niguel, Calif. The inner diameter of the die (the final desired outer diameter of the lead) is smaller than the outer diameter of the tubing. The die is heated to a temperature that causes the thermoplastic material to flow. The die is drawn across the length of the conductor winding body causing the material to produce a smooth and substantially constant outer diameter over the length of the body.

In some embodiments, one part of the lead may be thicker than others. For example, a proximal portion of the lead may be reinforced to provide increased durability or fatigue resistance while at least the distal portion can be low profile with a smaller diameter or size. In other embodiments, a lead extension 20e (FIG. 30B) can extend between one lead and another lead or implantable or external component (e.g., IPG).

The conductor(s) can be wound over the (thin) mandrel directly or via a sleeve over the mandrel (block 205). That is, rather than winding the conductor(s) to have a tight compressive force against the mandrel (or underlying sleeve), the coils can be formed to (directly or indirectly) contact the mandrel with a substantially constant force but with minimal compression.

The winding operations can be carried out to from two of the coils substantially on one layer and the other in another layer to form a two-layer stacked coil configuration (block 215). The first coil can be wound in a clockwise direction, the second in a counterclockwise direction, and the third in the counterclockwise direction (or the windings can be reversed, with the first coil in the CCW direction and the second and third in the CW direction) (block 216). Winding of the third coil on the upper or top layer can continue forward to form the first (lower) forward layer of the next adjacent coils. To facilitate the conductor remaining in position as the winding transitions to the opposing winding direction, an end portion of the first coil can be held in position while the reverse rotational turning is initiated for the second coil. In some embodiments, the winding can be carried out using a conductor of about 0.007 inches O.D, with a starting winding O.D. (mandrel size) of about 0.023 inches. The conductor(s) can be wound for about 30-60 revolutions right (clockwise), typically about 32-45 revolutions, at a pitch of about 0.05 inches followed by about 30-60 revolutions left (with the winding changed to counterclockwise), typically about 32-45 revolutions, with the conductor falling into the gap in the first coil spacing over the mandrel, followed by winding greater than 60 revolutions to the right (counterclockwise), typically about 78-110 revolutions to the right, at a pitch of about 0.02 inches. In some particular embodiment, for a lead having a length of about 57.5 cm can have about 10 CSMs 8.

So, to form a double stack design, during the winding process, the conductor feed head direction changes direction and the coil wind direction also changes direction. Because the pitch of each of the first two layers is typically greater than about two times the conductor thickness and the coil wind direction is reversed, the first two layers sit substantially side-by-side. Other pitches and numbers of revolutions can be used to form the double-stack configurations. The winding operations can be repeated a plurality of times to form multiple CSMs 8 along a length of a lead (e.g., MCSMs).

The winding operations can be carried out to stack the coils in three or more different stacked layers (e.g., a tri-layer configuration) (block 212). The first and second coils can have substantially the same pitch and the third can have a smaller (closer) pitch (block 213). The first, second and third coils can all be wound in the same rotational direction (either one of the clockwise or counterclockwise directions) (block 214). The feed head serially changes directions three times to form the three coils (from forward to backward/reverse to forward again) but the rotational winding direction remains the same. In some embodiments, the winding or turning can be carried out using a conductor (e.g., wire) of about 0.007 inches O.D, with a starting winding O.D. (mandrel size) of about 0.023 inches. The winding can be carried out by winding the conductor(s) about 20-60 revolutions in a first direction for the first layer, e.g., right (clockwise) with a pitch of about 0.05 inches, typically about 32 to about 38 revolutions right, then winding about 20-60 revolutions in the opposite direction for the second layer, e.g., left at a pitch of bout 0.05 inches, typically about 32 to about 38 revolutions left, then winding the third layer in the first direction again, e.g., right, for between about 30-110 revolutions right, typically about 78-94 revolutions, at a pitch of about 0.02 inches. The third layer typically has an increased number of revolutions relative to the first and second layers.

The last CSM of the conductor can be fabricated so that the third layer coil terminates with a larger pitch that is larger than both the first, second and most of the third layer coils (e.g., about 0.070 inches relative to the revolutions of the remainder of the layer which, in some embodiments is at about 0.20 inches). Some resulting multi-conductor configurations can have a multi-layer stacked transverse cross-sectional size that is between about 0.025 inches to about 0.1 inches, typically between about 0.056 inches to about 0.080 inches. Other pitches and numbers of revolutions can be used to form a triple or even greater layer of stacked coils. The winding operations can be continuously or substantially continuously repeated a plurality of times to form a plurality of CSMs 8 along a length of a lead. For a lead 20 having a length of about 72 cm, the CSMs 8 can have a length of about 4 cm and the lead can have about 17 CSMs 8.

While not wishing to be bound to any one method of forming the conductor MCSMs, an exemplary set of operations is provided below that can be used to carry out a winding operation for a two conductor three-layer lead using the Accu-winder model 16 noted above.

1.1 Coil Winder Set-Up
  1.1.1 Turn the coil winder ON and the computer ON.
  1.1.2 Turn the air compressor ON, set air pressure to a minimum of 60 PSI
  1.1.3 Set air pressure on the coil winder to about 20 PSI, cycle foot pedal/actuator several times and readjust as necessary.
  1.1.4 Load two copper wire spools on the coil winder carriage.
  1.1.5 Orient the spools such that the wire leaves from the posterior side of the spools and rotates the spools clockwise during winding.
  1.1.6 Manually slide the carriage from left to right to ensure no obstacles, position carriage to far left position for remainder of set-up. (Note: All references herein to orientation on coil winder are from facing the coil winder i.e., operator's perspective. The coil assembly produced via this process are referenced such that the left end of the coil becomes the distal end and the right end becomes the proximal end).
  1.1.7 Loading a Coiling Mandrel
    1.1.7.1 Slide the inner liner over the coiling mandrel.
    1.1.7.2 Trim the excess length of the inner liner so that the ends are flush with the coiling mandrel.
    1.1.7.3 Secure the coiling mandrel/inner liner at both ends of the coil winder, beginning with the left side. (Note: the coiling mandrel/inner liner should hit the inside stops of both chucks. Chucks should be tightened carefully so that the coiling mandrel/inner liner is centered and tightly gripped).
    1.1.7.4 After securing the left side chuck, depress and hold foot pedal to advance tensioning mechanism on right chuck. Secure coiling mandrel/inner liner in right chuck. Release foot pedal. To ensure proper tensioning, confirm that a portion of the air cylinder is visible.
  1.1.8 Coil Winder Settings
    1.1.8.1 Confirm that toggle switch is set to "CW" (clockwise)
    1.1.8.2 Confirm coil wire guide is attached to the coil winder and is adjusted such that the center of the coil wire guide tube is centered or slightly below the level of the coiling mandrel/inner liner.
    1.1.8.3 Confirm that the coil wire guide tube is perpendicular to the coiling mandrel/inner liner.
    1.1.8.4 Confirm that the spacing between the coil wire guide tube and the coiling mandrel/inner liner is 0.090" using a pin gauge.
    1.1.8.5 Adjust upper and lower felt tensioning clamps such that the distance between the top of the screw head and the top of the felt tensioning clamp equals approximately 1".
    1.1.8.6 Set tensioning guide roller to 30.
  1.1.9 Coil Winder Control Settings
    1.1.9.1 From the desktop of the coil winder controller, select the folder: "2 conductor leads", then select the application file "Winder9".
    1.1.9.2 Press "w" to choose "wind an existing coil" from the menu prompt.
    1.1.9.3 Enter file name. At the next prompt, select "n" to not display the data.
    1.1.9.4 Position safety fence to the furthest right position.
  1.1.10 Confirm correct RPMs of the coil winder according to the following steps:
    1.1.10.1 Where prompted, press "w".
    1.1.10.2 Simultaneously press "enter" on keyboard and start the stop watch.
    1.1.10.3 Allow the coil winder to run for 60 seconds, then disengage the safety clutch to stop the coil winder.
    1.1.10.4 Confirm on the monitor that the "Revolutions Count" equals 60±5 RPMs.
    1.1.10.5 If the "Revolutions Count" does not equal 60±5 RPMs, then adjust the speed control dial and repeat the steps above until the desired speed is reached.
  1.1.11 Reset coil winder by turning power off, then on. Close "winder9" window on coil winder controller.
  1.1.12 Perform "phantom run" to warm up coil winder according to the following steps.
    1.1.12.1 Set coil winder controller settings as outlined above.
    1.1.12.2 Where prompted, press "w", then press "enter".
    1.1.12.3 Allow winder to run through full winding process.
    1.1.12.4 Disengage carriage and slide to left most position.
  Feed the copper wire through the top left two guiding tubes (with the left spool wire through the left tube and the right spool wire through the right tube); through the upper felt tension clamp; through the guide/tension rollers; through the lower felt tension clamp; through the coil winder guide and under the mandrel
  1.1.13 Gently pull on copper wires ensuring that there is a slight tension on wire.
  1.1.14 With the copper wires going under the coil mandrel/inner liner tubing, attach them with to the wire holder on the left chuck. Secure.
  1.1.15 Set coil winder controller settings as outlined above.
  1.1.16 Where prompted, press "w" and press "enter" to start the coil winding process.
  1.1.17 Observe the coil winding process for irregularities.
  1.1.18 On completion of the copper MCSM coil, remove the copper MCSM from the coil winder and inspect the copper MCSM coil:
    1.1.18.1 Coiling mandrel should move with minimal friction;
    1.1.18.2 Coil should not move with respect to the inner liner/tubing;
    1.1.18.3 No gaps wider than two wire diameters through which the coil mandrel can be seen;
    1.1.18.4 No overlaps greater than two wire thicknesses;
    1.1.18.5 Distal section of the most distal CSM exhibits typical three layer construction.
  1.1.19 Replace the copper wire spools with DFT cable spools of approximately the same diameter/amount of wire.
  1.1.20 Feed the DFT cable through the top left two guiding tubes (with the left spool wire through the left tube and the right spool wire through the right tube); through the upper felt tension clamp; through the guide/tension rollers; through the lower felt tension clamp; and through the coil winder guide.
  1.1.21 Gently pull on DFT cable ensuring that there is a slight tension on cable.
1.2 MCSM Assembly
  1.2.1 If not already in position, move the carriage and safety fence to the furthest left position.
  1.2.2 Load a coiling mandrel according to steps outlined above.

1.2.3 Set coil winder controller settings as outlined above.
1.2.4 Where prompted, press "w" and press "enter" to start the coil winding process.
1.2.5 Observe the coil winding process and note any irregularities on the back of the production router.
1.2.6 Apply adhesive (typically UV glue) to the single layer coil at the proximal end of the coil (e.g., using an acid brush); as appropriate, UV cure for 20 seconds; and confirm that the coil/cables are secure on the inner liner tubing. Repeat if necessary.
1.2.7 Trim the cable behind the coil winder guide, remove the coil assembly from the winder and slide a 0.070" ID PET HST×1 cm over 5-7 mm of the single layer coil at the proximal end and the remainder over the adjacent CSM.
1.2.8 Set the hot air gun to 2.5 on air and 5 on heat and run for 2-3 minutes before use.
1.2.9 Holding the air gun nozzle 5-10 cm away from the PET HST, shrink the PET HST tubing to secure the cables and the coil to the inner tubing/liner. If the PET HST was damaged during the heat shrink process, remove the PET HST and apply a new section of PET HST following the same process.
1.2.10 Trim the distal ends of the inner tubing/liner, which were inside the chucks.
1.2.11 Mark the ends of the coiled section on the inner tubing.
1.2.12 Serialize the coil: Place the coil assembly in a transport tube and assign a number to the coil using the following code: month-day-year-lead number (e.g. 081307-1). Label the transport tube with the lead/coil number.
1.2.13
1.3 MCSM Coil Assembly Inspection:
1.3.1 Measure and record length of the MCSM. Length should equal 67.5±1.5 cm.
1.3.2 Inspect the movement of the coiling mandrel in the inner tubing/liner. The coil mandrel should move with minimal friction.
1.3.3 Coil should not move with respect to the inner liner/tubing.
1.3.4 Inspect coil uniformity with Micro Vu.
    1.3.4.1 No gaps wider than two wire diameters through which the coil mandrel or underlying sleeve can be seen;
    1.3.4.2 No overlaps greater than two wire thicknesses;
    1.3.4.3 Distal section of the most distal CSM exhibits typical three layer construction.
1.4 Electrode Assembly:
The electrodes can be attached to the MCSM in the following order:
    Proximal-Distal (IPG) electrode
    Proximal-Proximal (IPG) electrode
    Distal-Proximal/ground electrode
    Distal-Distal/sensing electrode
Note: Electrode labeling is as follows, the first term identifies the end of the MCSM, the second term refers to the relationship between the two electrodes on each end.
Note: The Electrode Assembly process can be conducted under a microscope.
1.4.1 Proximal Electrodes Connection:
    1.4.1.1 At the proximal (PET heat shrink) end of the MCSM assembly, uncoil both conductors from the inner tube/liner to the point where the PET heat shrink begins.
    1.4.1.2 Remove the excess adhesive with the aid of a microscope, as needed, being careful not to damage the inner tube/liner.
    1.4.1.3 Remove the ETFE insulation from the full length of a single conductor. Pull conductor straight, apply flux and tin the conductor with solder. Wipe excess flux using IPA and Kimwipe.
    1.4.1.4 Slide the distal end of the electrode to the beginning of the PET heat shrink with both cables inside the electrode. Solder the electrode to the tinned cable using minimal solder and flux by heating the cable itself at the proximal junction of the cable and the electrode.
    1.4.1.5 Gently pull the electrode to ensure a good solder joint. Trim excess uninsulated cable length, which may be extending outside the electrode.
    1.4.1.6 Remove the ETFE insulation from the second cable, beginning 6 mm away from the proximal end of the previously soldered electrode. Pull cable straight, apply flux and tin the conductor with solder. Wipe excess flux using IPA and Kimwipe.
    1.4.1.7 Slide a 5 mm long piece of 0.042" PET HST over the inner tubing/liner and the cable so that the distal end of the heat shrink is flush with the proximal end of the previously soldered electrode.
    1.4.1.8 Heat shrink the tubing as above.
    1.4.1.9 Slide the electrode and space it such that there is a 6 mm gap between the electrodes. Solder the electrode to the tinned cable using minimal solder and flux by heating the cable itself at the proximal junction of the cable and the electrode.
    1.4.1.10 Gently pull the electrode to ensure good solder joint. Trim excess uninsulated cable length, which may be extending outside the electrode.
1.4.2 Distal Electrode Connection
    1.4.2.1 Using the multimeter identify the cable corresponding to the proximal-distal electrode.
    1.4.2.2 Using a blade, remove the ETFE insulation beginning 5 mm from the distal end of the first CSM. Pull cable straight, apply flux and tin the conductor with solder. Wipe excess flux using IPA and Kimwipe.
    1.4.2.3 Slide the distal-proximal electrode with the cables inside the electrode to the point where the insulation on the tinned cable ends. Solder the electrode to the tinned cable using minimal solder and flux by heating the cable itself at the distal junction of the cable and the electrode.
    1.4.2.4 Gently pull the electrode to ensure good solder joint. Trim excess uninsulated cable length, which may be extending outside the electrode.
    1.4.2.5 Using a blade, remove the ETFE insulation from the second cable, beginning 9 mm away from the distal end of the previously soldered electrode. Pull cable straight, apply flux and tin the conductor with solder. Wipe excess flux using IPA and Kimwipe.
    1.4.2.6 Slide an 8 mm long piece of 0.042" PET HST over the inner tubing/liner and the cable so that the proximal end of the heat shrink is flush with the distal end of the previously soldered electrode.
    1.4.2.7 Heat shrink the tubing as above.
    1.4.2.8 Slide the electrode and space it such that there is a 9 mm gap between the electrodes. Solder the electrode to the tinned cable using minimal solder and flux by heating the cable itself at the distal junction of the cable and the electrode.

Those of skill in the art will appreciate that other operations and/or different parameters may be used and the scope of the invention is not to be limited to this example. Also, this example is for a two-conductor lead formed into a tri-layer MCSM configuration so additional coils of conductor may be used where more than two conductors are being formed into the lead.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. An RF/MRI compatible lead having a proximal end and a distal end, the lead comprising:
   an outer layer of a biocompatible, non-conductive polymer material extending along a portion of the lead;
   at least one electrode disposed along the distal end of the lead;
   at least one insulated conductor extending along the lead and electrically coupled to the at least one electrode, each of the at least one insulated conductor having a length with opposing distal and proximal end portions, each of the at least one insulated conductor having at least one segment with a multi-layer coil configuration, each multi-layer coil configuration being covered by the outer layer of the biocompatible, non-conductive polymer material and being formed from a single one of the at least one insulated conductor and comprising a first forward coiled section that extends in a forward lengthwise direction for a first forward physical length, then turns to merge into a proximately positioned reverse coiled section that extends in a substantially opposing reverse lengthwise direction for a reverse physical length, then turns to merge into a proximately positioned second forward coiled section that extends in the forward lengthwise direction for a second forward physical length, wherein the first forward coiled section, reverse coiled section, and second forward coiled section of the multi-layer coil configuration are each part of the single one of the at least one insulated conductor,
   wherein the lead is flexible and is configured and arranged for insertion into a body of a patient.

2. A lead according to claim 1, wherein, for the multi-layer coil configuration of at least one of the at least one segment, at least two of the first forward section, the second forward section, and the reverse coiled section have substantially constant diameter coil configurations.

3. A lead according to claim 1, wherein, for the multi-layer coil configuration of at least one of the at least one segment, the first forward coiled section, the second forward coiled section and the reverse coiled section are substantially concentric.

4. A lead according to claim 1, wherein, for the multi-layer coil configuration of at least one of the at least one segment, at least some revolutions of the first forward and reverse coiled sections reside proximate each other in a side-to-side lengthwise orientation.

5. A lead according to claim 1, wherein, for the multi-layer coil configuration of at least one of the at least one segment, at least some revolutions of the reverse coiled section reside proximate and over the first forward coiled section.

6. A lead according to claim 1, wherein, for the multi-layer coil configuration of at least one of the at least one segment, at least some revolutions of the reverse coiled section are interleaved with at least some revolutions of at least one of the first or second forward coiled sections.

7. A lead according to claim 1, wherein, for the multi-layer coil configuration of at least one of the at least one segment, the first forward coiled section extends in the forward lengthwise direction about a central axis and has a pitch such that serial revolutions of the first forward coiled section are spaced apart in a lengthwise direction to define gaps, and wherein the reverse coiled section extends about the central axis and has a pitch such that revolutions thereof substantially reside in the gaps of the first forward coiled section.

8. A lead according to claim 1, wherein, for the multi-layer coil configuration of at least one of the at least one segment, the second forward coiled section has more revolutions than that of the first forward and the reverse coiled sections.

9. A lead according to claim 1, wherein, for the multi-layer coil configuration of at least one of the at least one segment, the first forward coiled section resides on a first layer, the reverse coiled section resides on a second layer over the first layer, and the second forward coiled section resides on a third layer over the second layer to define a three-layer stacked conductor coil configuration.

10. A lead according to claim 1, wherein, for the multi-layer coil configuration of at least one of the at least one segment, the first forward coiled section and the reverse coiled section reside on a substantially common layer and the second forward coiled section resides over the first forward and reverse coiled sections to define a two-layer stacked conductor coil configuration.

11. A lead according to claim 1, wherein, for the multi-layer coil configuration of at least one of the at least one segment, the first forward coiled section and the reverse coiled section have substantially the same pitch, and wherein the second forward coiled section has a smaller pitch than that of the first and reverse coiled sections.

12. A lead according to claim 1, wherein each of the at least one conductor has at least one segment with a multi-layer stacked coil configuration of at least one set of the first and second forward coiled sections and the reverse coiled section.

13. A lead according to claim 12, wherein, for the multi-layer coil configuration of at least one of the at least one segment of at least one of the plurality of conductors, the first forward coiled section and the reverse coiled section have substantially the same pitch, and wherein the second forward coiled section has a smaller pitch than that of the first and reverse coiled sections.

14. A lead according to claim 1, wherein at least one segment of the multi-layer coil configuration has more than three layers of stacked coils.

15. A lead according to claim 1, wherein the at least one conductor is a plurality of conductors wherein each of the conductors are insulated along an entire length of the lead forming the multi-layer coil configuration.

16. A lead according to claim 1, wherein the lead has a length and at least a major portion of the length of the lead has a substantially constant outer diameter.

17. A lead according to claim 1, further comprising an elongate inner flexible sleeve residing about a central lengthwise axis with the multi-layer coil configuration encircling the sleeve.

18. A lead according to claim 1, wherein the at least one conductor includes a conductor that has a cross-sectional width of between about 0.0001 inches to about 0.2 inches.

19. A lead according to claim 1, wherein the lead is an MRI/MRS compatible implantable medical lead.

20. A lead according to claim 1, wherein the at least one conductor is a plurality of conductors and the at least one electrode is a plurality of electrodes.

21. A lead according to claim 20, wherein each of the plurality of electrodes is electrically coupled to a different one of the plurality of conductors.

22. A lead according to claim 1, wherein each of the at least one conductor has low DC resistance.

23. A lead according to claim 1, wherein the conductor has at least two segments of the multi-layer coil configuration, and wherein a forward section on a top layer of one multi-layer coil configuration in one segment merges into a forward section on a bottom layer of the other segment.

24. A lead according to claim 1, wherein the at least one conductor is a plurality of conductors, and wherein each of the plurality of conductors is a continuous length of conductor.

25. A lead according to claim 1, wherein the at least one conductor has a plurality of the multi-layer coil configurations serially arranged so that one multi-layer coil configuration segment merges into the next adjacent multi-layer coil configuration along the length of the conductor, each of the multi-layer coil configurations having a length that is less than about 15 cm, and wherein the lead has low DC resistance.

26. A lead according to claim 1, wherein the at least one conductor is a plurality of conductors configured so that at least one multi-layer coil configuration of a first conductor of the plurality of conductors has first forward, reverse, and second forward coiled sections that are substantially concentric to first forward, reverse, and second forward coiled sections of at least one multi-layer coil configuration of a second conductor of the plurality of conductors.

27. A lead according to claim 1, wherein the at least one conductor is a plurality of conductors configured so that one multi-layer coil configuration of a first conductor of the plurality of conductors resides downstream or upstream of one multi-layer coil configuration of a second conductor of the plurality of conductors along a length of the lead.

28. A lead according to claim 1, wherein the at least one conductor is between about 1-100 conductors.

29. A lead according to claim 28, wherein each of at least a majority of the conductors has a plurality of the multi-layer coil configurations, and wherein the at least one conductor has between about 4-100 multi-layer coil configurations along the length thereof.

30. A lead according to claim 1, wherein the at least one conductor comprises first and second conductors, each of the first and second conductors having a plurality of segments with the multi-layer coil configuration, and wherein the segments of the multi-layer coil configurations of the first conductor alternate along the length of the lead with those of the segments of the multi-layer coil configurations of the second conductor.

31. A lead according to claim 1, wherein the lead is sufficiently flexible such that when grasped or suspended at a medial location, opposing long sides and/or end portions thereof drape or droop together.

32. A lead according to claim 1, wherein the at least one conductor comprises a single layer coil extension extending from a segment having a multi-layer coil configuration to an electrode residing upstream thereof.

33. A lead according to claim 1, wherein the lead is configured and arranged for implantation in a patient.

34. An RF/MRI compatible lead comprising:
a plurality of conductors, each of the plurality of conductors having a length with opposing distal and proximal end portions, each of the plurality of conductors having at least one segment with a multi-layer coil configuration, each multi-layer coil configuration being formed from a single one of the plurality of conductors and comprising a first forward coiled section that extends in a forward lengthwise direction for a first forward physical length, then turns to merge into a proximately positioned reverse coiled section that extends in a substantially opposing reverse lengthwise direction for a reverse physical length, then turns to merge into a proximately positioned second forward coiled section that extends in the forward lengthwise direction for a second forward physical length, wherein the first forward coiled section, reverse coiled section, and second forward coiled section of the multi-layer coil configuration are each part of the single one of the plurality of conductors; and
at least one electrode with one or more of the plurality of conductors in communication with the at least one electrode, wherein the lead is configured so that the lead heats local tissue less than about 10 degrees Celsius or does not heat local tissue when a patient is exposed to target RF frequencies generating a peak input SAR of between about 4 W/kg to about 10 W/kg and/or whole body average SAR of between about 2 W/kg to about 4 W/kg.

35. An RF/MRI compatible lead comprising:
a plurality of conductors, each of the plurality of conductors having a length with opposing distal and proximal end portions, each of the plurality of conductors having at least one segment with a multi-layer coil configuration, each multi-layer coil configuration being formed from a single one of the plurality of conductors and comprising a first forward coiled section that extends in a forward lengthwise direction for a first forward physical length, then turns to merge into a proximately positioned reverse coiled section that extends in a substantially opposing reverse lengthwise direction for a reverse physical length, then turns to merge into a proximately positioned second forward coiled section that extends in the forward lengthwise direction for a second forward physical length, wherein the first forward coiled section, reverse coiled section, and second forward coiled section of the multi-layer coil configuration are each part of the single one of the plurality of conductors; and
at least one electrode with one or more of the plurality of conductors in communication with the at least one electrode, wherein the electrical lead heats local tissue less than about 5 degrees Celsius when exposed to target RF frequencies associated with MR Scanners at a peak input SAR of between about 4-10 W/kg and/or a whole body average SAR of between about 2-5 W/kg.

36. A medical lead having a proximal end and a distal end, the medical lead comprising:
- an outer layer of a biocompatible, non-conductive polymer material extending along a portion of the lead;
- at least one electrode disposed along the distal end of the lead; and
- at least first and second insulated conductors extending along the lead and electrically coupled to the at least one electrode, the first and second conductors having at least one multi-layer stacked cowound coil configuration, wherein, for each multi-layer stacked cowound coil configuration, each of the first and second conductors, including the at least one multi-layer stacked cowound coil configuration, being covered by the outer layer of the biocompatible, non-conductive polymer material and having individually a first forward coiled section that extends in a forward lengthwise direction for a first forward physical length, that then turns in a lengthwise direction to merge into a proximately positioned reverse coiled section that extends in a substantially opposing reverse lengthwise direction for a reverse physical length, and that then turns in the lengthwise direction to merge into a proximately positioned second forward coiled section that extends in the forward lengthwise direction,
- wherein the medical lead is flexible and is configured and arranged for insertion into a body of a patient.

37. A medical lead according to claim 36, wherein each of the first and second conductors connect to the same electrode.

38. A medical lead according to claim 36, wherein the at least one electrode comprises a plurality of electrodes, and wherein the first and second conductors connect to a different electrode.

39. A medical lead according to claim 36, wherein the medical lead is configured and arranged for implantation in a patient.

* * * * *